United States Patent
Buchanan et al.

(10) Patent No.: US 6,881,737 B2
(45) Date of Patent: Apr. 19, 2005

(54) SUBSTITUTED TRIAZINYL ACRYLAMIDE DERIVATIVES AND METHODS OF USE

(75) Inventors: John L. Buchanan, Brookline, MA (US); Joseph L. Kim, Wayland, MA (US); Perry M. Novak, Milford, MA (US); Joseph J. Nunes, Andover, MA (US); Vinod F. Patel, Acton, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 10/120,959

(22) Filed: Apr. 10, 2002

(65) Prior Publication Data

US 2003/0139416 A1 Jul. 24, 2003

Related U.S. Application Data

(60) Provisional application No. 60/283,160, filed on Apr. 11, 2001.

(51) Int. Cl.$^7$ .................... C07D 251/16; C07D 251/18; A61K 31/53; A61P 35/00; A61P 13/12
(52) U.S. Cl. .................. 514/241; 544/207; 544/208; 544/209; 544/211; 544/212; 544/213
(58) Field of Search ................... 544/207, 208, 544/209, 211, 212, 213, 206; 514/241

(56) References Cited

U.S. PATENT DOCUMENTS 2,474,194 A  6/1949  Thurston
3,136,816 A  6/1964  Cutler et al.
5,215,569 A  6/1993  Drewes et al.
5,929,080 A  7/1999  Frost

FOREIGN PATENT DOCUMENTS

| CH | 261812 | 9/1949 |
| GB | 1 390 235 | 4/1975 |
| WO | WO 97/19065 | 5/1997 |
| WO | WO 99/01136 | 1/1999 |
| WO | WO 99/65909 | 12/1999 |
| WO | WO 00/43373 | 7/2000 |
| WO | WO 01/25220 | 4/2001 |
| WO | WO-01/25220 A1 * | 4/2001 |

OTHER PUBLICATIONS

Yuki et al., Kobunshi Ronbunshu, 40(11), 739–744, 1983.*
Kurebayashi, Breast Cancer 8(1): 45–51, 2001.*
Somlo et al., Curr. Biol. 11(9): R356–360, 2001.*
Cecil Textbook of Medicine, 20$^{th}$ edition, vol. 1, edited by Bennett, J.C., and Plum, F., 1004–1010, 1996.*
Shapiro et al., (1957) "Guanamine Diuretics" J. Amer. Chem. Soc. 79: 5064–5071.
Smaill et al., (2001) "Tyrosine Kinase Inhibitors. 18. 6–Substituted 4–Anilinoquinazolines and 4–Anilinopyrido [3,4–d] pyrimidines as Soluble, Irreversible Inhibitors of the Epidermal Growth Factor Receptor" J.Med Chem. 44:429–440.

* cited by examiner

Primary Examiner—Venkataraman Balasubramanian
(74) Attorney, Agent, or Firm—Joseph W. Bulock

(57) ABSTRACT

The invention encompasses compounds, analogs, prodrugs and pharmaceutically acceptable salts thereof, pharmaceutical compositions, uses and methods for prophylaxis and treatment of cancer and polycystic kidney disease.

7 Claims, No Drawings

SUBSTITUTED TRIAZINYL ACRYLAMIDE DERIVATIVES AND METHODS OF USE

This application claims the benefit of U.S. Provisional Application No. 60/283,160, filed Apr. 11, 2001, which is hereby incorporated by reference.

FIELD OF THE INVENTION

This invention is in the field of pharmaceutical agents and specifically relates to compounds, compositions, uses and methods for treating cancer and polycystic kidney disease.

BACKGROUND OF THE INVENTION

The invention relates to inhibitors of enzymes that catalyze phosphoryl transfer and/or that bind ATP/GTP nucleotides, compositions comprising the inhibitors, and methods of using and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Phosphoryl transferases are a large family of enzymes that transfer phosphorous-containing groups from one substrate to another. Kinases are a class of enzymes that function in the catalysis of phosphoryl transfer. The protein kinases constitute the largest subfamily of structurally related phosphoryl transferases and are responsible for the control of a wide variety of signal transduction processes within the cell. Almost all kinases contain a similar 250–300 amino acid catalytic domain. The protein kinases may be categorized into families by the substrates they phosphorylate (e.g., protein-tyrosine, protein-serine/threonine, histidine, etc.).

The "kinase domain" appears in a number of polypeptides which serve a variety of functions. Such polypeptides include, for example, transmembrane receptors, intracellular receptor associated polypeptides, cytoplasmic located polypeptides, nuclear located polypeptides and subcellular located polypeptides. The activity of protein kinases can be regulated by a variety of mechanisms. It must be noted, however, that an individual protein kinase may be regulated by more than one mechanism. These mechanisms include, for example, autophosphorylation, transphosphorylation by other kinases, protein-protein interactions, protein-lipid interactions, protein-polynucleotide interactions, ligand binding, and post-translational modification.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, disease and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferative disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

Protein kinases represent a large family of proteins which play a central role in the regulation of a wide variety of cellular processes, maintaining control over cellular function. A partial list of such kinases includes abl, Atk, bcr-ab1, Blk, Brk, Btk, c-kit, c-met, c-src, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70.

Inhibition of such kinases has become an important therapeutic target.

The ErbB receptor family belongs to the subclass I receptor tyrosine kinase superfamily and includes four distinct receptors including epidermal growth factor receptor (EGFR or ErbB1). Erb132 (HER22 or p185neu). Erb133 (HER3), and Erb134 (HER4 or rvro2).

EGFR or ErbB I has been implicated in human malignancy and, in particular, increased expression of this gene has been observed in more aggressive carcinomas of the breast, bladder, lung and stomach. Increased EGFR expression is reported to be associated with increased production of transforming growth factor-alpha (TGF-alpha), resulting in receptor activation by an autocrine stimulatory pathway. Monoclonal antibodies directed against the EGFR, or its ligands TGF-alpha and EGF. have been evaluated as therapeutic agents in the treatment of such malignancies.

While EGF and TGF-alpha do not bind ErbB2, EGF stimulates ErbBI and ErbB2 to form a heterodimer, which activates ErbB I and results in transphosphorylation of ErbB2 in the heterodimer. Dimerization and/or transphosphorylation appears to activate the ErbB2 tyrosine kinase.

While heregulin polypeptides were first identified based on their ability to activate the ErbB2 receptor it was discovered that certain ovarian cells expressing neu and neu-transfected fibroblasts did not bind or cross-link to NDF, nor did they respond to NDF to undergo tyrosine phosphorylation Other biological role(s) of various ErbB ligands have been investigated by several groups. For example, betacellulin has been reported to exhibit growth-promoting activity in vascular smooth muscle cells and retinal pigment epithelial cells. It has been found that ARIA plays a role in myotube differentiation, namely affecting the synthesis and concentration of neuro transmitter receptors in the postsynaptic muscle cells of motor neurons. ARIA has also been demonstrated to increase the number of sodium channels in muscle. It has also been shown that GGFII is mitogenic for subconfluent quiescent human myoblasts and that differentiation of clonal human myoblasts in the continuous presence of GGFII results in greater numbers of myotubes after six days of differentiation.

The potential role(s) that the various ErbB ligands may play in pancreatic cell proliferation and differentiation has also been reported by several investigators. Islet cells (also referred to as Islets of Langerhans) in the pancreas are known to produce the hormones insulin and glucagon. Such islet cells are believed to be derived from stem cells in the fetal ductular pancreatic endothelium.

Various investigators have reported on the effects of particular EGF, heregulin and heregulin related polypeptides on islet cells.

U.S. Pat. No. 5,215,569, issued Jun. 1, 1993, describes substituted pyridines as herbicides. WO99/01136 describes substituted imidazoles as p38 inhibitors. WO00/43373 describes pyrimidinones as kinase inhibitors. Shapiro et al. (J. Amer. Chem. Soc., 79, 5064–71 (1957)) describe guanamines as potential diuretics. U.S. Pat. No. 3,136,816, issued Jun. 9, 1964, describe guanamines as potential diuretics. WO99/65909 describes pyrrolopyrimidine compounds as kinase inhibitors. WO97/19065 describes anilinopyrimidines as kinase inhibitors. U.S. Pat. No. 2,474,194, issued Jun. 21, 1949, describe guanamines as plastic additives. Swiss patent 261812 describes the preparation of triazines. British patent 1,390,235 describes trisubstituted triazines as agents for the treatment of the hormone system. U.S. Pat. No. 5,929,080 describes acrylamide derivatives for the treatment of polycystic kidney disease. Smaill et al. (J. Med. Chem., 44, 429–40 (2001)) describe acrylamides as inhibitors of the EGF receptor.

However, compounds of the current invention have not been described for the treatment of cancer or as kinase inhibitors.

DESCRIPTION OF THE INVENTION

A class of compounds useful in treating cancer and angiogenesis is defined by Formula I

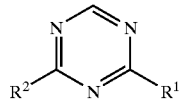

I wherein $R^1$ is selected from $R^3$, $R^8$, —$NHR^3$, —$NHR^5$, —$NHR^6$, —$NR^5R^5$, —$NR^5R^6$, —$SR^5$, —$SR^6$, —$SR^3$, —$OR^5$, —$OR^6$, —$OR^3$, —$C(O)R^3$, heterocyclyl optionally substituted with 1–4 independent $R^4$ on each ring, and $C_1$–$C_{10}$ alkyl optionally substituted with 1–4 independent $R^4$, preferably $R^3$, $R^8$, —$NHR^3$, —$NHR^5$, —$NHR^6$, —$NR^5R^5$, —$NR^5R^6$, —$SR^5$, —$SR^6$, —$SR^3$, —$OR^5$, —$OR^6$, —$OR^3$, —$C(O)R^3$, and 4–10 membered heterocyclyl optionally substituted with 1–4 independent $R^4$, more preferably —$NHR^3$, —$NHR^5$, —$NHR^6$, —$NR^5R^5$, —$NR^5R^6$, and 6–10 membered heterocyclyl optionally substituted with 1–2 independent $R^4$, even more preferably —$NR^5R^5$ and 6–10 membered heterocyclyl optionally substituted with 1–2 independent $R^4$ on each ring, and of particular importance are —$NHR^{5d}$, —$NR^{5c}R^{5d}$, —$N(CH_3)R^{5d}$ and a heterocyclic ring selected from morpholinyl, piperdinyl, piperazinyl, tetrahydroisoquinolinyl and tetrahydroquinolinyl, wherein the heterocyclic ring is optionally substituted with 1–2 independent $R^4$ on each ring;

wherein $R^2$ is selected from —$NHR^{3a}$ and —$NHR^{9a}$, and preferably —$NHR^{3a}$;

wherein $R^3$ is independently selected from aryl optionally substituted with 1–5 independent $R^4$, and heteroaryl optionally substituted with 1–4 independent $R^4$, preferably phenyl optionally substituted with 1–3 independent $R^4$, and 5–10 membered heteroaryl optionally substituted with 1–3 independent $R^4$, and more preferably phenyl optionally substituted with 1–2 independent $R^4$, and 5–10 membered heteroaryl optionally substituted with 1–2 independent $R^4$;

wherein $R^{3a}$ is selected from aryl optionally substituted with 1–3 independent $R^4$, and heteroaryl optionally substituted with 1–3 independent $R^4$; provided $R^{3a}$ is substituted with —$NR^5C(O)R^{10a}$ or is substituted with $C_2$–$C_{10}$alkenyl, $C_2$–$C_{10}$ alkynyl on a nitrogen atom in the heteroaryl ring;

preferably phenyl optionally substituted with 1–2 independent $R^4$, and heteroaryl optionally substituted with 1–2 independent $R^4$; provided $R^{3a}$ is substituted with —$NR^5C(O)R^{10a}$;

more preferably phenyl, pyridyl, indazolyl, benzimidazolyl, benzopyrrolyl, and quinolyl; wherein $R^{3a}$ is substituted with —$NHC(O)R^{10a}$ or —$N(CH_3)C(O)R^{10a}$; wherein $R^{3a}$ may be substituted by 1–2 substituents independently selected from methyl, chloro, fluoro, oxo, trifluoromethyl, methoxy, benzyloxy, morpholinylpropoxy, 1-methylpiperidinylpropoxy and pyridylmethoxy;

wherein $R^4$ is independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, aryl, $R^8$, halo, $SR^5$, $OR^5$, $OC(O)R^5$, $NR^5R^5$, $NR^5R^6$, $NR^5R^{16}$, $COOR^5$, $NO_2$, $CN$, $C(O)R^5$, $C(O)C(O)R^5$, $C(O)NR^5R^5$ $S(O)_nR^5$, $S(O)_nNR^5R^5$, $NR^5C(O)NR^5R^5$, $NR^5C(O)C(O)R^5$, $NR^5C(O)R^5$, $NR^5(COOR^5)$, $NR^5C(O)R^8$, $NR^5S(O)_nNR^5R^5$, $NR^5S(O)_nR^5$, $NR^5S(O)_nR^8$, $NR^5C(O)C(O)$ $NR^5R^5$, $NR^5C(O)C(O)$ $NR^5R^6$, $OC(O)NR^5R^5$, $OS(O)_nNR^5R^5$, $NR^5S(O)_nOR^5$, $P(O)(OR^5)_2$, $C_1$–$C_{10}$ alkyl substituted with 1–3 substituents independently selected from aryl, $R^7$ and $R^8$, and $C_2$–$C_{10}$alkenyl substituted with 1–3 substituents independently selected from aryl, $R^7$ and $R^8$, preferably $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, optionally substituted phenyl, $R^8$, $SR^5$, $OR^5$, $OC(O)R^5$, $NR^5R^5$, $NR^5R^6$, $NR^5R^{16}$, $COOR^5$, $NO_2$, $CN$, $C(O)R^5$, $C(O)C(O) R^5$, $C(O)NR^5R^5$, $S(O)_nR^5$, $S(O)_nNR^5R^5$, $NR^5C(O)NR^5R^5$, $NR^5C(O)C(O)R^5$, $NR^5C(O)R^5$, $NR^5(COOR^5)$, $NR^5C(O)R^8$, $NR^5S(O)NR^5R^5$, $NR^5S(O)_nR^5$, $NR^5S(O)_nR^8$, $NR^5C(O)C(O)NR^5R^5$, $NR^5C(O)C(O)NR^5R^6$, $OC(O)NR^5R^5$, $OS(O)_nNR^5R^5$, $NR^5S(O)_nOR^5$, halo selected from bromo, fluoro and chloro, $C_1$–$C_6$ alkyl substituted with 1–3 substituents independently selected from phenyl, $R^7$ and $R^8$; and $C_2$–$C_6$ alkenyl substituted with 1–3 substituents independently selected from phenyl, $R^7$ and $R^8$, more preferably $C_1$–$C_4$ alkyl, $C_3$–$C_6$ cycloalkyl, optionally substituted phenyl, $R^8$, chloro, bromo, fluoro, $OR^5$, $OC(O)R^5$, $NR^5R^5$, $NR^5R^5$, $COOR^5$, $NO_2$, CN, $C(O)R^5$, $C(O)NR^5R^5$, $SO_2R^5$, $SO_2NR^5R^5$, and $C_1$–$C_4$ alkyl substituted with 1–3 substituents independently selected from optionally substituted phenyl, $R^7$ and $R^8$, even more preferably $C_1$–$C_4$ alkyl, optionally substituted phenyl, bromo, chloro, fluoro, $OR^5$, and $C_1$–$C_4$ alkyl substituted with 1–3 substituents independently selected from optionally substituted phenyl and $R^8$, and of particular interest are methyl, chloro, fluoro, methoxy, benzyloxy, morpholinylpropyloxy, benzyl and pyridylmethylenyl;

wherein $R^5$ is independently selected from H, $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, aryl, $R^9$, $C_1$–$C_{10}$ alkyl substituted with 1–3 substituents independently selected from aryl, $R^7$ and $R^9$;

$C_3$–$C_{10}$ cycloalkyl substituted with 1–3 substituents independently selected from aryl, $R^7$ and $R^9$; and $C_2$–$C_{10}$ alkenyl substituted with 1–3 substituents substituents independently selected from aryl, $R^7$ and $R^9$, preferably H, $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, optionally substituted phenyl, $R^9$, $C_1$–$C_6$ haloalkyl, $C_1$–$C_6$ alkyl substituted with 1–3 substituents independently selected from optionally substituted phenyl, $R^7$ and $R^9$, $C_3$–$C_6$ cycloalkyl substituted with 1–3 substituents independently selected from optionally substituted phenyl, $R^7$ and $R^9$, and $C_2$–$C_6$ alkenyl substituted with 1–3 substituents independently selected from optionally substituted phenyl, $R^7$ and $R^9$;

more preferably H, $C_1$–$C_4$ alkyl, $C_2$–$C_4$ alkenyl, $C_2$–$C_4$ alkynyl, $C_3$–$C_4$ cycloalkyl, optionally substituted phenyl, $R^9$, $C_1$–$C_3$ haloalkyl, $C_1$–$C_3$ alkyl substituted with 1–3 substituents independently selected from phenyl, $R^7$ and $R^9$, and $C_3$–$C_6$ cycloalkyl substituted with a substituent selected from phenyl, $R^7$ and $R^9$, and even more preferably H, $C_1$–$C_4$ alkyl, $C_3$–$C_4$ cycloalkyl, optionally substituted phenyl, $R^9$, $C_1$–$C_3$ haloalkyl, $C_1$–$C_3$ alkyl substituted with 1–3 substituents independently selected from optionally substituted phenyl, and $R^9$, and $C_3$–$C_6$ cycloalkyl substituted with a substituent selected from optionally substituted phenyl, and $R^9$;

wherein $R^{5c}$ is $C_1$–$C_3$ alkyl substituted with a optionally substituted substituent selected from morpholinyl, piperdinyl, and piperazinyl;

wherein $R^{5d}$ is independently selected from indazolyl, benzopyrrolyl, phenyl and cyclopropyl; wherein $R^{5d}$ is optionally substituted with 1–2 substituents independently selected from methyl, phenyl, pyridyl, fluoro, chloro, $CF_3$, hydroxy, methoxy, benzyloxy, acetyl, amino, methylamino, dimethylamino, carboxy, methoxycarbonyl, methylcarbonyl, aminocarbonyl, and $C_1$–$C_3$ alkyl substituted with optionally substituted phenyl and optionally substituted 5–6 membered heterocyclyl;

wherein $R^6$ is independently selected from $C(O)R^5$, $COOR^5$, $C(O)NR^5R^5$, $C(=NR^5)NR^5R^5$, and $S(O)_nR^5$, preferably $C(O)R^5$, $COOR^5$ and $C(O)NR^5R^5$, and more preferably $C(O)R^5$;

wherein $R^7$ is independently selected from halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$, $NR^{10}S(O)NR^{10}R^{10}$, $NR^{10}S(O)_nR^{10}$, and $P(O)(OR^5)_2$, preferably chloro, fluoro, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $S(O)_nNR^{10}R^{10}$, and $NR^{10}S(O)_nR^{10}$, more preferably chloro, fluoro, $CF_3$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $C(O)NR^{10}R^{10}$ and $SO_2NR^{10}R^{10}$, even more preferably chloro, fluoro, $CF_3$, $OR^{10}$, $NR^{10}R^{10}$, $COOR^{10}$, $NO_2$, CN, $C(O)R^{10}$;

wherein $R^8$ is independently selected from 3–8 membered monocyclic, 7–12 membered bicyclic, and 11–14 membered tricyclic ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2, 3 or 4 atoms of each ring may be substituted by a substituent independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, aryl, $R^9$, halo, sulfo, oxo, $SR^5$, $OR^5$, $OC(O)R^5$, $NR^5R^5$, $NR^5R^6$, $NR^6R^6$, $COOR^5$, $NO_2$, CN, $C(O)R^5$, $C(O)NR^5R^5$, $S(O)_nNR^5R^5$, $NR^5C(O)NR^5R^5$, $NR^5C(O)R^9$, $NR^5S(O)_nNR^5R^5$, $NR^5S(O)_nR^9$, $C_1$–$C_{10}$ alkyl substituted with 1–3 substituents independently selected from $R^7$, $R^9$ and aryl; and $C_2$–$C_{10}$ alkenyl substituted with 1–3 substituents independently selected from $R^7$, $R^9$ and aryl, preferably 3–8 membered monocyclic, and 7–12 membered bicyclic ring system comprising 1–3 heteroatoms if monocyclic, or 1–6 heteroatoms if bicyclic, said heteroatoms independently selected from O, N, or S, which may be saturated or unsaturated, and wherein 0, 1, 2, 3 or 4 atoms of each ring may be substituted by substituents independently selected from $C_1$–$C_6$ alkyl, $C_2$–$C_6$ alkenyl, $C_2$–$C_6$ alkynyl, $C_3$–$C_6$ cycloalkyl, optionally substituted phenyl, $R^9$, chloro, fluoro, oxo, $SR^5$, $OR^5$, $OC(O)R^5$, $NR^5R^5$, $NR^5R^6$, $NR^6R^6$, $COOR^5$, $NO_2$, CN, $C(O)R^5$, $C(O)NR^5R^5$, $S(O)$, $NR^5R^5$, $NR^5C(O)R^9$, $NR^5S(O)R^9$, $C_1$–$C_6$ alkyl substituted with 1–3 substituents independently selected from $R^7$, $R^9$ and optionally substituted phenyl, and $C_2$–$C_6$ alkenyl substituted with 1–3 substituents independently selected from $R^7$, $R^9$ and optionally substituted phenyl, more preferably 4–7 membered monocyclic, and 8–11 membered bicyclic ring system comprising 1–3 heteroatoms if monocyclic, or 1–6 heteroatoms if bicyclic, said heteroatoms independently selected from O, N, or S, which may be saturated or unsaturated, and wherein 0, 1, 2, 3 or 4 atoms of each ring may be substituted by substituents independently selected from $C_1$–$C_6$ alkyl, $C_3$–$C_6$ cycloalkyl, optionally substituted phenyl, $R^9$, chloro, fluoro, oxo, $OR^5$, $OC(O)R^5$, $NR^5R^5$, $NR^5R^6$, $NR^6R^6$, $COOR^5$, $NO_2$, CN, $C(O)R^5$, $C(O)NR^5R^5$, $SO_2NR^5R^5$, and $C_1$–$C_6$ alkyl substituted with 1–3 substituents independently selected from $R^7$, $R^9$ and optionally substituted phenyl, and even more preferably 5–6 membered monocyclic, and 9–10 membered bicyclic ring system comprising 1–2 heteroatoms if monocyclic, or 1–4 heteroatoms if bicyclic, said heteroatoms independently selected from O, N, or S, which may be saturated or unsaturated, and wherein 0, 1, 2, 3 or 4 atoms of each ring may be substituted by substituents independently selected from $C_1$–$C_4$ alkyl, optionally substituted phenyl, $R^9$, chloro, fluoro, oxo, $OR^5$, and $C_1$–$C_4$ alkyl substituted with 1–3 substituents independently selected from $R^7$, $R^9$ and optionally substituted phenyl;

wherein $R^9$ is independently selected from 3–8 membered monocyclic, 7–12 membered bicyclic, and 11–14 membered tricyclic ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2 or 3 atoms of each ring may be substituted by a substituent independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, halo, sulfo, oxo, $C_{1-10}$ haloalkyl, $SR^{10}$, $OR^{10}$, $NR^{10}R^{10}$, $NR^{10}R^{11}$, $NR^{11}R^{11}$, $COOR^{10}$, $NO_2$, CN, $C(O)R^{10}$, $S(O)_nR^{10}$, $S(O)_nNR^{10}R^{10}$, and $C(O)NR^{10}R^{10}$, preferably 3–8 membered monocyclic, and 7–12 membered bicyclic ring system comprising 1–3 heteroatoms if monocyclic, or 1–6 heteroatoms if bicyclic, said heteroatoms independently selected from O, N, or S, which may be saturated or unsaturated, and wherein 0, 1, 2 or 3 atoms of each ring may be substituted by a substituent independently selected from $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, halo, oxo, $C_{1-6}$ haloalkyl, $SR^{10}$, $OR^{10}$, $NR^{10}R^{10}$, $NR^{10}R^{11}$, $NR^{11}R^{11}$, $COOR^{10}$, $NO_2$, CN, $C(O)R^{10}$, $S(O)_nR^{10}$, $S(O)_nNR^{10}R^{10}$, and $C(O)NR^{10}R^{10}$, more preferably 4–7 membered monocyclic, and 8–11 membered bicyclic ring system comprising 1–3 heteroatoms if monocyclic, or 1–6 heteroatoms if bicyclic, said heteroatoms independently selected from O, N, or S, which may be saturated or unsaturated, and wherein 0, 1, 2 or 3 atoms of each ring may be substituted by a substituent independently selected from $C_1$–$C_6$ alkyl, $C_3$–$C_6$ cycloalkyl, halo, oxo, $C_1$–$C_6$ haloalkyl, $OR^{10}$, $NR^{10}R^{10}$, $NR^{10}R^{11}$, $NR^{11}R^{11}$, $COOR^{10}$, $NO_2$, CN, $C(O)R$, $SO_2R^{10}$, $SO_2NR^{10}R^{10}$, and $C(O)NR^{10}R^{10}$ and even more preferably 5–6 membered monocyclic, and 9–10 membered bicyclic, ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2 or 3 atoms of each ring may be substituted by a substituent independently selected from $C_1$–$C_4$ alkyl, halo, oxo, $C_1$–$C_4$ haloalkyl, optionally substituted phenyl, $R^8$, $OR^{10}$, $NR^{10}R^{10}$, $COOR^{10}$, $C(O)R^{10}$, $OC(O)R^{10}$, and $C(O)NR^{10}R^{10}$;

wherein $R^9a$ is independently selected from 3–8 membered monocyclic, 7–12 membered bicyclic, and 11–14 membered tricyclic ring system comprising 1–3 heteroatoms if monocyclic, 1–6 heteroatoms if bicyclic, or 1–9 heteroatoms if tricyclic, said heteroatoms independently selected from O, N, or S, which is partially unsaturated, and wherein 0, 1, 2 or 3 atoms of each ring may be substituted by a substituent independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, halo, sulfo, oxo, $C_{1-10}$ haloalkyl, $SR^{10}$, $OR^{10}$, $NR^{10}R^{10}$, $NR^{10}R^{11}$, $NR^{11}R^{11}$, $COOR^{10}$, $NO_2$, CN, $C(O)R^{10}$, $S(O)_nR^{10}$, $S(O)_nNR^{10}R^{10}$, and $C(O)NR^{10}R^{10}$; provided $R^{9a}$ is substituted with —$NR^5C(O)R^{10a}$ or is substituted with $C_2$–$C_{10}$ alkenyl, $C_2$–$C_{10}$ alkynyl on a nitrogen atom in the heterocyclic ring;

preferably 3–8 membered monocyclic, and 7–12 membered bicyclic ring system comprising 1–3 heteroatoms if monocyclic, or 1–6 heteroatoms if bicyclic, said heteroatoms independently selected from O, N, or S, which is partially unsaturated, and wherein 0, 1, 2 or 3 atoms of each ring may be substituted by a substituent independently selected from $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, halo, oxo, $C_{1-6}$ haloalkyl, $SR^{10}$, $OR^{10}$, $NR^{10}R^{10}$, $NR^{10}R^{11}$, $NR^{11}R^{11}$, $COOR^{10}$, $NO_2$, CN, $C(O)R^{10}$, $S(O)_nR^{10}$, $S(O)_nNR^{10}R^{10}$, and $C(O)NR^{10}R^{10}$; provided $R^{9a}$ is substituted with —$NR^5C(O)R^{10a}$, more preferably 4–7 membered monocyclic, and 8–11 membered bicyclic ring system comprising 1–2 heteroatoms if monocyclic, or 1–3 heteroatoms if bicyclic, said heteroatoms independently selected from O, N, or S, which may be saturated or unsaturated, and wherein 0, 1, or 2 atoms of each ring may be substituted by a substituent independently selected from $C_1$–$C_6$ alkyl, $C_3$–$C_6$ cycloalkyl, halo, oxo, $C_1$–$C_3$ haloalkyl, $OR^{10}$, $NR^1OR^{10}$, $NR^{10}R^{11}$, $NR^{11}R^{11}$, $COOR^{10}$, $NO_2$, CN, $C(O)R^{10}$, $SO_2R^{10}$, $SO_2NR^{10}R^{10}$, and $C(O)NR^{10}R^{10}$;

wherein $R^{9a}$ is substituted with —$NR^5C(O)R^{10a}$;

even more preferably 5–6 membered monocyclic, and 9–10 membered bicyclic ring system comprising 1–2 heteroatoms if monocyclic, or 1–3 heteroatoms if bicyclic, said heteroatoms independently selected from O, N, or S, which may be saturated or unsaturated, and wherein 0, 1, or 2 atoms of each ring may be substituted by a substituent independently selected from $C_1$–$C_3$ alkyl, halo, oxo, $C_1$–$C_3$ haloalkyl and $OR^{10}$;

wherein $R^{9a}$ is substituted with —$NR^5C(O)R^{10a}$, particularly dihydrobenzopyrrolyl;

wherein $R^{9a}$ is substituted with —$NHC(O)R^{10a}$ or —$N(CH_3)C(O)R^{10a}$;

wherein $R^{9a}$ may be substituted by 1–2 substituents independently selected from methyl, chloro, fluoro, oxo, trifluoromethyl, methoxy, benzyloxy, morpholinylpropoxy, 1-methylpiperidinylpropoxy and pyridylmethoxy;

wherein $R^{10}$ is independently H; $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, haloalkyl, $C_1$–$C_{10}$ alkyl optionally substituted with 1–3 substituents independently selected from $C_2$–$C_{10}$ alkenyl, $C_2$–$C_{10}$ alkynyl, $C_3$–$C_{10}$ cycloalkyl, $C_4$–$C_{10}$ cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$, and $OC(O)R^{12}$; and phenyl optionally substituted with 1–3 substituents independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$, and $OC(O)R^{12}$, preferably H, $C_{1-6}$ alkyl, $C_{2-6}$ alkenyl, $C_{2-6}$ alkynyl, $C_{3-6}$ cycloalkyl, $C_{4-6}$ cycloalkenyl, $C_1$–$C_6$ alkyl substituted with 1–3 independent, $C_{2-10}$ alkenyl, $C_{2-10}$ alkynyl, $C_{3-10}$ cycloalkyl, $C_{4-10}$ cycloalkenyl, halo, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}(O)R^{12}$, $N(R^{12})(COOR^{12})$ $S(O)_nNR^{12}R^{12}$ and $OC(O)R^{12}$, and phenyl optionally substituted with 1–3 substituents independently selected from $C_{1-6}$ alkyl, $C_{2-6}$ alkenyl, $C_{2-6}$ alkynyl, $C_{3-6}$ cycloalkyl, $C_{4-6}$ cycloalkenyl, halo, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})$, $(COOR^{12})$, $S(O)_nNR^2R^{12}$, and $OC(O)R^{12}$, more preferably H, $C_{1-3}$ alkyl, $C_{3-6}$ cycloalkyl, $C_1$–$C_3$ alkyl substituted with 1–3 substituents independently selected from $C_{3-6}$ cycloalkyl, fluoro, chloro, OR , $NR^{12}R^2$, $COOR^{12}$, $NO_2$, CN, $C(O)R^{12}R^{12}$, $C(O)NR^{12}R^{12}$, $NR^{12}C(O)R^{12}$, $SO_2NR^{12}R^{12}$, and $OC(O)R^{12}$, and phenyl optionally substituted with 1–3 substituents independently selected from $C_{1-3}$ alkyl, $C_{2-3}$ alkenyl, $C_{2-3}$ alkynyl, $C_{3-6}$ cycloalkyl, halo, $OR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $SO_2NR^{12}R^2$, and $OC(O)R^{12}$, and even more preferably H, methyl and $C_1$–$C_3$ alkyl substituted with 1–3 substituents independently selected from fluoro, chloro, hydroxy, methoxy, optionally substituted phenyl and $R^9$, and optionally substituted phenyl;

wherein $R^{10a}$ is independently selected from $C_2$–$C_{10}$ alkenyl and $C_2$–$C_{10}$ alkynyl;

preferably $C_{2-6}$ alkenyl and $C_{2-6}$ alkynyl, more preferably $C_{2-4}$ alkenyl, and $C_{2-4}$ alkynyl;

even more preferably $C_2$–$C_3$ alkenyl and $C_2$–$C_3$ alkynyl;

wherein $R^{11}$ is independently selected from $C(O)R^{10}$, $COOR^{10}$, $C(O)NR^{10}R^{10}$ and $S(O)_nR^{10}$;

wherein $R^{12}$ is independently selected from H, $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, $C_1$–$C_{10}$ alkyl substituted with 1–3 substituents independently selected from $C_2$–$C_{10}$ alkenyl, $C_2$–$C_{10}$ alkynyl, $C_3$–$C_{10}$ cycloalkyl, $C_4$–$C_{10}$ cycloalkenyl, halo, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$, and $OC(O)R^{13}$, and phenyl optionally substituted with 1–3 substituents independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, halo, $OR^{13}$, $SR^{13}$, $NR^{13}R^{13}$, $COOR^{13}$, $NO_2N$, $C(O)R^{13}$, $C(O)NR^{13}R^{13}$, $NR^{13}C(O)R^{13}$ and $OC(O)R^{13}$, preferably H, $C_{1-6}$ alkyl, $C_{2-6}$ alkenyl, $C_{2-6}$ alkynyl, $C_{3-6}$ cycloalkyl, $C_{4-6}$ cycloalkenyl, $C_1$–$C_6$ alkyl substituted with 1–3 substituents independently selected from $C_{2-6}$ alkenyl, $C_{2-6}$ alkynyl, $C_{3-6}$ cycloalkyl, $C_{4-6}$ cycloalkenyl, halo, $OR^3$, $NR^3R^{13}$, $COOR^{13}$, $NO_2$, CN, $C(O)R^{13}$, $C(O)NR^{13}R^{13}$, $NR^{13}C(O)R^{13}$, and $OC(O)R^{13}$, and phenyl optionally substituted with 1–3 substituents independently selected from $C_{1-6}$ alkyl, $C_{2-6}$ alkenyl, $C_{2-6}$ alkynyl, $C_{3-6}$ cycloalkyl, halo, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$, and $OC(O)R^{13}$, more preferably H, $C_{1-3}$ alkyl, $C_{3-3}$ cycloalkyl, $C_1$–$C_3$ alkyl substituted with 1–3 substituents independently selected from $C_{2-3}$ alkenyl, $C_{2-3}$ alkynyl, $C_{3-6}$ cycloalkyl, fluoro, chloro, $OR^{13}NR^{13}R^{13}$, $COOR^{13}$, $NO_2$, CN, $C(O)R^{13}$, $C(O)NR^{13}R^{13}$, $NR^{13}C(O)R^3$, and $OC(O)R^{13}$, and phenyl optionally substituted with 1–3 substituents independently selected from $C_{1-3}$ alkyl, $C_{3-6}$ cycloalkyl, fluoro, chloro, $OR^3$, $NR^{13}R^{13}$, $COOR^{13}$, $NO_2$, CN, $C(O)R^{13}$, $C(O)NR^{13}R^{13}$, $NR^{13}C(O)R^{13}$, and $OC(O)R^{13}$;

wherein $R^{13}$ is independently selected from H, $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, $C_1$–$C_{10}$ alkyl optionally substituted with halo, $OR^{14}$, $SR^{14}$, $NR^{14}R^{14}$, $COOR^{14}$, $NO_2$, CN, and phenyl optionally substituted with halo, $CF_3$, $OR^{14}$, $SR^{14}$, $NR^{14}R^{14}$, $COOR^{14}$, $NO_2$, and CN, preferably H, $C_{1-6}$ alkyl, $C_{2-6}$ alkenyl, $C_{2-6}$ alkynyl, $C_{3-6}$ cycloalkyl, $C_{4-6}$ cycloalkenyl, $C_1$–$C_6$ alkyl optionally substituted with halo, $CF_3$, $OR^{14}$, $SR^{14}$, $NR^{14}R^{14}$, $COOR^{14}$, $NO_2$, and CN, and phenyl optionally substituted with halo, $OR^{14}$, $SR^{14}$, $NR^{14}R^4$, $COOR^{14}$, $NO_2$, and CN, more preferably H, $C_{1-3}$ alkyl, $C_{3-6}$ cycloalkyl, $C_1$–$C_3$ alkyl optionally substituted with fluoro, chloro, $OR^{14}$, $NR^{14}R^{14}$, $COOR^{14}$, $NO_2$, and CN, and phenyl optionally substituted with fluoro, chloro, $OR^{14}$, $NR^{14}R^{14}$, $COOR^{14}$, $NO_2$ and ON;

wherein $R^{14}$ is independently selected from H, $C_1$–$C_{10}$ alkyl, $C_3$–$C_{10}$ cycloalkyl and phenyl, preferably H, $C_{1-6}$ alkyl, $C_3$–$C_6$ cycloalkyl and optionally substituted phenyl, more preferably H, $C_{1-3}$ alkyl, $C_3$–$C_6$ cycloalkyl and phenyl, and even more preferably H, methyl and ethyl;

wherein $R^{16}$ is independently selected from H, $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, aryl, $R^8$, halo, haloalkyl, $COOR^5$, $O(O)R^5$, $C(O)NR^5R^5$, $S(O)_nR^5$, $S(O)_nNR^5R^5$, $C_1$–$C_{10}$ alkyl substituted with 1–3 substituents independently selected from $R^7$, $R^9$ and aryl, and $C_2$–$C_{10}$ alkenyl substituted with 1–3 substituents independently selected from $R^7$, $R^9$ and aryl, preferably H, $C_{1-6}$ alkyl, $C_{2-6}$ alkenyl, $C_{2-6}$ alkynyl, $C_{3-6}$ cycloalkyl, $C_{4-6}$ cycloalkenyl, optionally substituted phenyl, $R^8$, halo, $C_1$–$C_6$ haloalkyl, $COOR^5$, $C(O)R^5$, $C(O)NR^5R^5$, $S(O)_nR^5$, $S(O)_nNR^5R^5$, $C_1$–$C_6$ alkyl substituted with 1–3 substituents independently selected from $R^7$, $R^9$ and optionally substituted phenyl, and $C_2$–$C_6$ alkenyl substituted with 1–3 substituents independently selected from $R^7$, $R^9$ and optionally substituted phenyl; and wherein n is independently 1 or 2, and preferably n is 2;

wherein aryl is independently a 6-carbon monocyclic, 10-carbon bicyclic or 14-carbon tricyclic aromatic ring system optionally substituted with 1–3 substituents independently selected from $C_1$–$C_{10}$ alkyl, $C_2$–$C_{10}$ alkenyl, $C_2$–$C_{10}$ alkynyl, $C_3$–$C_{10}$ cycloalkyl, $C_4$–$C_{10}$ cycloalkenyl, $R^9$, halo, haloalkyl, $CF_3$, $OR^{10}$, $SR^{10}$, $NR^{10}R$, $NR^{10}R^{10}$, $COOR^{10}$, $NO_2$, CN, $C(O)R^{10}$, $C(O)C(O)R^{10}$, $C(O)NR^5R^5$, $N(R^{10})C(O)NR^{10}R^{10}$, $N(R^{10})C(O)R^{10}$, $N(R^{10})S(O)_nR^{10}$, $N(R^{10})(COOR^{10})$, $NR^{10}C(O)C(O)R^{10}$, $NR^{10}C(O)R^9$, $NR^{10}S(O)_nNR^{10}R^{10}$, $NR^{10}S(O)$ $_nR^9$, $NR^{12}C(O)C(O)NR^{12}R^{12}$, $S(O)_nR^{10}$, $S(O)_nNR^{10}R^{10}$, $OC(O)R^{10}$, $C_1$–$C_{10}$ alkyl substituted with 1–3 substituents independently selected from $R^9$, halo, $CF_3$, $OR^{10}$, $SR^{10}$, $OC(O)R^{10}$, $NR^{11}R^{11}$, $NR^{10}R^{10}$, $NR^{10}R^{11}$, $COOR^{10}$, $NO_2$, CN, $C(O)R^{10}$, $OC(O)NR^{10}R^{10}$, $C(O)NR^5R^5$, $N(R^{10})C(O)R^{10}$, $N(R^{10})(COOR^{10})$, $S(O)_nNR^{10}R^{10}$; $R^{10}$; and $C_2$–$C_{10}$ alkenyl substituted with 1–3 substituents independently selected from $R^9$, halo, $CF_3$, $OR^{10}$, $SR^{10}$, $C(O)R^{10}$, $NR^{11}R^{11}$, $NR^{10}R^{10}$, $NR^{10}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$ and $S(O)_nNR^{10}R^{10}$, preferably optionally substituted with 1–3 substituents independently selected from $C_1$–$C_6$ alkyl, $C_2$–$C_6$ alkenyl, $C_2$–$C_6$ alkynyl, $C_3$–$C_6$ cycloalkyl, $C_4$–$C_6$ cycloalkenyl, $R^9$, halo, haloalkyl, $CF_3$, $OR^{10}$, $SR^{10}$, $NR^{10}R$, $NR^{10}R^{11}$, $COOR^{10}$, $NO_2$, CN, $C(O)R^{10}$, $C(O)C(O)R^{10}$, $C(O)NR^5R^5$, $N(R^{10})C(O)NR^{10}R^{10}$, $N(R^{10})C(O)R^{10}$, $N(R^{10})S(O)_nR^{10}$, $N(R^{10})(COOR^{10})$, $NR^{10}C(O)C(O)R^{10}$, $NR^{10}C(O)R^9$, $NR^{10}S(O)_nNR^{10}R^{10}$, $NR^{10}S(O)_nR^9$, $NR^{12}C(O)C(O)NR^{12}R^{12}$, $S(O)_nR^{10}$, $S(O)_nNR^{10}R^{10}$, $OC(O)R^{10}$, $C_1$–$C_6$ alkyl substituted with 1–3 substituents independently selected from $R^9$, halo, $CF_3$, $OR^{10}$, $SR^{10}$, $OC(O)R^{10}$, $NR^{11}R^{11}$, $NR^{10}R^{10}$, $NR^{10}R^{11}$, $COOR^{10}$, $NO_2$, CN, $C(O)R^{10}$, $OC(O)NR^{10}R^{10}$, $C(O)NR^5R^5$, $N(R^{10})C(O)R^{10}$, $N(R^{10})(COOR^{10})$, $S(O)_nNR^{10}R^{10}$, $R^{10}$, and $C_2$–$C_6$ alkenyl substituted with 1–3 substituents independently selected from $R^9$, halo, $CF_3$, $OR^{10}$, $SR^{10}$, $OC(O)R^{10}$, $NR^{11}R^{11}$, $NR^{10}R^{10}$, $NR^{10}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$ and $S(O)_nNR^{10}R^{10}$, more preferably optionally substituted with 1–3 substituents independently selected from $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, $R^9$, fluoro, chloro, $C_1$–$C_3$ haloalkyl, $OR^{10}$, $NR^{10}R$, $NR^{10}R^{11}$, $COOR^{10}$, $NO_2$, CN, $C(O)R^{10}$, $C(O)NR^{10}R^{10}$, $N(R^{10})C(O)NR^{10}R^{10}$, $N(R^{10})C(O)R^{10}$, $N(R^{10})SO_2R^{10}$, $N(R^{10})(COOR^{10})$, $NR^{10}C(O)R^9$, $NR^{10}SO_2NR^{10}R^{10}$, $NR^{10}SO_2R^9$, $SO_2R^{10}$, $SO_2NR^{10}R^{10}$, $OC(O)R^{10}$, and $C_1$–$C_3$ alkyl substituted with 1–2 substituents independently selected from $R^9$, $OR^{10}$, $OC(O)R^{10}$, $NR^{11}R^{11}$, $NR^{10}R$, $NR^{10}R^{11}$, $COOR^{10}$, $NO_2$, CN, C(O)R, $OC(O)NR^{10}R^{10}$, $C(O)NR^5R^5$, $N(R^{10})C(O)R^{10}$, $N(R^{10})(COOR^{10})$, $SO_2NR^{10}R^{10}$, and $R^{10}$, even more preferably optionally substituted with 1–3 substituents independently selected from $C_1$–$C_3$ alkyl, $R^9$, fluoro, chloro, $C_1$–$C_3$ haloalkyl, $OR^{10}$, $NR^{10}R^{10}$, $COOR^{10}C(O)R^{10}$, $C(O)NR^5R^5$, $OC(O)R^{10}$, and $C_1$–$C_3$ alkyl substituted with 1–2 substituents independently selected from phenyl and $R^9$, and of particular interest where optionally substituted with 1–3 substituents independently selected from methyl, phenyl, pyridyl, fluoro, chloro, $CF_3$, hydroxy, methoxy, acetyl, amino, methylamino, dimethylamino, carboxy, methoxycarbonyl, methylcarbonyl, aminocarbonyl, and $C_1$–$C_3$ alkyl substituted with optionally substituted phenyl or optionally substituted 5–6 membered heterocyclyl;

and pharmaceutically acceptable isomers and salts thereof.

The invention also relates to compounds of Formula II

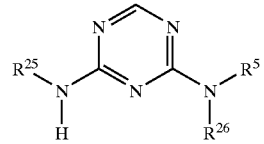

II wherein $R^5$ is selected from H and $C_{1-4}$ alkyl,
preferably H, methyl and ethyl, and
more preferably H or methyl;
wherein $R^{26}$ is selected from 5–10 membered heterocyclyl, phenyl and $C_{3-6}$ cycloalkyl,
preferably indazolyl, benzopyrrolyl, phenyl and cyclopropyl, and
wherein $R^{26}$ is optionally substituted with 1–2 substituents independently selected from phenyl, benzyloxy, chloro, fluoro, benzyl and 2-pyridylmethylenenyl;
or wherein $R^5$ and $R^{26}$ together form a nitrogen containing 5–10-membered heterocyclic ring,
preferably a heterocyclic ring selected from pyrrolidinyl, morpholinyl, piperdinyl, piperazinyl, tetrahydroisoquinolinyl and tetrahydroquinolinyl, and
more preferably a heterocyclic ring selected from morpholinyl, piperdinyl, piperazinyl, tetrahydroisoquinolinyl and tetrahydroquinolinyl;
wherein $R^{25}$ is selected from phenyl, and 5–10 membered heterocyclyl; wherein $R^{25}$ is substituted with —NC(O)$R^{10a}$,
preferably selected from phenyl, pyridyl, indazolyl, benzimidazolyl, benzopyrrolyl, dihydrobenzopyrrolyl, and quinolyl, and
wherein $R^{25}$ is substituted with —NC(O)$R^{10}$;
wherein $R^{10a}$ is selected from $C_2$–$C_6$ alkenyl and $C_2$–$C_6$ alkynyl,
preferably $C_2$–$C_4$ alkenyl and $C_2$–$C_4$ alkynyl, and
more preferably ethenyl and $C_2$–$C_3$ alkynyl;
wherein $R^{28}$ is selected from H, $C_{1-4}$ alkyl, phenyl, and 5–6-membered heterocyclyl; and
preferably H, methyl, ethyl and phenyl;
wherein heterocyclyl is optionally substituted with one or more substituents selected from H, $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{28}$, —$OC(O)R^2$, —$NR^{28}R^{28}$, —$COOR^2$, —$C(O)R^{21}$, —$C(O)NR^{28}R^{28}$, —$SO_2R^{28}$, —$SO_2NR^{28}R^{28}$, —$NR^{28}C(O)NR^{28}R^{28}$, —$NR^{28}C(O)R^2$, —$NR^{28}(COOR^{28})$, —$NR^{28}SO_2NR^{28}R^{28}$, —$NR^{28}SO_2R^{28}$, —$OC(O)NR^{28}R^{28}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl, and
preferably $C_1$–$C_3$ alkyl, $C_2$–$C_3$ alkenyl, $C_3$–$C_6$ cycloalkyl, phenyl, 5–6 membered heterocyclyl, fluoro, chloro, $CF_3$, —$OR^{28}$, —$OC(O)R$, —$NR^{28}R^{28}$, —$COOR^{28}$, —$C(O)R^{28}$, —$C(O)NR^{28}R^{28}$, $C_1$–$C_3$ alkyl substituted with optionally substituted phenyl or optionally substituted 5–6 membered heterocyclyl;

wherein phenyl is optionally substituted with one or more substituents selected from H, $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{28}$, —$OC(O)R^{28}$, —$NR^{28}R^{28}$, —$COOR^2$, $C(O)R^{28}$, $C(O)NR^2R^{28}$, —$SO_2R^{28}$, —$SO_2NR^{28}R^{28}$, —$NR^{28}C(O)$ $NR^{28}R^{28}$, $NR^{28}C(O)R^2$, —$NR^{28}(COOR^{28})$, —$NR^{28}SO_2NR^{28}R^{28}$, —$NR^{28}SO_2R^{28}$, —$OC(O)$ $NR^{28}R^{28}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl, and preferably methyl, phenyl, pyridyl, fluoro, chloro, $CF_3$, hydroxy, methoxy, acetyl, amino, methylamino, dimethylamino, —$CO_2H$, methoxycarbonyl, methylcarbonyl, aminocarbonyl, and $C_1$–$C_3$ alkyl substituted with optionally substituted phenyl or optionally substituted 5–6 membered heteroaryl;

wherein cycloalkyl is optionally substituted with one or more substituents selected from H, $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OC(O)R^{28}$, —$NR^{28}R^{28}$, —$COOR^2$, —$C(O)R^{28}$, —$C(O)NR^{28}R^{28}$, —$SO_2R^{28}$, —$SO_2NR^{28}R^{28}$, —$NR^{28}C(O)NR^{28}R^{28}$, —$NR^{28}C(O)R^2$, —$NR^{28}(COOR^{28})$, —$NR^{28}SO_2NR^{28}R^{28}$, —$NR^{28}SO_2R^{28}$, —$OC(O)NR^{28}R^{28}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl; and preferably methyl, phenyl, pyridyl, fluoro, chloro, $CF_3$, hydroxy, methoxy, acetyl, amino, methylamino, dimethylamino, —$CO_2H$, methoxycarbonyl, methylcarbonyl, aminocarbonyl, and $C_1$–$C_3$ alkyl substituted with optionally substituted phenyl or optionally substituted 5–6 membered heteroaryl;

and pharmaceutically acceptable isomers and salts thereof. The invention also relates to compounds of Formula III

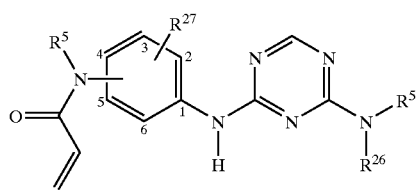

III wherein $R^5$ is selected from H, $C_{1-4}$ alkyl and $C_{1-4}$ alkyl substituted with 5–10 membered heterocyclyl, and preferably H, methyl and $C_{1-3}$ alkyl substituted with optionally substituted morpholinyl, optionally substituted piperdinyl and optionally substituted piperazinyl;

wherein $R^{26}$ is selected from 5–10 membered heterocyclyl, phenyl and $C_{3-6}$ cycloalkyl, preferably optionally substituted indazolyl, optionally substituted benzopyrrolyl, optionally substituted phenyl and optionally substituted cyclopropyl;

more preferably optionally substituted indazolyl, optionally substituted benzopyrrolyl, and optionally substituted phenyl;

or wherein $R^5$ and $R^{26}$ together form a nitrogen containing 5–10-membered heterocyclic ring, preferably an optionally substituted heterocyclic ring selected from pyrrolidinyl, morpholinyl, piperdinyl, piperazinyl, tetrahydroisoquinolinyl and tetrahydroquinolinyl, and more preferably morpholinyl, piperdinyl, piperazinyl, tetrahydroisoquinolinyl and tetrahydroquinolinyl;

wherein $R^{27}$ is selected from H, $C_{1-4}$ alkyl, fluoro, chloro, $NO_2$, CN, $CF_3$, $C_2$–$C_3$ alkenyl, $C_2$–$C_3$ alkynyl, —$OR^{28}$, —$OC(O)R^{28}$, —$NR^{28}R^{28}$, —$COOR^2$, —$C(O)R^{28}$, —$C(O)$ $NR^{28}R^{28}$, —$SO_2R^{28}$, $SO_2NR^{28}R^{28}$, —$NR^{28}CO(O)$ $NR^{28}R^{28}$, —$NR^{28}C(O)R^{28}$, —$NR^{28}(COOR^{28})$, —$NR^{28}SO_2NR^{28}R^{28}$, —$NR^{28}SO_2R^{28}$, —$OC(O)NR^{28}R^{28}$, $C_3$–$C_6$ cycloalkyl, $C_4$–$C_6$ cycloalkenyl, phenyl, 5–6 membered heterocyclyl, $C_{1-4}$ alkoxy, phenyloxy, 5–10 membered heterocyclyloxy $C_{1-4}$ haloalkyl, phenyl-$C_1$–$C_4$ alkyl, phenyl-$C_{1-4}$ alkoxy, 5–10 membered heterocyclyl-$C_{1-4}$ alkyl, and 5–10 membered heterocyclyl-$C_{1-4}$ alkoxy, preferably H, $C_{1-4}$ alkyl, fluoro, chloro, CN, $CF_3$, —$OR^{28}$, —$OC(O)R^{28}$, —$NR^{28}R^{28}$, —$COOR^2$, —$C(O)R^{28}$, —$C(O)NR^{28}R^{28}$, —$SO_2R^{28}$, —$SO_2NR^{28}R^{28}$, phenyl, 5–6 membered heterocyclyl, $C_{1-4}$ haloalkyl, phenyl-$C_{1-4}$ alkyl, phenyl-$C_{1-4}$ alkoxy, 5–10 membered heterocyclyl-$C_{1-4}$ alkyl, and 5–10 membered heterocyclyl-$C_{1-4}$ alkoxy, and more preferably H, methyl, fluoro, chloro, methoxy, phenylpropoxy, 1-methylpiperazinylpropoxy, morpholinylpropoxy and 1-methylpiperidinylpropoxy;

wherein $R^{28}$ is selected from H, $C_{1-4}$ alkyl, phenyl, and 5-6-membered heterocyclyl, preferably H, methyl, ethyl and optionally substituted phenyl;

wherein heterocyclyl is optionally substituted with one or more substituents selected from H, $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —OR , —$OC(O)R^{28}$, —$NR^{28}R^{28}$, —$COOR^2$, —$C(O)R^{28}$, —$C(O)NR^{28}R^{28}$, —$SO_{28}R^{28}$, —$SO_2NR^{28}R^{28}$, —$NR^{28}C(O)NR^{28}R^{28}$, —$NR^{28}C(O)R^2$, —$NR^{28}(COOR^{28})$, —$NR^{28}SO_2NR^{28}R^{28}$, —$NR^{28}SO_2R^{28}$, —$OC(O)NR^{28}R^{28}$, and $C_1$–$C_3$ alkyl substituted with 1–3 substituents independently selected from optionally substituted phenyl and optionally substituted 5–6 membered heterocyclyl, preferably $C_1$–$C_3$ alkyl, $C_2$–$C_3$ alkenyl, $C_3$–$C_6$ cycloalkyl, phenyl, 5–6 membered heterocyclyl, fluoro, chloro, $CF_3$, —$OR^{28}$, —$OC(O)R^{28}$, —$NR^{28}R^{28}$, —$COOR^{28}$, —$C(O)R^{28}$—$C(O)NR^{28}R^{28}$, $C_1$–$C_3$ alkyl substituted with optionally substituted phenyl or optionally substituted 5–6 membered heterocyclyl, and more preferably $C_1$–$C_3$ alkyl, $C_3$–$C_6$ cycloalkyl, phenyl, fluoro, chloro, —$OR^{28}$, $CF_3$, —$OC(O)$ $R^{28}R^{28}$, —$NR^{28}R^{28}$, —$COOR^{28}$, —$C(O)R^{28}$, —$C(O)NR^{28}R^{28}$, and $C_1$–$C_3$ alkyl substituted with optionally substituted phenyl or optionally substituted 5–6 membered heterocyclyl;

wherein phenyl is optionally substituted with one or more substituents selected from H, $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{28}$, —$OC(O)R^{28}R^{28}$, —$NR^{28}R^{28}$, —$COOR^2$, —$C(O)R^{28}$, —$C(O)NR^{28}R^{28}$, —$SO_2R^{28}$, —$SO_2NR^{28}R^{28}$, —$NR^{28}C(O)NR^{28}R^{28}$, —$NR^{28}C(O)R^2$, —$NR^{28}(COOR^{28})$, —$NR^{28}SO_2NR^{28}R^{28}$, —$NR^{28}SO_2R^{28}$, —$OC(O)NR^{28}R^{28}$, and $C_1$–$C_3$ alkyl substituted with 1–3 substituents independently selected from optionally substituted phenyl and optionally substituted 5–6 membered heterocyclyl, preferably $C_1$–$C_3$ alkyl, $C_2$–$C_3$ alkenyl, $C_3$–$C_6$ cycloalkyl, phenyl, 5–6 membered heterocyclyl, fluoro, chloro, $CF_3$, —$OR^{28}$, —$OC(O)R^{28}$, —$NR^{28}R^{28}$, —$COOR^{28}$, —$C(O)R^{28}$, —$C(O)NR^{28}R^{28}$, $C_1$–$C_3$ alkyl substituted with optionally substituted phenyl or optionally substituted 5–6 membered heterocyclyl, and more preferably substituted with $C_1$–$C_3$ alkyl, 5–6 membered heterocyclyl, fluoro, chloro, $CF_3$, —$OR^{28}$, —$OC(O)R^{28}$, —$NR^{28}R^{28}$, —$COOR^{28}$, —$C(O)R^{28}$, —$C(O)NR^{28}R^{28}$, and $C_1$–$C_3$ alkyl substituted with optionally substituted phenyl or optionally substituted 5–6 membered heterocyclyl;

wherein cycloalkyl is optionally substituted with one or more substituents selected from H, $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{28}$, —$OC(O)R^{28}$, —$NR^{28}R^{28}$, —$COOR^2$, —$C(O)R^{28}$, —$C(O)NR^{28}R^{28}$, —$SO_2R^{28}$, —$SO_2NR^{28}R^{28}$, —$NR^{28}C(O)NR^{28}R^{28}$, —$NR^{28}C(O)R^2$, —$NR^{28}(COOR^{28})$, —$NR^{28}SO_2NR^{28}R^{28}$, —$NR^{28}SO_2R^{28}$, —$OC(O)NR^{28}R^{28}$, and $C_1$–$C_3$ alkyl substituted with 1–3 substituents independently selected from optionally substituted phenyl and optionally substituted 5–6 membered heterocyclyl, preferably $C_1$–$C_3$ alkyl, $C_2$–$C_3$ alkenyl, $C_3$–$C_6$ cycloalkyl, phenyl, 5–6 membered heterocyclyl, fluoro, chloro, $CF_3$, —$OR^{28}$, —$OC(O)R^{28}$, —$NR^{28}R^{28}$, —$COOR^{28}$, —$C(O)R^{28}$, —$C(O)NR^{28}R^{28}$, $C_1$–$C_3$ alkyl substituted with optionally substituted phenyl or optionally substituted 5–6 membered heterocyclyl, and more preferably substituted with optionally substituted phenyl;

preferably the acrylamide group is attached at position 3 or 4;

and pharmaceutically acceptable salts thereof.

A family of specific compounds of particular interest within Formula I consists of compounds and pharmaceutically-acceptable salts thereof as follows:

N-{3-[4-(3,4,5-trimethoxy-phenylamino)-[1,3,5]triazin-2-ylamino]-phenyl}-acrylamide,
N-{4-[4-(3,4,5-trimethoxy-phenylamino)-[1,3,5]triazin-2-ylamino]-phenyl}-acrylamide,
N-(3-{4-[(1-benzyl-1H-indazol-5-yl)-methyl-amino]-[1,3,5]triazin-2-ylamino}-phenyl)-acrylamide,
N-{4-[4-(1-benzyl-1H-indazol-5-ylamino)-[1,3,5]triazin-2-ylamino]-phenyl}-acrylamide,
N-(4-{4-[(1-benzyl-1H-indazol-5-yl)-methyl-amino]-[1,3,5]triazin-2-ylamino}-phenyl)-acrylamide,
N-{3-[4-(1-benzyl-1H-indazol-5-ylamino)-[1,3,5]triazin-2-ylamino]-phenyl}-acrylamide,
N-{3-[4-(1-pyridin-2-ylmethyl-1H-indazol-5-ylamino)-[1,3,5]triazin-2-ylamino]-phenyl}-acrylamide,
N-{3-[4-(3-chloro-phenylamino)-[1,3,5]triazin-2-ylamino]-phenyl}-acrylamide,
N-(3-{4-[(3-chloro-phenyl)-methyl-amino]-[1,3,5]triazin-2-ylamino}-phenyl)-acrylamide,
N-{3-[4-(7-chloro-3,4-dihydro-2H-quinolin-1-yl)-[1,3,5]triazin-2-ylamino]-phenyl}-acrylamide,
N-{3-[4-(2-phenyl-cyclopropylamino)-[1,3,5]triazin-2-ylamino]-phenyl}-acrylamide,
N-{5-[4-(1-benzyl-1H-indazol-5-ylamino)-[1,3,5]triazin-2-ylamino]-2-methoxy-phenyl}-acrylamide,
N-(5-{4-[(1-benzyl-1H-indazol-5-yl)-methyl-amino]-[1,3,5]triazin-2-ylamino}-2-methoxy-phenyl)-acrylamide,
1-{6-[4-(3-chloro-phenylamino)-[1,3,5]triazin-2-ylamino]-2,3-dihydro-indol-1-yl}-propenone (38),
1-{5-[4-(3-chloro-phenylamino)-[1,3,5]triazin-2-ylamino]-2,3-dihydro-indol-1-yl}-propenone,
1-{6-[4-(1-benzyl-1H-indazol-5-ylamino)-[1,3,5]triazin-2-ylamino]-2,3-dihydro-indol-1-yl}-propenone,
1-{5-[4-(1-benzyl-1H-indazol-5-ylamino)-[1,3,5]triazin-2-ylamino]-2,3-dihydro-indol-1-yl}-propenone,
1-{6-[4-(3-chloro-phenylamino)-[1,3,5]triazin-2-ylamino]-indazol-1-yl}-propenone,
1-{5-[4-(3-chloro-phenylamino)-[1,3,5]triazin-2-ylamino]-indazol-1-yl}-propenone,
1-{6-[4-(1-benzyl-1H-indazol-5-ylamino)-[1,3,5]triazin-2-ylamino]-indazol-1-yl}-propenone,
1-{5-[4-(1-benzyl-1H-indazol-5-ylamino)-[1,3,5]triazin-2-ylamino]-indazol-1-yl}-propenone,
N-[5-[4-(3-chloro-phenylamino)-[1,3,5]triazin-2-ylamino]-2-(3-morpholin-4-yl-propoxy)-phenyl]-acrylamide,
N-[5-[4-(1-benzyl-1H-indazol-5-ylamino)-[1,3,5]triazin-2-ylamino]-2-(3-morpholin-4-yl-propoxy)-phenyl]-acrylamide,
N-[5-{4-[(1-benzyl-1H-indazol-5-yl)-methyl-amino]-[1,3,5]triazin-2-ylamino}-2-(3-morpholin-4-yl-propoxy)-phenyl]-acrylamide,
N-[5-[4-(7-chloro-3,4-dihydro-2H-quinolin-1-yl)-[1,3,5]triazin-2-ylamino]-2-(3-morpholin-4-yl-propoxy)-phenyl]-acrylamide,
N-[5-{4-[(3-chloro-phenyl)-methyl-amino]-[1,3,5]triazin-2-ylamino}-2-(3-morpholin-4-yl-propoxy)-phenyl]-acrylamide,
N-{5-{4-[(3-chloro-phenyl)-methyl-amino]-[1,3,5]triazin-2-ylamino}-2-[3-(4-methyl-piperazin-1-yl)-propoxy]-phenyl}-acrylamide,
N-{5-[4-(3-chloro-phenylamino)-[1,3,5]triazin-2-ylamino]-2-[3-(4-methyl-piperazin-1-yl)-propoxy]-phenyl}-acrylamide,
N-{5-[4-(1-benzyl-1H-indazol-5-ylamino)-[1,3,5]triazin-2-ylamino]-2-[3-(4-methyl-piperazin-1-yl)-propoxy]-phenyl}-acrylamide,
N-{5-{4-[(1-benzyl-1H-indazol-5-yl)-methyl-amino]-[1,3,5]triazin-2-ylamino}-2-[3-(4-methyl-piperazin-1-yl)-propoxy]-phenyl}-acrylamide,
N-{5-{4-[(7-chloro-3,4-dihydro-2H-quinolin-1-yl)-[1,3,5]triazin-2-ylamino]-2-[3-(4-methyl-piperazin-1-yl)-propoxy]-phenyl}-acrylamide,
N-(3-{4-[(4-benzyloxy-phenyl)-methyl-amino]-[1,3,5]triazin-2-ylamino}-phenyl)-acrylamide,
N-{3-[4-(4-benzyloxy-phenylamino)-[1,3,5]triazin-2-ylamino]-phenyl}-acrylamide,
N-{3-[4-(1-benzyl-1H-indol-5-ylamino)-[1,3,5]triazin-2-ylamino]-phenyl}-acrylamide,
N-(3-{4-[(1-benzyl-1H-indol-5-yl)-methyl-amino]-[1,3,5]triazin-2-ylamino}-phenyl)-acrylamide,
N-(3-{4-[(4-benzyloxy-3-chloro-phenyl)-methyl-amino]-[1,3,5]triazin-2-ylamino}-phenyl)-acrylamide,
N-{3-[4-(4-benzyloxy-3-chloro-phenylamino)-[1,3,5]triazin-2-ylamino]-phenyl}-acrylamide,
N-[5-[4-(1-benzyl-1H-indol-5-ylamino)-[1,3,5]triazin-2-ylamino]-2-(3-morpholin-4-yl-propoxy)-phenyl]-acrylamide,
N-[5-{4-[(1-benzyl-1H-indol-5-yl)-methyl-amino]-[1,3,5]triazin-2-ylamino}-2-(3-morpholin-4-yl-propoxy)-phenyl]-acrylamide,
N-[5-{4-[(4-benzyloxy-3-chloro-phenyl)-methyl-amino]-[1,3,5]triazin-2-ylamino}-2-(3-morpholin-4-yl-propoxy)-phenyl]-acrylamide,
N-[5-[4-(4-benzyloxy-3-chloro-phenylamino)-[1,3,5]triazin-2-ylamino]-2-(3-morpholin-4-yl-propoxy)-phenyl]-acrylamide,
but-2-ynoic acid (3-{4-[(3-chloro-phenyl)-methyl-amino]-[1,3,5]triazin-2-ylamino}-phenyl)-amide, but-2-ynoic acid {3-[4-(3-chloro-phenylamino)-[1,3,5]
triazin-2-ylamino]-phenyl)-amide,
but-2-ynoic acid {3-[4-(1-benzyl-1H-indazol-5-ylamino)-
[1,3,5]triazin-2-ylamino]-phenyl}-amide,
but-2-ynoic acid (3-{4-[(1-benzyl-1H-indazol-5-yl)-methyl-
amino]-[1,3,5]triazin-2-ylamino}-phenyl)-amide, and
but-2-ynoic acid {3-[4-(7-chloro-3,4-dihydro-2H-quinolin-
1-yl)-[1,3,5]triazin-2-ylamino]-phenyl)-amide.

Indications

Compounds of the present invention would be useful for, but not limited to, the prevention or treatment of angiogenesis related diseases. The compounds of the invention have kinase inhibitory activity, such as her1 and/or her2 inhibitory activity. The compounds of the invention are useful in therapy as antineoplasia agents.

Compounds of the invention are useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (eq., anticancer) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (eq., psoriasis) and benign hyperplasia of the prostate (eg., BPH). It is, in addition, expected that a compound of the present invention may possess activity against a range of leukemias and lymphoid malignancies.

The compounds of the present invention are also useful in the treatment of polycystic kidney disease and diabetic conditions such as glaucoma, diabetic retinopathy and microangiopathy.

The compounds of this invention may also act as inhibitors of other protein kinases, e.g. ErbB, KDR, CDK-2, CDK-5, IKK, JNK3, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

The term "treatment" includes therapeutic treatment as well as prophylactic treatment (either preventing the onset of disorders altogether or delaying the onset of a preclinically evident stage of disorders in individuals).

The term "prevention" includes either preventing the onset of disorders altogether or delaying the onset of a preclinically evident stage of disorders in individuals. This includes prophylactic treatment of those at risk of developing a disease, such as a cancer, for example. "Prophylaxis" is another term for prevention.

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by being therapeutically effective in vivo.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino.

The term "heterocyclyl" embraces saturated, partially saturated and unsaturated heteroatom-containing ring-shaped radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —$SO_2$—.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "alkylamino" embraces "N-alkylamino" and "N,N-dialkylamino" where amino groups are substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino or the like.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$–$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The present invention preferably includes compounds that selectively inhibit EGF.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of her1 and/or her2.

The present invention comprises a pharmaceutical composition comprising a therapeutically-effective amount of a compound of Formulas I-III in association with a least one pharmaceutically-acceptable carrier, adjuvant or diluent.

The present invention also comprises a method of treating her1 and/or her2 related disorders, such as cancer or polycystic kidney disease in a subject, the method comprising treating the subject having or susceptible to such disorder with a therapeutically-effective amount of a compound of Formulas I–III.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of Formula I may be administered either prior to, at the same time as, or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19–384, Sumimoto DACHP $(Myr)_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-Al, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, u-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston AS, antineoplaston AS2–1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, _ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-la, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucinyttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

When the compositions of this invention comprise a combination of a kinase inhibitor of the Formulass described herein and one or more additional therapeutic or prophylactic agents, both the kinase inhibitor and the additional agent should be present at dosage levels of between about 10 to 100%, and more preferably between about 10 to 80% of the dosage normally administered in a monotherapy regimen. Such additional kinase inhibitory agents were those which may modulate, regulate or otherwise affect kinase enzyme activity. Such effects may lead to modulation of disease pathology and/or symptoms. Kinase inhibitory agents include, for example, small molecules, polypeptides, antibodies (including for example, monoclonals, chimeric, humanized, single chain, immunokines, etc.), and the like. Examples of additonal kinase inhibitory small molecule agents include, but were not limited to, CDK inhibitors and p38 inhibitors, including SU-6668, SU-5416, ZD-4190, ZD-1839, STI-571, CP-358774, LY-333531 and the like.

The pharmaceutical compositions of this invention comprise an additional immunosuppression agent. Examples of additional immunosuppression agents include, but were not limited to, cyclosporin A, FK506, rapamycin, leflunomide, deoxyspergualin, prednisone, azathioprine, mycophenolate mofetil, OKT3, ATAG, interferon and mizoribine.

The pharmaceutical compositions of this invention may additionally comprise antibodies (including for example, monoclonals, chimeric, humanized, single chain, immunokines, etc.), cytotoxic or hormonal anti-cancer agents or combinations thereof.

The pharmaceutical compositions of this invention may additionally comprise an anti-viral agent. Examples of anti-viral agents include, but were not limited to, Cytovene, Ganciclovir, trisodium phosphonoformate, Ribavirin, d4T, ddI, AZT, amprenavir and acyclovir.

The present invention comprises a process for the preparation of a compound of Formulas I–III.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Compounds of the present invention can possess, in general, tautomeric forms, which are included in the family of compounds in Formula I.

Also included in the family of compounds of Formulas I–III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I–III may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are acetic, adipic, algenic, anthranilic, ascorbic, aspartic, benzoic, benzenesulfonic, butyric, camphoric, camphorsulfonic, citric, cyclopentanepropionic, cyclohexylaminosulfonic, digluconic, dodecylsulfonic, ethanesulfonic, formic, fumaric, galactaric, galacturonic, glycolic, gluconic, glucuronic, glucoheptanoic, glutamic, glycerophosphonic, heptanoic, hexanoic, 4-hydroxybenzoic, 2-hydroxyethanesulfonic, β-hydroxybutyric, lactic, malic, 4 maleic, mandelic, mesylic, methanesulfonic, nicotinic, 2-naphthalenesulfonic, oxalic, palmoic, pectinic, pivalic, persulfuric, 2-phenylpropionic, picric, pyruvic, propionic, phenylacetic, embonic (pamoic), cyclopentane proprionic, pantothenic, toluenesulfonic, salicylic, sulfanilic, stearic, succinic, tartaric, thiocyanic, and undecanoic.

Suitable pharmaceutically-acceptable base addition salts of compounds of Formulas I–III include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formulas I–III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66, 1 (1977).

The invention also relates to a method of making a compound of the formulas described herein, comprising synthesizing any one or more intermediates illustrated in the synthetic schemes herein and then converting that intermediate(s) to a compound of the formulas described herein. The invention also relates to a method of making a compound of the formulas described herein, comprising synthesizing any one or more intermediates illustrated in the examples herein and then converting that intermediate(s) to a compound of the formulas described herein.

The invention relates to a process for making a compound of any of the formulas described herein, comprising reacting a triazine of one or more of the formulas:

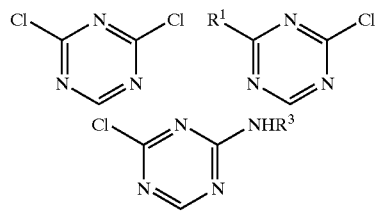

with an appropriate nucleophilic agent or agents, wherein the groups in said formulas are as defined herein.

The invention relates to a process for making a compound of any of the formulas described herein, comprising reacting a triazine of one or more of the formulas:

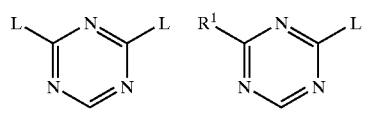

-continued

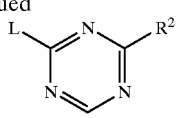

with an appropriate nucleophilic agent or agents, wherein L is defined as a leaving group and the groups in said formulas are as defined herein.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally comprise steps, either before or after the steps described specifically herein, to add or remove suitable protecting groups in order to ultimately allow synthesis of the compound of the formulas described herein.

General Synthetic Procedures

The compounds of the invention can be synthesized according to the following procedures of Schemes 1–9, wherein the substituents are as defined for Formulas I–III, above, except where further noted.

Scheme 1

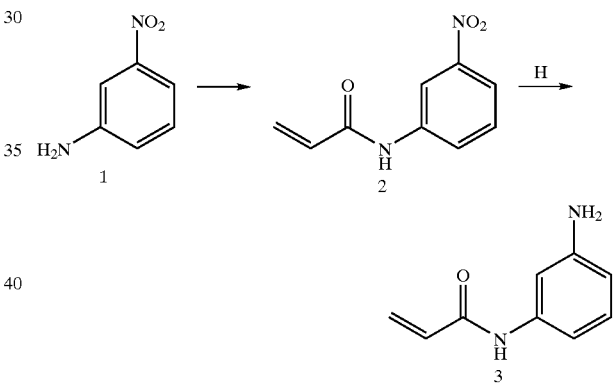

Acrylamide substituted anilines can be prepared according to the method set out in Scheme 1. Acrylic acid is coupled with 3-nitroaniline 1, such as with EDC and HOBT in the presence of base, such as DIEA, to give N-(3-nitrophenyl)acrylamide 2. The acrylamide substituted aniline 3 is prepared by reduction of the corresponding nitro compound 2. The reduction preferably takes place in the presence of a suitable reducing agent, such as tin(II) chloride, iron or hydrogen in the presence of an appropriate catalyst, such as Raney nickel (then preferably the hydrogen is used under pressure, e.g. between 2 and 20 bar) or $PtO_2$, in an appropriate solvent, e.g. an alcohol, such as MeOH. The reaction temperature is preferably between about 0° C. and about 80° C., especially about 15° C. to about 30° C. Alternatively, sodium borohydride can be used.

For example, N-(3-nitrophenyl)acrylamide 2 is reduced in the presence of iron powder, $FeSO_4$ and water, preferably upon heating, more preferably upon heating to reflux. The reaction mixture is cooled to RT and the solution is made basic, such as to a pH>12, preferably to a pH of about 13–14 to give N-(3-aminophenyl)acrylamide 3.

Scheme 2

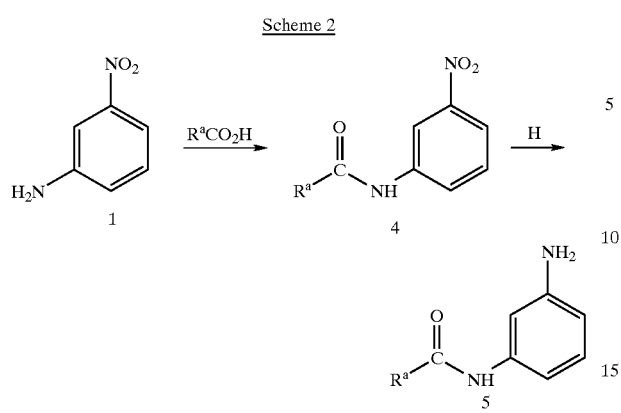

Similarly, other amides 5 (where $R^a$ is alkenyl or alkynyl) can be prepared according to the method set out in Scheme 2. Acids are coupled with 3-nitroaniline 1, such as with EDC and HOBT in the presence of base, such as DIEA, to give amide 4. The amide 5 is prepared by reduction of the corresponding nitro compound 4. The reduction preferably takes place in the presence of a suitable reducing agent, such as tin(II) chloride, iron or hydrogen in the presence of an appropriate catalyst, such as Raney nickel (then preferably the hydrogen is used under pressure, e.g. between 2 and 20 bar) or $PtO_2$, in an appropriate solvent, e.g. an alcohol, such as MeOH. The reaction temperature is preferably between about 0° C. and about 80° C., especially about 15° C. to about 30° C.

Scheme 3

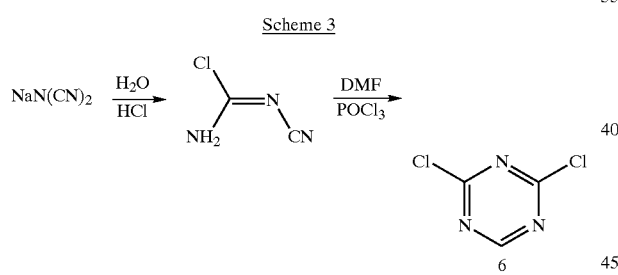

2,4-Dichloro-triazine 6 can be prepared according to the method set out in Scheme 3. Similar to that described by E. Allenstein, *Z. Anorg. Allgem. Chem*, 322, 265 (1963), sodium dicyanamide in water is reacted with concentrated HCl at a temperature of about −18 to about 35° C., to give N-cyanochloroformamidine. N-Cyanochloroformamidine is added to a solution of DMF and $POCl_3$ in a solvent, such as $CH_2Cl_2$, preferably at a temperature at about RT, to give 2,4-dichloro-1,3,5-triazine 6, similar to the method described by R. Harris, *Synthesis*, 11, 907, (1981).

Scheme 4

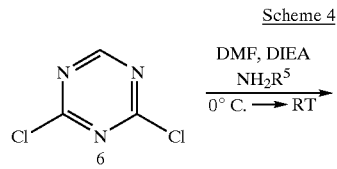

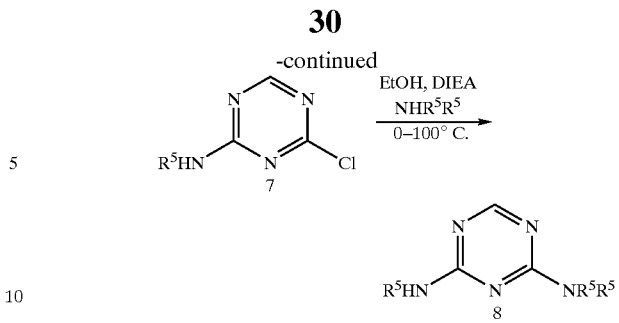

Monoamine substituted triazines 7 and diamine substituted triazines 8 can be prepared according to the method set out in Scheme 4. 2,4-Dichloro-1,3,5-triazine 6 is coupled with amines in the presence of base, such as DIEA, and a solvent, such as DMF, at a temperature of about 0° C. to about RT to give the 4-chloro-[1,3,5]triazin-2-yl)amine 7.

Alternatively, 2,4-dichloro-1,3,5-triazine 6 is coupled with an amine in the presence of $K_2CO_3$, such as suspended in an organic solvent, such as AcCN, to yield triazines 7. Preferably the reaction is held at a temperature below RT, and more preferably at about 0° C.

Monoamine substituted triazines 7 are reacted with another amine, such as in solvent, such as IpOH, and in the presence of base, such as DIEA, to give the diamine substituted triazine 8. Preferably the reaction is heated, more preferably at a temperature of about >about 75° C., even more preferably at a temperature of about 100° C.

Alternatively, ethers, thioethers and the like can be prepared by substituting other nucleophiles for the amines described above. NaH is the preferred base for preparation of the ethers.

Scheme 5

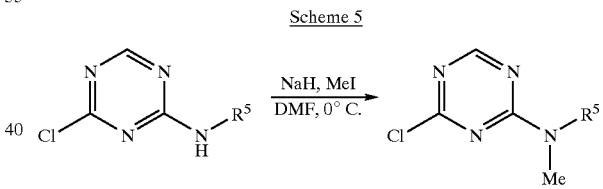

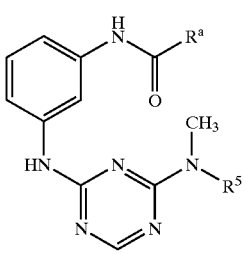

N-Methylamine substituted triazines 9 and 10 can be prepared according to the method set out in Scheme 5. Aminotriazine 7 is alkylated, such as with alkylhalides, in the presence of strong base, such as NaH, to give the alkylamine 9. Preferably the reaction is run at a temperature of about 0° C. The alkylamine triazine 9 can be reacted with amines, similar to that described in Scheme 4, to yield the diamine substituted triazines 10.

Scheme 6

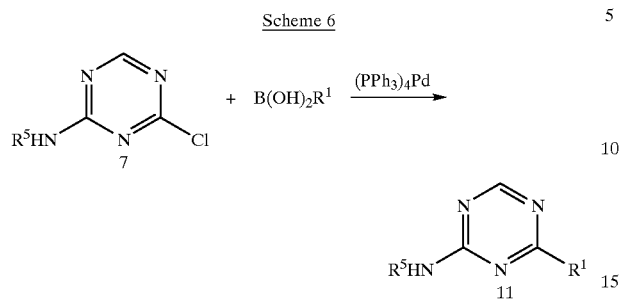

Substituted triazines can be prepared according to the method set out in Scheme 6, similar to that described by M. J. Sharp, et al. *Tetrahedron Letters*, 1987, 28, 5093–5096. Monoamine substituted triazines 7 are reacted with substituted boronic acids such as in the presence of tetrakis (triphenylphosphine) palladium(0), in an appropriate organic solvent, such as EtOH, to yield the disubstituted triazine 11. Preferably the reaction is heated to above RT, more preferably to a temperature where the solvent is at reflux.

Scheme 7

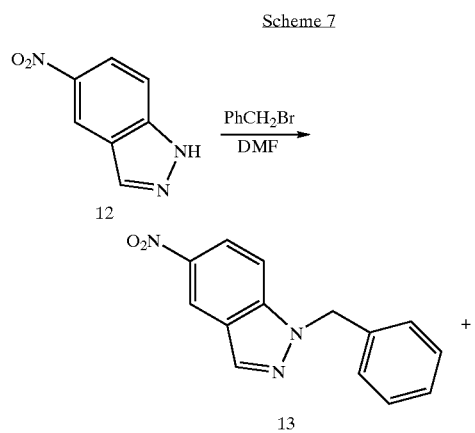

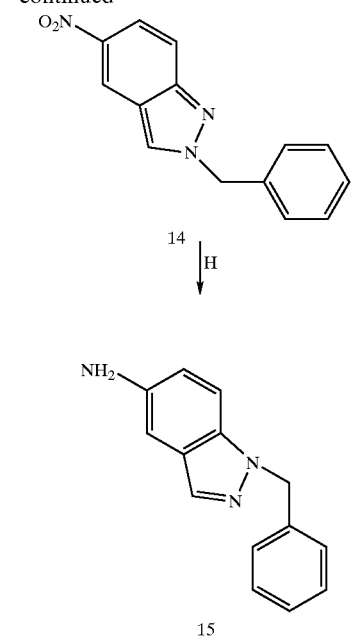

Benzyl substituted aminoindazoles can be prepared according to the method set out in Scheme 7. Nitroindazole 12 is alkylated with benzyl bromide, such as in the presence of $K_2CO_3$. Preferably the reaction is maintained at a temperature of about RT. The reaction yields both the 1-substituted indazole 13 and the 2-substituted isomer 14, which can be separated, such as by chromatography. The nitro compound 13 can be reduced, to give the 1-benzyl-1H-indazol-5-ylamine 15. The reduction preferably takes place in the presence of a suitable reducing agent, such as tin(II) chloride, iron or hydrogen in the presence of an appropriate catalyst, such as Raney nickel (then preferably the hydrogen is used under pressure, e.g. between 2 and 20 bar) or $PtO_2$, in an appropriate solvent, e.g. an alcohol, such as MeOH. The reaction temperature is preferably between about 0° C. and about 80° C., especially about 15° C. to about 30° C.

Scheme 8

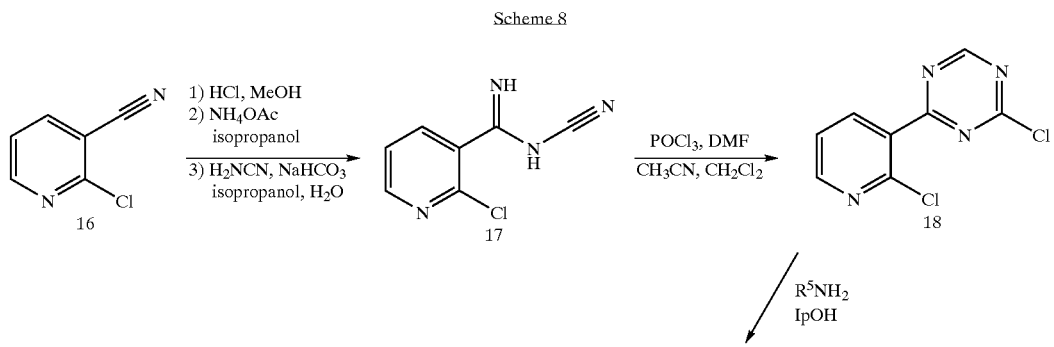

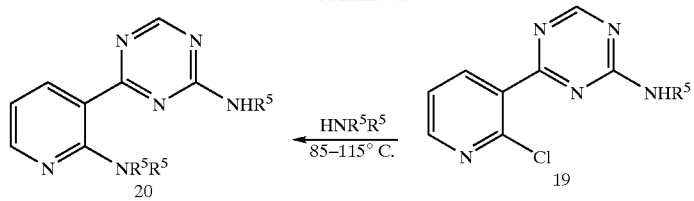

2-Heterocyclic triazines 18, 19 and 20 may be prepared according to Scheme 8. For example, 6-chloronicotinonitrile 16 is reacted with HCl in the presence of a dry alcohol, preferably at a temperature below RT. Ammonium acetate is added to form the amidine which is reacted with cyanamide in the presence of aqueous base, such as of 5% aqueous $NaHCO_3$ to form the cyanoamidine 17. Similar to the method of Scheme 3, cyanoamidine 17 is converted to the 2-chloro-[1,3,5]triazine 18 by reacting with $POCl_3$ and DMF in an organic solvent, such as $CH_2Cl_2$, at a temperature preferably at about RT. Chloro-[1,3,5]triazine 18 reacts with an optionally substituted amine (where $R^5$ is as defined in the formulas herein) to produce 2-amino-4-(2-chloropyrid-3-yl)-triazines 19. The remaining chloride may then be displaced by reaction with amine (neat or in a small amount of solvent) at an elevated temperature to form the 2-amino-4-(2-aminopyrid-3-yl)-triazines 20.

Scheme 9

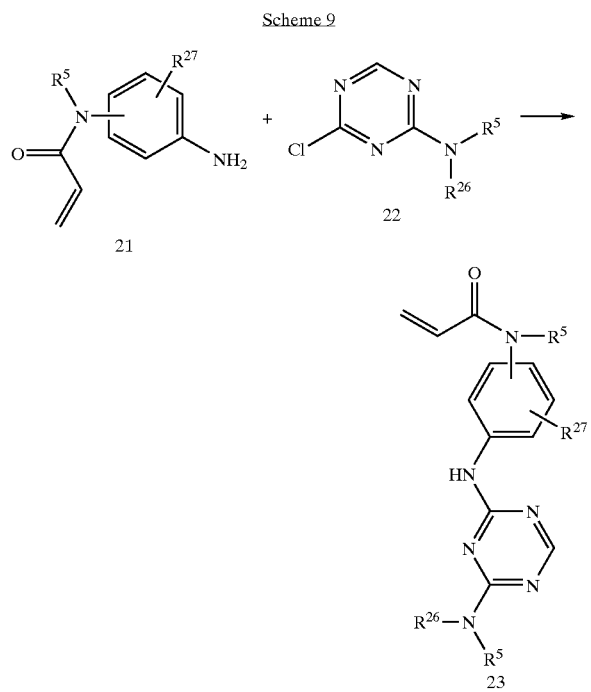

Acrylamide substituted triazines 23 may be prepared according to Scheme 9. Monoamine substituted triazines 21 are reacted with another amine 22, such as in solvent, such as IpOH, and in the presence of base, such as DIEA, to give the diamine substituted triazine 23. Preferably the reaction is heated, more preferably at a temperature of >about 75° C., even more preferably at a temperature of about 100° C.

Alternatively, ethers, thioethers and other the like can be prepared by substituting other nucleophiles for the amines described above.

The starting compounds defined in Schemes 1–9 may also be present with functional groups in protected form if necessary and/or in the form of salts, provided a salt-forming group is present and the reaction in salt form is possible. If so desired, one compound of formula I can be converted into another compound of formula I or a N-oxide thereof; a compound of formula I can be converted into a salt; a salt of a compound of formula I can be converted into the free compound or another salt; and/or a mixture of isomeric compounds of formula I can be separated into the individual isomers.

N-Oxides can be obtained in a known matter by reacting a compound of formula I with hydrogen peroxide or a peracid, e.g. 3-chloroperoxy-benzoic acid, in an inert solvent, e.g. $CH_2Cl_2$, at a temperature between about –10 to about 35° C., such as about 0° C. to about RT.

If one or more other functional groups, for example carboxy, hydroxy, amino, or mercapto, are or need to be protected in a compound of Formulas I–III, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups".

The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from about 130° C. to about 170° C., one molecule of the acid being expelled per molecule of a compound of formula I.

Salts can usually be converted to free compounds, e.g. by treating with suitable basic agents, for example with alkali metal carbonates, alkali metal hydrogen carbonates, or alkali metal hydroxides, typically $K_2CO_3$ or NaOH.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH, IpOH or 1-propanol, nitrites, typically AcCN, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

A compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

The following examples contain detailed descriptions of the methods of preparation of compounds of Formulas I–III. These detailed descriptions fall within the scope, and serve to exemplify, the above described General Synthetic Procedures which form part of the invention. These detailed descriptions are presented for illustrative purposes only and are not intended as a restriction on the scope of the invention.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

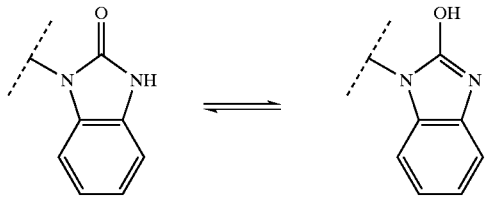

The invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom (see below), whereby they are intended to be attached at any available atom that is not already substituted by an atom other than H.

Such heterocyclic ring systems may be attached through a carbon atom or a heteroatom in the ring system. In instances wherein a heterocyclic or heteroaryl ring system is stated to be attached at a heteroatom (e.g., nitrogen atom), this refers to the heterocyclic or heteroaryl ring system being attached to the designated functional group at said nitrogen heteroatom. Unless otherwise noted, all materials were obtained from commercial suppliers and used without further purification. All parts are by weight and temperatures are in Degrees centigrade unless otherwise indicated. All compounds showed NMR spectra consistent with their assigned structures.

In order that the invention described herein may be more readily understood, the following examples are set forth. It should be understood that these examples are for illustrative purposes only and are not to be construed as limiting this invention in any manner.

Analytical Methods:

Unless otherwise indicated all HPLC analyses were run on a HP-1050 system with an HP Zorbax SB-$C_{18}$ (5$\mu$) reverse phase column (4.6×150 mm) run at 30° C. with a flow rate of 1.00 ml/min.

The mobile phase used solvent A ($H_2O$/0.1% TFA) and solvent B (AcCN/0.1% TFA) with a 20 min gradient from 10% to 90% AcCN. The gradient was followed by a 2 min return to 10% ACCN and a 3 min flush. The peaks of interest eluted on the LC profiles at the times indicated.

LC-MS Method for:

Method A:
1. Samples were run on a HP-1100 MSD system with a HP Zorbax SB-$C_8$ (5$\mu$) reverse phase column (4.6×50 mm) run at 30° C. with a flow rate of 0.75 ml/min.
2. The mobile phase used solvent A ($H_2O$/0.1% HOAc) and solvent B (AcCN/0.1% HOAc) with a 10 min gradient from 10% to 90% AcCN. The gradient was followed by a 1 min return to 10% AcCN and a 2 min flush.
3. The peaks of interest eluted on the LC profiles at the times indicated.

Method B:
1. Samples were run on an HP-1100 system with an HP Zorbax SB-$C_8$ (5$\mu$) reverse phase column (4.6×50 mm) run at 30° C. with a flow rate of 1.5 ml/min.
2. The mobile phase used solvent A ($H_2O$/0.1% HOAc) and solvent B (AcCN/0.1% HOAc) with a 5 min gradient from 10% to 90% AcCN. The gradient was followed by a 0.5 min return to 10% AcCN and a 1.5 min flush.
3. The peaks of interest eluted on the LC profiles at the times indicated.

Preparative HPLC:

Where indicated, compounds of interest were purified via preparative HPLC using a Gilson workstation with a 20×50 mm column at 20 ml/min. The mobile phase used solvent A ($H_2O$/0.1% TFA) and solvent B (AcCN/0.1% TFA) with a 10 min gradient from 5% to 100% AcCN. The gradient was followed by a 2 min return to 5% AcCN.

Proton NMR Spectra:

Unless otherwise indicated, all $^1$H NMR spectra were run on a Varian series Mercury 300 MHz instrument. All observed protons were reported as parts-per-million (ppm) downfield from tetramethylsilane (TMS) or other internal reference in the appropriate solvent indicated.

The following abbreviations are used:

| | |
|---|---|
| RT | room temperature |
| $H_2O$ | water |
| $Na_2SO_4$ | sodium sulfate |
| $NaHCO_3$ | sodium bicarbonate |
| tBuOMe | tert-butylmethoxide |
| DIEA | diisopropylethylamine |
| $Et_3N$ | triethylamine |
| EDC | 1-(3-dimethylaminopropyl)-3-ethylcarbodiimide hydrochloride |
| NaCl | sodium chloride |
| $MgSO_4$ | magnesium sulfate |
| BSA | bovine serum albumin |
| ATP | adenosine triphosphate |
| DTT | dithiothreitol |
| NaOH | sodium hydroxide |
| mg | milligram |
| g | gram |
| ml | milliliter |
| h | hour |
| AcCN | acetonitrile |
| MeOH | methanol |
| EtOH | ethanol |
| IpOH | isopropanol |
| HOAc | acetic acid |
| EtOAc | ethyl acetate |
| Pd-C | palladium on carbon |
| NaH | sodium hydride |
| MeI | methyl iodide |
| $Et_2O$ | ethyl ether |
| TFA | trifluoroacetic acid |
| DMF | dimethylformamide |
| $NaCNBH_3$ | sodium cyanoborohydride |
| $POCl_3$ | phosphoryl chloride |
| $CH_2Cl_2$ | dichloromethane |
| HCl | hydrochloric acid |
| $NH_4OH$ | ammonium hydroxide |
| $NH_4Cl$ | ammonium chloride |
| $MnCl_2$ | manganese chloride |
| Boc | tert-butyloxycarbonyl |
| HOBt | hydroxybenzotriazole |
| $K_2CO_3$ | potassium carbonate |
| min | minutes |
| $FeSO_4$ | ferric sulfate |
| LiOH | lithium hydroxide |
| LDA | lithium dilsopropylamide |

Preparation I

3-Nitroaniline (2.0 g, 14.48 mmol) was dissolved in $CH_2Cl_2$ (75 ml) and cooled to 0° C. To this solution were added EDC (8.3 g, 43.4 mmol), HOBT (5.9 g, 43.4 mmol), DIEA (12.6 ml, 72.4 mmol) and acrylic acid (3.97 ml, 57.9 mmol). The reaction mixture was kept at RT for 1.25 h. The reaction mixture was diluted with EtOAc and washed with brine. The organic layer was dried over $Na_2SO_4$, filtered, and evaporated in vacuo. The residue was purified by column chromatography using 1:1 EtOAc/hexanes as the solvent to give N-(3-nitrophenyl)acrylamide.

Preparation II

A mixture of N-(3-nitrophenyl)-acrylamide (1.1 g, 5.61 mmol), iron powder (1.88 g, 33.7 mmol), $FeSO_4$ (3.12 g, 11.2 mmol), Celite® (1.0 g) and $H_2O$ (45 mL) was heated to reflux with stirring for 2 h. The reaction mixture was cooled to RT and the solution was made basic to pH 13–14 by the addition of 2N NaOH. The reaction mixture was diluted with EtOAc and water. The solution was filtered to remove the solids and the solids were washed with EtOAc. The aqueous layer was extracted three times with EtOAc (100 mL) and the combined organics were dried over $Na_2SO_4$, filtered, and evaporated in vacuo. The residue was purified by column chromatography using EtOAc as the solvent to give N-(3-aminophenyl)acrylamide.

Preparation III

Sodium dicyanamide (105.9 g, 1.19 mol) was nearly dissolved into $H_2O$ and added quickly to concentrated HCl (530 ml) pre-cooled to about −18° C. The resulting slurry was stirred at −18° C. for about 15 min, warmed to 35° C. and re-cooled to 10° C. The resulting white precipitate was filtered, washed with small amounts of water, and dried under vacuum for 20 h. N-Cyanochloroformamidine (~50 g) was obtained. DMF (27.3 ml) was dissolved in $CH_2Cl_2$ (550 ml) at RT. $POCl_3$ (27.3 ml) was added and after about 5 min, N-cyanochloroformamidine (30 g) was also added. The mixture was stirred overnight at RT, then washed 3 times with water and once with brine. The organic layer was dried over $Na_2SO_4$, filtered, and evaporated under reduced pressure. The white solid thus obtained was identified as the 2,4-dichloro-1,3,5-triazine.

Preparation IV 2,4-Dichloro-1,3,5-triazine (1.054 g, 7.028 mmol) is dissolved in DMF (5 ml) and cooled to 0° C. To this solution, DIEA (1.225 ml, 7.028 mmol) and 3,4,5-trimethoxyaniline (1.185 g, 6.47 mmol) are added. The reaction mixture is kept at 0° C. for 15 to 30 min and at RT for about 2 h. The reaction mixture is diluted with EtOAc and washed with brine. The organic layer is dried over $Na_2SO_4$l filtered, and evaporated in vacuo. The residue is added to $CH_2Cl_2$ and the resulting white precipitate is filtered and dried under reduced pressure to give (4-chloro-[1,3,5]triazin-2-yl)-(3,4,5-trimethoxyphenyl)amine.

Similarly, the following compounds can be prepared from 2,4-dichloro-1,3,5-triazine and the appropriate amine:
3-(4-chloro-[1,3,5]triazin-2-ylamino)-benzoic acid methyl ester,
(4-chloro-[1,3,5]triazin-2-yl)-naphthalen-1-yl-amine;
(4-benzyloxy-phenyl)-(4-chloro-[1,3,5]triazin-2-yl)-amine;
2-chloro-4-(3-chloro-4-fluoroanilino)-1,3,5-triazine; and
(4-chloro-[1,3,5]triazin-2-yl)-3-chloronaphthalen-1-yl-amine.

Preparation V 3-(4-Chloro-[1,3,5]triazin-2-yl)-2-oxo-2,3-dihydro-benzimidazole-1-carboxylic acid tert-butyl ester was prepared by a process similar to that described by N. A. Meanwell, et al., *J. Org Chem.*, 60,1565–82 (1995). A mixture of 2,4-dichloro-1,3,5-triazine (0.64, 4.26 mmol) and solid $K_2CO_3$ (0.6 g, 4.34 mmol) was suspended in AcCN (10 mL) under nitrogen at RT followed by addition of 2,3-dihydro-2-oxo-1H-benzimidazole-1-carboxylic acid, 1,1-dimethylethyl ester (1.0 g, 4.26 mmol). The mixture was stirred at RT for 1.5 h. The mixture was poured onto ice/water and the white solid formed, was collected by suction filtration and dried under vacuum to give 3-(4-chloro-[1,3,5]triazin-2-yl)-2-oxo-2,3-dihydro-benzimidazole-1-carboxylic acid tert-butyl ester.

Preparation VI

To a solution of N-(tert-butoxycarbonyl)-phenylene-1,4-diamine (1.5 g, 7.20 mmol) and $Et_3N$ (5 mL) in $CH_2Cl_2$ (50 mL) was added 4-nitrobenzenesulfonylchloride. The mixture was stirred at RT for 18 h. The reaction was diluted with $CH_2Cl_2$ and the organics were washed with water. The organic extracts were dried over anh. $MgSO_4$ and concentrated under reduced pressure. The crude product was purified via medium pressure liquid chromatography using $CH_2Cl_2$ followed by 1:99 $MeOH/CH_2Cl_2$ as the solvent system to yield $N^1$-(tert butoxycarbonyl)-$N^4$—(4-nitrophenylsulfonyl)-phenylene-1,4-diamine. The Boc protection was removed by dissolving in $CH_2Cl_2$ (15 mL) followed by addition of TFA (5 mL) and stirring for 2 h at RT. The organics were concentrated to dryness and the residue was taken up in a mixture of EtOAc and saturated $NaHCO_3$. The organics were separated, dried over anh. $MgSO_4$ and concentrated under reduced pressure to give N-(4-nitrophenylsulfonyl)-phenylene-1,4-diamine.

Preparation VII

To a solution of 1,3-phenylenediamine (3.0 g, 27.7 mmol) and triethylamine (10 mL) in $CH_2Cl_2$ (50 mL) was added 4-nitrobenzenesulfonylchloride. The mixture was stirred at RT for 18 h. The reaction was taken up in a mixture of EtOAc (1 L) and saturated $NaHCO_3$ (100 mL). The separated organics were dried over anh. $MgSO_4$ and concentrated under reduced pressure. The crude organics were purified via medium pressure liquid chromatography using $CH_2Cl_2$ followed by 2:98 $MeOH/CH_2Cl_2$, followed by 0.5:5:995 Conc. $NH_4OH/MeOH/CH_2Cl_2$ as the solvent system to give $N^3$-(4-nitrophenylsulfonyl)-phenylene-1,3-diamine.

Preparation VIII

A mixture of 4-nitrophenylisocyanate (1.0 g, 6.09 mmol) and (S)-(+)-3-hydroxytetrahydrofuran (1.0 mL, 11.3 mmol) was suspended in toluene (20 mL) under nitrogen. The mixture was stirred at RT for 18 h. The reaction was concentrated under reduced pressure. The crude compound was purified via medium pressure liquid chromatography using $CH_2Cl_2$ followed by 1:99 $MeOH/CH_2Cl_2$ as the solvent system to give N—(S)-(+)-3-tetrahydrofuranyloxycarbonyl-4-nitroaniline. The compound was added to a suspension of 10% Pd/C (500 mg) and EtOH (20 mL). The mixture was stirred under a hydrogen gas atmosphere for 24 h. The catalyst was removed by suction filtration and the organics were concentrated under reduced pressure. The crude compound was purified via medium pressure liquid chromatography using $CH_2Cl_2$ followed by 1:99 $MeOH/CH_2Cl_2$ followed by 5:95 $MeOH/CH_2Cl_2$ as the solvent system to give N—(S)-(+)-3-tetrahydrofuranyloxycarbonyl-1,4-phenylenediamine.

Preparation IX

A mixture of 3-nitrophenylisocyanate (1.0 g, 6.09 mmol) and (S)-(+)-3-hydroxytetrahydrofuran (1.0 mL, 11.3 mmol) was suspended in toluene (20 mL) under nitrogen. The mixture was stirred at RT for 18 h. The reaction was concentrated under reduced pressure. The crude compound was purified via medium pressure liquid chromatography using $CH_2Cl_2$ followed by 1:99 $MeOH/CH_2Cl_2$ as the solvent system to give N—(S)-(+)-3- tetrahydrofuranyloxycarbonyl-3-nitroaniline. The compound was added to a suspension of 10% Pd/C (500 mg) and EtOH (20 mL). The mixture was stirred under a hydrogen gas atmosphere for 24 h. The catalyst was removed by suction filtration and the organics were concentrated under reduced pressure. The crude compound was purified via medium pressure liquid chromatography using $CH_2Cl_2$ followed by 1:99 MeOH/$CH_2Cl_2$ followed by 5:95 MeOH/$CH_2Cl_2$ as the solvent system to give N—(S)-(+)-3-tetrahydrofuranyloxycarbonyl-1,3-phenylenediamine.

Preparation X 2,4-Dichloro-1,3,5-triazine (89.1 mg, 0.5944 mmol) is dissolved in DMF (0.5 ml) and cooled to 0° C. To this solution are added DIEA (104 µl) and a solution of 4-methoxy-3-(2-methoxy-ethoxy)-phenylamine-TFA salt (264 mg, ~0.59 mmol) 4-Methoxy-3-(2-methoxy-ethoxy)-phenylamine is prepared from 5-amino-2-methoxyphenol using known procedures. The amine is Boc-protected, the phenol is alkylated with 2-bromoethylmethylether, and the Boc group is removed with TFA, leaving the TFA salt of the desired aniline.) and DIEA (208 µl) in DMF (1 ml). The reaction mixture is kept at 0° C. for 15 to 30 minutes and then at RT for 15 minutes to 2 hours. The reaction mixture is diluted with EtOAc and washed with brine. The organic layer is dried over $Na_2SO_4$, filtered, and evaporated in vacuo, to give crude (4-chloro-[1,3,5]triazin-2-yl)-[4-methoxy-3-(2-methoxy-ethoxy)-phenyl]-amine.

Preparation XI 2,4-Dichloro-1,3,5-triazine (12.6 g, 84 mmol) was dissolved into DMF (100 mL) under $N_2$ and cooled to 0° C. DIEA (11.7 g, 90 mmol) was added, followed by 4-aminoveratrole (13.35 g, 87 mmol). The reaction solution was stirred with gradual warming to RT. The reaction was quenched after 3.5 h with water, which causes a gray precipitate to form. This precipitate was recovered by vacuum filtration, washed with cold water, dried under high vacuum, then eluted through a 28×4.5 cm column of silica gel (0.1% $NH_4OH_{(aq)}$ buffered 1%, 2%, 3%, 4%, and 5% MeOH/$CH_2Cl_2$ step gradient) giving (4-chloro-[1,3,5]triazin-2-yl)-(3,4-dimethoxy-phenyl)-amine as an off white solid.

Similarly, the following compounds can be prepared from 2,4-dichloro-1,3,5-triazine and commercially available anilines or with anilines synthesized according to readily available literature procedures:

(4-chloro-[1,3,5]triazin-2-yl)-(3,4-diethoxy-phenyl)-amine,
(4-chloro-[1,3,5]triazin-2-yl)-(3,4-dipropoxy-phenyl)-amine,
(4-chloro-[1,3,5]triazin-2-yl)-[3-methoxy-4-(2-methoxyethoxy)phenyl]amine,
(4-chloro-[1,3,5]triazin-2-yl)-3-methylphenyl-amine, and
(4-chloro-[1,3,5]triazin-2-yl)-[4,5-dimethoxy-3-(2-morpholin-4-yl-ethoxy)-phenyl]-amine.

Preparation XII (4-Chloro-[1,3,5]triazin-2-yl)-[4-methoxy-3-(2-morpholin-4-yl-ethoxy)-phenyl]-amine was prepared by the alkylation of 2-methoxy-5-nitrophenol with 4-(2-chloroethyl)morpholine hydrochloride using $K_2CO_3$ in refluxing acetone/water.

Standard acid/base workup gave 4-[2-(2-methoxy-5-nitrophenoxy)-ethyl]-morpholine as a yellow solid, which was purified by trituration with $Et_2O$. The resulting yellow solid was converted to the amine by standard hydrogenation using 10% Pd—C in MeOH and EtOAc at RT. Filtration through Celite™ and concentration of the filtrate gave (4-chloro-[1,3,5]triazin-2-yl)-[4-methoxy-3-(2-morpholin-4-yl-ethoxy)-phenyl]-amine.

By similar methods, 3-(2-diethylamino-ethoxy)-4-methoxy-phenylamine, 3-methoxy-4-(2-morpholin-4-yl-ethoxy)-phenylamine and 4-(2-diethylamino-ethoxy)-3-methoxy-phenylamine were prepared.

Preparation XIII (3-Amino-phenyl)-acetic acid methyl ester was prepared by reacting 3-aminophenylacetic acid with acetyl chloride in MeOH to afford the corresponding methyl ester, HCl salt, (3.09 g, 15.324 mmol). The ester was dissolved in DMF (5 ml) with DIEA (2.67 ml, 15.324 mmol) and cooled to 0° C. To this solution was added dropwise a 0° C. solution of DMF (5 ml) containing 2,4-dichloro-1,3,5-triazine (2.297 g, 15.324 mmol) and DIEA (2.67 ml, 15.324 mmol). The reaction was stirred at 0° C. for 15 min and then at RT for 1 h. The reaction mix was diluted with EtOAc and water. The layers were separated, and the aqueous layer was extracted twice with EtOAc. The combined organic layers were washed 4 times with brine and dried over $Na_2SO_4$. The crude was concentrated down and dried under reduced pressure, giving [3-(4-chloro-[1,3,5]triazin-2-ylamino)-phenyl]-acetic acid methyl ester.

Preparation XIV 2,4-Dichloro-1,3,5-triazine (173.7 mg, 1.158 mmol) was dissolved into DMF (1 ml). To the stirring solution, cooled to 0° C., was added DIEA (202 µl, 1.158 mmol). This solution was added dropwise to a 0° C. mix of DMF (1 ml) and 3-aminophenyl acetamide. The reaction was stirred at 0° C. for 15 min and then at RT for 1 h. The reaction mix was diluted with EtOAc and water. The layers were separated, and the aqueous layer was extracted twice with EtOAc. The combined organic layer was washed 3 times with brine, dried over $Na_2SO_4$, and concentrated under reduced pressure, giving 2-[3-(4-chloro-[1,3,5]triazin-2-ylamino)-phenyl]acetamide.

Preparation XV

2-[3-(4-Chloro-[1,3,5]triazin-2-ylamino)-phenyl]-acetamide (136.5 mg, 0.5177 mmol) is combined with 2-chlorobenzimidazole (86.9 mg, 0.5177 mmol) and potassium carbonate (93 mg, 0.673 mmol) in AcCN (5 ml) and heated at 65–75° C. for 2 to 20 hours. The reaction mix is cooled to RT and the inorganic salts were filtered off. The AcCN solution is concentrated down under reduced pressure. The crude is purified on a silica gel column with an EtOAc/hexane to MeOH/$CH_2Cl_2$ elution gradient, giving 2-{3-[4-(2-chloro-benzoimidazol-1-yl)-[1,3,5]triazin-2-ylamino]-phenyl}acetamide.

Preparation XVI

To 2-chloro-4-(3-chloro-4-fluoroanilino)-1,3,5-triazine (1.7 g, 6.56 mmol) and MeI (1.5 mL) in DMF (20 mL) under a nitrogen atmosphere was added NaH (60% dispersion, 0.53 mg, 13.3 mmol). The mixture was stirred for 3 h. The reaction was quenched by the addition of water and the organic extracts are taken up in EtOAc, dried over anh. $MgSO_4$ and concentrated under reduced pressure. The crude was purified via medium pressure liquid chromatography using $CH_2Cl_2$ as the solvent system to give N-methyl-2-chloro-4-(3-chloro-4-fluoroanilino)-1,3,5-triazine.

Similarly, the following compounds can be prepared from the appropriate triazine and alkyl halide:
N-allyl-(3-chloro-4-fluoro-phenyl)-(4-chloro-[1,3,5]triazin-2-yl)-amine;
N-ethyl-2-chloro-4-(3-chloroanilino)-1,3,5-triazine;
and N-ethyl-2-chloro-4-(3-chloro-4-fluoroanilino)-1,3,5-triazine.

Preparation XVII 7-(Trifluoromethyl)-1,2,3,4-tetrahydroquinoline (440 mg, 2.2 mmol) was dissolved in DMF (10 mL) under $N_2$ at room temperature. DIEA (284 mg, 2.2 mmol) was added, and the reaction solution was cooled to 0° C. 2,4-Dichloro-1,3,5-triazine was added, and reaction was stirred with gradual warming to RT. The reaction was quenched after 3 h with water, which caused a fine precipitate to form, which is not filterable. This mixture was extracted 3 times with EtOAc. The EtOAc extracts were then washed brine, combined, dried over $Na_2SO_4$, filtered, concentrated, and dried under high vacuum giving 1-(4-chloro-[1,3,5]triazin-2-yl)-7-trifluoromethyl-1,2,3,4-tetrahydro-quinoline (800 mg (>100%)) of a yellow oil that was used without further purification.

Preparation XVIII 2,4-Dichloro-1,3,5-triazine (1.95 g, 13 mmol) was dissolved in DMF (50 mL) under $N_2$ and cooled to 0° C. DIEA (1.68 g, 13 mmol) was added, followed by the addition of 6-methyl-1,2,3,4-tetrahydroquinoline (1.91 g, 13 mmol). The reaction was stirred with gradual warming to RT. The reaction was quenched after 3 h with water, which causes a sticky precipitate to form. The mixture was extracted 3× with EtOAc. The EtOAc extracts were washed brine, combined, dried over $Na_2SO_4$, filtered, and concentrated, then dried under high vacuum to remove residual traces of DMF. The recovered material was purified by elution through a 17×2.5 cm column of silica gel (5%, 10%, 20% and 40% EtOAc/Hexane step gradient) giving 1-(4-chloro-[1,3,5]triazin-2-yl)-6-methyl-1,2,3,4-tetrahydro-quinoline as a white solid.

Preparation XIX 2,4-Dichloro-1,3,5-triazine (3 g, 20 mmol) was dissolved in DMF (20 mL) under $N_2$ and cooled to 0° C. DIEA (2.58 g, 20 mmol) was added, followed by 3-chloro-6-methylaniline (2.83 g, 20 mmol). The reaction solution was stirred with gradual warming to RT. The reaction was quenched after 3 h with water, then extracted 3 times with EtOAc. The EtOAc extracts were washed with brine, combined, dried over $Na_2SO_4$, filtered, and concentrated. The crude was eluted through a 17×2.5 cm column of silica gel (25%, 40%, 60% EtOAc/Hexane step gradient) giving (5-chloro-2-methyl-phenyl)-(4-chloro-[1,3,5]triazin-2-yl)-amine as a white solid.

Preparation XX 2-(4-Nitrophenoxy)ethanol (1.83 g, 10 mmol) was dissolved in EtOH (100 mL) under air at RT. A catalytic amount of 10% Pd/C was added. The air was replaced with a $H_{2(g)}$ atmosphere and the reaction was stirred vigorously for 18 h. The reaction was quenched by filtering it through Celite® with EtOH. The filtrate was concentrated under reduced pressure and the recovered material was purified by eluting it through a 17×2.5 cm column of silica gel (5% and 10% MeOH/$CH_2Cl_2$ step gradient) giving 2-(4-amino-phenoxy) ethanol as a black solid: MS m/z 154=$[M+H]^+$. Calc'd for $C_8H_{11}NO_2$: 153.08.

Preparation XXI

Based on G. W. Gribble, et al., *Synthesis*, 1975, 650–652, 6-methoxyquinoline (1.26 g, 7.9 mmol) was dissolved in glacial acetic acid (20 mL) under $N_2$ at RT. Solid $NaCNBH_3$ (2 g, 32 mmol) was added in small portions over a 45 min period. The reaction was heated to 50° C. for 8 h, then cooled to RT and stirred overnight. The reaction was quenched by cooling it to 0° C., and the pH of the solution was adjusted to 14 with 2 N NaOH. The solution was extracted 3 times with EtOAc. The EtOAc extracts were washed brine, combined, dried over $Na_2SO_4$, filtered, and concentrated, then eluted through a 17×2.5 cm column of silica gel (5% and 10% EtOAc/Hexane step gradient) giving 6-methoxy-1,2,3,4-tetrahydroquinoline as a red oil. This material was used without further purification.

Preparation XXII

Based on B. S. Rauckman et al., *J. Med. Chem.*, 1989, 32, 1927–1935, 5-chloroquinoline (1.01 g, 6.2 mmol) was dissolved into anh. EtOH (30 mL) under $N_2$ at RT. Concentrated HCl (2.14 mL, 24.8 mmol) was added, followed by the addition of the $NaCNBH_3$ (1.56 g, 24.8 mmol). This produced a vigorous gas and heat evolution. The reaction was heated to 60° C. for 2 h, then cooled and stirred at RT for an additional 18 h. The reaction was quenched by adjusting the pH to approximately 9 with 2 N NaOH. This mixture was extracted 3 times with EtOAc. The EtOAc extracts were washed brine, combined, dried over $Na_2SO_4$, filtered, and concentrated, then eluted through a 17×2.5 cm column of silica gel (5%, 10%, 15%, 40% and 50% EtOAc/Hexane step gradient) giving 5-chloro-1,2,3,4-tetrahydroquinoline as a green oil: MS m/z 168=$[M+H]^+$. Calc'd for $C_9H_{10}NCl$—167.05.

Similarly, 7-chloro-1,2,3,4-tetrahydroquinoline was prepared as an orange solid: MS m/z 168=$[M+H]^+$. Calc'd for $C_9H_{10}NCl$—167.05.

Preparation XXIII

Based on R. Nagata et al., *J. Med. Chem.*, 1994, 37, 3956–3968, 1,2,3,4-tetrahydroquinoline (1.33 g, 10 mmol) was dissolved in DMF (15 mL) under $N_2$ and cooled to 0° C. N-Chlorosuccinimide (1.35 g, 10 mmol) was dissolved in DMF (10 mL) under $N_2$ and was added to the tetrahydroquinoline solution dropwise, via pressure equalizing dropping funnel, over 45 min. The reaction was stirred at 0° C. for 3 h, then quenched by pouring it into water (100 mL). This mixture was extracted with a 5:1 mixture of EtOAc:toluene, then two times with EtOAc. All of the organic extracts were washed with brine, combined, dried over $Na_2SO_4$, filtered, and concentrated, then eluted through a 17×2.5 cm column of silica gel (5%, 10% and 15% EtOAc/Hexane step gradient) giving 6-chloro-1,2,3,4-tetrahydroquinoline as a green oil.

Preparation XXIV

To a mixture of 3-(4-chloro-[1,3,5]triazin-2-ylamino)-phenyl]-acetic acid methyl ester (279 mg, 1.001 mmol) in IpOH (3 ml) were added DIEA (175 μl, 1.001 mmol) and 3-bromoaniline (172 mg, 1.001 mmol). The mix was heated at 100–120° C. for 18 h. The solution was cooled to RT and sonicated. The precipitate was filtered and then dried under reduced pressure, giving {3-[4-(3-bromo-phenylamino)-[1,3,5]triazin-2-ylamino]-phenyl}-acetic acid methyl ester. MS m/z 415=$[M+H]^+$. Calc'd for $C_{18}H_{16}BrN_5O_2$: 413.05.

Preparation XXV

{3-[4-(3-Bromo-phenylamino)-[1,3,5]triazin-2-ylamino]-phenyl)-acetic acid methyl ester (142 mg, 0.3425 mmol) was dissolved in THF (34.5 ml) and 1N LiOH/water (6.85 ml). The reaction was stirred vigorously at RT for 2 h. The organic solvent was evaporated off. The aqueous solution was acidified to pH 3 with 1N HCl, whereupon a white precipitate formed. The precipitate was filtered and dried under vacuum, giving {3-[4-(3-bromo-phenylamino)-[1,3,5]triazin-2-ylamino]-phenyl}-acetic acid. MS m/z 401=$[M+H]^+$. Calc'd for $C_{17}H_{14}BrN_5O_2$: 399.03.

EXAMPLE 1

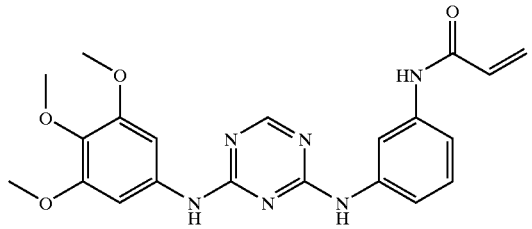

N-[3-[4-(3,4,5-Trimethoxy-phenylamino)-[1,3,5]triazin-2-ylamino]phenyl]acrylamide To a slurry of (4-chloro-[1,3,5]triazin-2-yl)-(3,4,5-trimethoxy-phenyl)amine (54.9 mg, 0.185 mmol) in IpOH (2.5 ml) was added DIEA (0.048 mL, 0.277 mmol) and N-(3-aminophenyl)acrylamide (33 mg, 0.203 mmol). The mix was heated at 100° C. for 18 h. The solution was cooled to RT and a precipitate formed. The precipitate was filtered off and dried under reduced pressure to give N-{3-[4-(3,4,5-trimethoxy-phenylamino)-[1,3,5]triazin-2-ylamino]-phenyl)-acrylamide: MS m/z=423[M+H]$^+$. Calc'd for $C_2H_{22}N_6O_4$: 422.17.

EXAMPLE 2

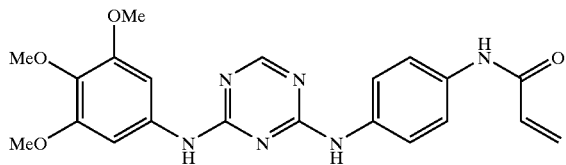

N-{4-[4-(3,4,5-Trimethoxy-phenylamino)-[1,3,5]triazin-2-ylamino]phenyl}-acrylamide Step 1: Preparation of N-(4-nitrophenyl)-acrylamide 4-Nitroaniline (0.4 g, 2.9 mmol) was dissolved in $CH_2Cl_2$ (15 ml). To this solution was added EDC (1.67 g, 8.7 mmol), HOBT (1.17 g, 8.7 mmol), DIEA (2.5 ml, 14.5 mmol) and acrylic acid (0.79 ml, 11.6 mmol). The reaction mixture was kept at RT for 4.5 h. The reaction mixture was diluted with EtOAc and washed with brine. The organic layer was dried over $Na_2SO_{41}$ filtered, and evaporated in vacuo. The residue was purified by column chromatography using 2:1 EtOAc/hexanes as the solvent to give N-(4-nitrophenyl)-acrylamide.

Step 2: Preparation of N-(4-aminophenyl)-acrylamide

A mixture of N-(4-nitrophenyl)-acrylamide (Step 1) (0.203 g, 1.06 mmol), Iron powder (0.354 g, 6.34 mmol), $FeSO_4$ (0.587 g, 2.11 mmol), Celite® (0.2 g) and water (6 mL) was heated to reflux with stirring for 3 h. The reaction mixture was cooled to RT and the solution was made basic to pH 13–14 by the addition of 2 N NaOH. The reaction mixture was diluted with EtOAc and water. The solution was filtered to remove the solids and solids washed with EtOAc. The aqueous layer was extracted three times with EtOAc (25 mL) and the combined organics were dried over $Na_2SO_4$, filtered, and evaporated in vacuo. The residue was purified by column chromatography using EtOAc as the solvent to give N-(4-aminophenyl)-acrylamide.

Step 3: Preparation of N-{4-[4-(3,4,5-trimethoxy-phenylamino)-[1,3,5]triazin-2-ylamino]phenyl}-acrylamide To a slurry of (4-chloro-[1,3,5]triazin-2-yl)-(3,4,5-trimethoxy-phenyl)amine (29.9 mg, 0.101 mmol) in IpOH (2.5 ml) was added DIEA (0.026 mL, 0.151 mmol) and N-(4-aminophenyl)acrylamide (Step 2) (18 mg, 0.111 mmol). The mixture was heated at 100° C. for 18 h. The solution was cooled to RT. The organics were evaporated in vacuo and the residue was purified by column chromatography using 9:1 $CH_2Cl_2$/MeOH as the solvent to give N-(4-[4-(3,4,5-trimethoxy-phenylamino)-[1,3,5]triazin-2-ylamino]phenyl}-acrylamide: MS m/z 423[M+H]$^+$. Calc'd for $C_{21}H_{22}N_6O_4$: 422.17.

EXAMPLE 3

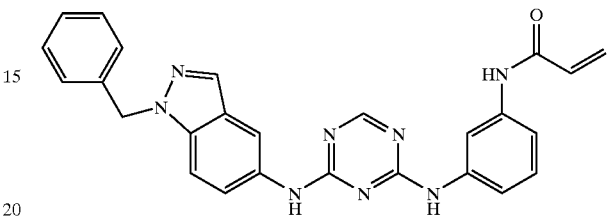

N-{3-[4-(1-Benzyl-1H-indazol-5-ylamino)-[1,3,5]triazin-2-ylamino]-phenyl}-acrylamide Step 1. Preparation of 1-benzyl-5-nitro-1H-indazole and 2-benzyl-5-nitro-2H-indazole To a solution of 10 g (61.3 mmol) of 5-nitroindazole in DMF (100 mL) was added $K_2CO_3$ (12.7 g, 91.9 mmol) and $PhCH_2Br$ (7.29 mL, 61.3 mmol). The resulting mixture was stirred at RT for 3.5 days, then poured into 400 mL of water. The resulting slurry was filtered, rinsed once with water and dried in vacuo giving a beige solid. A 2.5 g portion of this crude material was purified by chromatography ($SiO_2$, elution with 1:2 EtOAc-hexanes) giving 1-benzyl-5-nitro-1H-indazole and 2-benzyl-5-nitro-2H-indazole.

Step 2. Preparation of (1-benzyl-1H-indazol-5-yl)amine

To 906.4 mg (3.58 mmol) of 1-benzyl-5-nitro-1H-indazole (Step 1) in 20 mL of MeOH and 5 mL of EtOAc at RT was added a slurry of 150 mg of 10% Pd—C in 5 mL of MeOH. The resulting slurry was then stirred under a balloon of $H_2$ for 1.2 h, filtered through Celite®, and rinsed with MeOH and EtOAc. Concentration of the filtrate gave (1-benzyl-1H-indazol-5-yl)amine as a pinkish solid: MS m/z=224 [M+H]$^+$. Calc'd for $C_{14}H_{13}N_3$: 223.11.

Step 3. Preparation of (1-benzyl-1H-indazol-5-yl)-(4-chloro-[1,3,5]triazin-2-yl)amine To 2,4-dichloro-1,2,5-triazine (526.1 mg, 3.51 mmol) in DMF (15 mL) at $O_2C$ was added DIEA (0.733 mL, 4.21 mmol). The resulting yellow solution was stirred at 0° C. for 20 min and 1-benzyl-1H-indazol-5-ylamine (Step 2) (783.5 mg, 3.51 mmol) was added in one portion followed by 2×2.5 mL DMF flask rinses. The resulting mixture was stirred at 0° C. for 30 min, at RT for 4.5 h, then diluted with EtOAc. The organic layer was washed twice with water and once with brine. The aqueous layer and washings were extracted with EtOAc. The combined organics were dried, concentrated, and purified by chromatography ($SiO_2$, elution with 1:1 EtOAc-hexanes) to give a slightly impure pinkish solid. Trituration with $Et_2O$ gave (1-benzyl-1H-indazol-5-yl)-(4-chloro-[1,3,5]triazin-2-yl)amine as a light pink solid: MS m/z=337 [M+H]$^+$. Calc'd for $C_{17}H_{13}ClN_6$: 336.09.

Step 4. Preparation of N-(3-[4-(1-benzyl-1H-indazol-5-ylamino)-[1,3,5]triazin-2-ylamino]-phenyl)-acrylamide To a slurry of (1-benzyl-1H-indazol-5-yl)-(4-chloro-[1,3,5]triazin-2-yl)-amine (Step 3) (50.0 mg, 0.148 mmol) in IpOH (2.5 ml) was added DIEA (0.039 mL, 0.222 mmol) and N-(3-aminophenyl)acrylamide (26.5 mg, 0.163 mmol).

The mix was heated at 100° C. for 18 h. The solution was then cooled to RT. A precipitate fell out of solution and was filtered off and dried under reduced pressure to give N-{3-[4-(1-benzyl-1H-indazol-5-ylamino)-[1,3,5]triazin-2-ylamino]-phenyl}-acrylamide: MS m/z=463[M+H]$^+$. Calc'd for $C_{26}H_{22}N_8O$: 462.19.

EXAMPLE 4

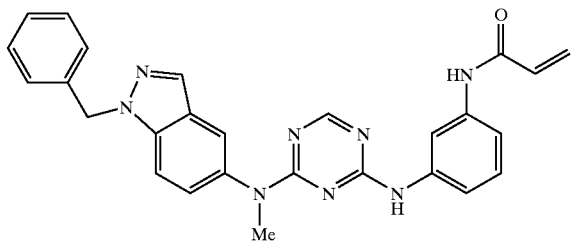

N-(3-{4-[(1-Benzyl-1H-indazol-5-yl)-methyl-amino]-[1,3,5]triazin-2-ylamino}-phenyl)-acrylamide Step 1: Preparation of (1-benzyl-1H-indazol-5-yl)-(4-chloro-[1,3,5]triazin-2-yl)methylamine To (1-benzyl-1H-indazol-5-yl)-(4-chloro-[1,3,5]triazin-2-yl)amine (Example 3, Step 3) (473 mg, 1.40 mmol) in DMF (7.5 mL) at 0° C. was added MeI (0.262 mL, 4.21 mmol) followed by NaH (60% dispersion in oil) (67.4 mg, 1.69 mmol). The resulting mixture was stirred at 0° C. for 4.25 h. Additional NaH (10 mg) was added after 3.1 h as TLC indicated remaining starting material. At this point, the reaction mixture was quenched with satd aq NH$_4$Cl and diluted with water and EtOAc. The organic layer was washed with water and brine. The aqueous layer and washings were extracted once with EtOAc. The combined organics were dried, concentrated and purified by chromatography (SiO$_2$, elution with 1:1 EtOAc-hexanes) to give (1-benzyl-1H-indazol-5-yl)-(4-chloro-[1,3,5]triazin-2-yl)methylamine as a pale oil: MS m/z=351 [M+H]$^+$. Calc'd for $C_{18}H_{15}ClN_6$: 350.10.

Step 2: Preparation of N-(3-(4-[(1-benzyl-1H-indazol-5-yl)-methyl-amino]-[1,3,5]triazin-2-ylamino}phenyl)-acrylamide To a slurry of (1-benzyl-1H-indazol-5-yl)-(4-chloro-[1,3,5]triazin-2-yl)methylamine (Step 1) (52.0 mg, 0.148 mmol) in IpOH (2.0 ml) was added DIEA (0.039 mL, 0.222 mmol) and N-(3-aminophenyl)acrylamide (26.4 mg, 0.163 mmol). The mix was heated at 100° C. for 18 h. The solution was then cooled to RT. The organics were evaporated in vacuo and the residue was purified by column chromatography using EtOAc as the solvent to give N-(3-(4-[(1-benzyl-1H-indazol-5-yl)-methyl-amino]-[1,3,5]triazin-2-ylamino}phenyl)-acrylamide: MS m/z=477[M+H]$^+$. Calc'd for $C_{27}H_{24}NSO$: 476.21.

EXAMPLE 5

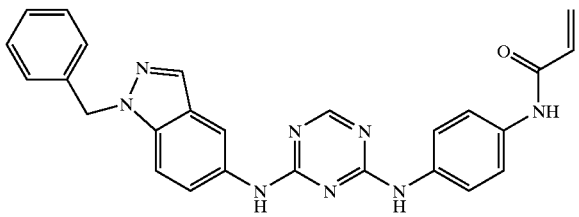

N-{4-[4-(1-Benzyl-1H-indazol-5-ylamino)-[1,3,5]triazin-2-ylamino]-phenyl}-acrylamide To a slurry of (1-benzyl-1H-indazol-5-yl)-(4-chloro-[1,3,5]triazin-2-yl)-amine (Example 3, Step 3) (80.0 mg, 0.238 mmol) in IpOH (3.0 ml) was added DIEA (0.062 mL, 0.356 mmol) and N-(4-aminophenyl)acrylamide (Example 2, Step 2) (42.4 mg, 0.261 mmol). The mix was heated at 100° C. for 18 h. The solution was then cooled to RT. A precipitate fells out of solution, was filtered off and dried under reduced pressure to give N-{4-[4-(1-benzyl-1H-indazol-5-ylamino)-[1,3,5]triazin-2-ylamino]-phenyl}-acrylamide: MS m/z=463 [M+H]$^+$. Calc'd for $C_{26}H_{22}N_8O$: 462.19.

EXAMPLE 6

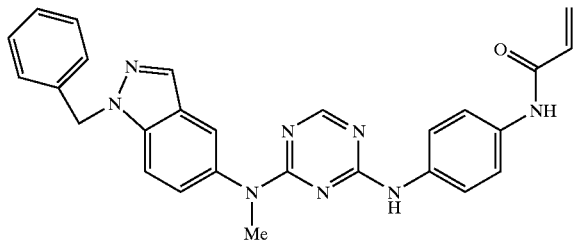

N-{4-(4-[(1-Benzyl-1H-indazol-5-yl)-methyl-amino]-[1,3,5]triazin-2-ylamino}-phenyl)-acrylamide To a slurry of (1-benzyl-1H-indazol-5-yl)-(4-chloro-[1,3,5]triazin-2-yl)methylamine (Example 4, Step 1)(80.0 mg, 0.228 mmol) in IpOH (3.0 ml) was added DIEA (0.06 mL, 0.342 mmol) and N-(4-aminophenyl)acrylamide (Example 2, Step 2) (40.7 mg, 0.251 mmol). The mix was heated at 100° C. for 18 h. The solution was then cooled to RT. A precipitate fell out of solution, was filtered off and dried under reduced pressure to give N-(4-{4-[(1-benzyl-1H-indazol-5-yl)-methyl-amino]-[1,3,5]triazin-2-ylamino}-phenyl)-acrylamide: MS m/z=477[M+H]$^+$. Calc'd for $C_{27}H_{24}N_8O$: 476.21.

EXAMPLE 7

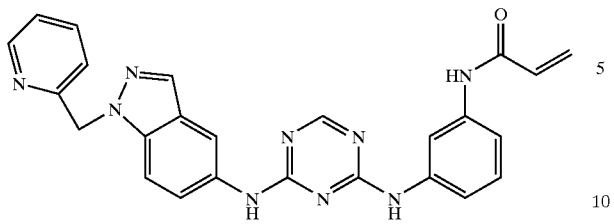

N-{3-[4-(1-Pyridin-2-ylmethyl-1H-indazol-5-ylamino)-[1,3,5]triazin-2-ylamino]-phenyl}-acrylamide Step 1: Preparation of 5-nitro-1-pyridin-2-ylmethyl-1H-indazole and 5-nitro-2-pyridin-2-ylmethyl-2H-indazole To a solution of 5-nitroindazole (2 g, 12.3 mmol) in DMF (20 mL) was added $K_2CO_3$ (5.1 g, 36.8 mmol) and 2-(bromomethyl)-pyridine (2.2 g, 13.5 mmol). The resulting mixture was stirred at RT for 3.5 days, then poured into 100 mL of water. The resulting slurry was filtered, rinsed once with water and dried in vacuo giving a solid. The crude material was purified by chromatography ($SiO_2$, elution with 3:1 EtOAc-hexanes followed by EtOAc followed by 7:1 $CH_2C_2$—MeOH) giving 5-nitro-1-pyridin-2-ylmethyl-1H-indazole and 5-nitro-2-pyridin-2-ylmethyl-1H-indazole.

Step 2: Preparation of 1-pyridin-2-ylmethyl-1H-indazol-5-ylamine

To 5-nitro-1-pyridin-2-ylmethyl-1H-indazole (Step 1) (671 mg, 2.63 mmol) in MeOH (15 mL) and EtOAc (5 mL) at RT was added a slurry of 10% Pd/C (150 mg) in MeOH (5 mL). The resulting slurry was stirred under a balloon of $H_2$ for 1.75 h, filtered through Celite®, and rinsed with MeOH and EtOAc. Concentration of the filtrate gave 1-pyridin-2-ylmethyl-1H-indazol-5-ylamine.

Step 3: Preparation of (4-chloro-[1,3,5]triazin-2-yl)-(1-pyridin-2-ylmethyl-1H-indazol-5-yl)-amine A mixture of the compound 2,4-dichloro-1,3,5-triazine (267 mg, 1.78 mmol) and solid $K_2CO_3$ (1.23 g, 8.42 mmol) was suspended in AcCN (20 mL) under nitrogen at 0° C. followed by addition of a solution of 1-pyridin-2-ylmethyl-1H-indazol-5-ylamine (Step 3) (400 mg, 1.78 mmol) in AcCN (3 mL) over 5 min. The mixture was stirred at 0° C. for 1 h. The reaction was quenched by pouring onto water. The organics were extracted into EtOAc (200 mL), washed with brine, dried over anh. $Na_2SO_4$, concentrated under reduced pressure then purified by column chromatography (elution with EtOAc followed by 9:1 $CH_2Cl_2$/MeOH) to give (4-chloro-[1,3,5]triazin-2-yl)-(1-pyridin-2-ylmethyl-1H-indazol-5-yl)-amine.

Step 4: Preparation of N-(3-[4-(1-pyridin-2-ylmethyl-1H-indazol-5-ylamino)-[1,3,5]triazin-2-ylamino]-phenyl}-acrylamide To a slurry of (4-chloro-[1,3,5]triazin-2-yl)-(1-pyridin-2-ylmethyl-1H-indazol-5-yl)-amine (Step 3) (90.0 mg, 0.266 mmol) in IpOH (3.0 ml) was added DIEA (0.07 mL, 0.40 mmol) and N-(3-aminophenyl)acrylamide (47.5 mg, 0.293 mmol). The mix was heated at 100° C. for 18 h. The solution was cooled to RT. A precipitate fell out of solution, was filtered off and dried under reduced pressure to give N-{3-[4-(1-pyridin-2-ylmethyl-1H-indazol-5-ylamino)-[1,3,5]triazin-2-ylamino]-phenyl}-acrylamide: MS m/z=464[M+H]$^+$. Calc'd for $C_{25}H_{21}N_9O$: 463.19.

EXAMPLE 8

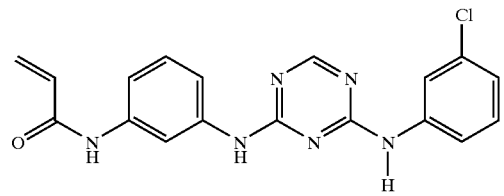

N-{3-[4-(3-Chloro-phenylamino)-[1,3,5]triazin-2-ylamino]-phenyl}-acrylamide

Step 1: Preparation of (3-chlorophenyl)-(4-chloro-[1,3,5]triazin-2-yl)amine

A mixture of 2,4-dichloro-1,3,5-triazine (4.0 g, 26.7 mmol) and solid $K_2CO_3$ (16.0 g, 116 mmol) was suspended in AcCN (50 mL) under nitrogen at 0° C. followed by addition of 3-chloroaniline (3.4 g, 26.7 mmol). The mixture was stirred at 0° C. for 0.5 h. The reaction was quenched by pouring onto ice/water. The white solid which formed was collected by suction filtration, dried under vacuum then purified by column chromatography (elution with $CH_2Cl_2$) to give (3-chlorophenyl)-(4-chloro-[1,3,5]triazin-2-yl)amine MS m/z=241. Calc'd for $C_9H_6Cl_2N_4$: 240.00.

Step 2: Preparation of N-{3-[4-(3-chloro-phenylamino)-[1,3,5]triazin-2-ylamino]-phenyl}-acrylamide To a slurry of (3-chlorophenyl)-(4-chloro-[1,3,5]triazin-2-yl)amine (Step 1) (80.0 mg, 0.332 mmol) in IpOH (2.5 ml) was added DIEA (0.087 mL, 0.50 mmol) and N-(3-aminophenyl)acrylamide (59.2 mg, 0.365 mmol). The mix was heated at 100° C. for 18 h. The solution was then cooled to RT. A precipitate fell out of solution, was filtered off and dried under reduced pressure to give N-{3-[4-(3-chlorophenylamino)-[1,3,5]triazin-2-ylamino]-phenyl}-acrylamide: MS m/z=367[M+H]. Calc'd for $C_{18}H_{15}ClN_6O$: 366.10.

EXAMPLE 9

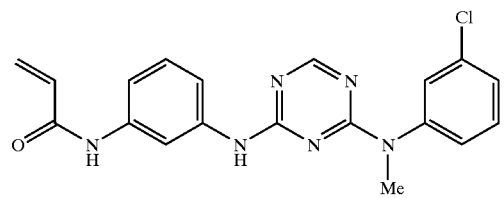

N-(3-{4-[(3-Chloro-phenyl)-methyl-amino]-[1,3,5]triazin-2-ylamino}-phenyl)-acrylamide Step 1: Preparation of (3-chlorophenyl)-(4-chloro-[1,3,5]triazin-2-yl)-methylamine A mixture of the compound 2,4-dichloro-1,3,5-triazine (2.5 g, 16.7 mmol) and solid $K_2CO_3$ (6.9 g, 49.9 mmol) was suspended in AcCN (50 mL) under nitrogen at 0° C. followed by addition of N-methyl-3-chloroaniline (2.5 g, 17.7 mmol). The mixture was stirred at 0° C. for 2 h. The reaction was quenched by pouring onto ice/water. The white solid formed was collected by suction filtration and dried under vacuum to give material identified as N-methyl-2-chloro-4-(3-chloroanilino)-1,3,5-triazine. MS m/z=255. Calc'd for $C_{10}H_8Cl_2N_4$: 254.01.

Step 2: Preparation of N-(3-{4-[(3-chlorophenyl)-methyl-amino]-[1,3,5]triazin-2-ylamino}-phenyl)-acrylamide To a slurry of N-methyl-2-chloro-4-(3-chloroanilino)-1,3,5-triazine (Step 1) (44.6 mg, 0.175 mmol) in IpOH (2.0 ml) was added DIEA (0.046 mL, 0.26 mmol) and N-(3-aminophenyl)acrylamide (31 mg, 0.192 mmol). The mix was heated at 100° C. for 18 h. The solution was then cooled to RT. The organics were concentrated under reduced pressure and the crude product was purified via column chromatography (elution with EtOAc) to give N-(3-{4-[(3-chlorophenyl)-methyl-amino]-[1,3,5]triazin-2-ylamino}-phenyl)-acrylamide: MS m/z=381 [M+H]$^+$. Calc'd for $C_{19}H_{17}ClN_6O$: 380.12.

EXAMPLE 10

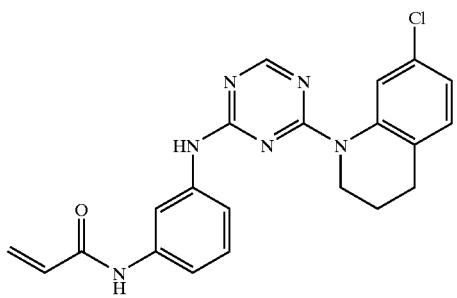

N-{3-[4-(7-Chloro-3,4-dihydro-2H-quinolin-1-yl)-[1,3,5]triazin-2-ylamino]-phenyl)-acrylamide Step 1: Preparation of 7-chloro-1,2,3,4-tetrahydro-quinoline Similar to the process reported by B. S. Rauckman, et. al., J. Med. Chemn., 1989, 32, 1927–1935, 4,7-dichloroquinoline (1.02 g, 5.1 mmol) was dissolved into anh. EtOH (30 mL) under $N_2$ at RT. Concentrated HCl (1.76 mL, 20.4 mmol) was added, followed by the addition of the NaCNBH$_3$ (1.28 g, 20.4 mmol). This produced vigorous gas and heat evolution. The reaction was heated to 60° C. for 2 h, then cooled and stirred at RT for an additional 18 h. The reaction was quenched by adjusting the pH to approximately 9 with 2 N NaOH. This mixture was extracted 3 times with EtOAc. The EtOAC extracts were washed brine, combined, dried over $Na_2SO_4$, filtered, and concentrated, then eluted through a 30×2.5 cm column of silica gel (3.75% EtOAc/Hexane) giving 7-chloro-1,2,3,4-tetrahydro-quinoline as an orange solid: MS m/z 168=[M+H]$^+$. Calc'd for $C_9H_{10}ClN$: 167.05.

Step 2: Preparation of 7-chloro-1-(4-chloro-[1,3,5]triazin-2-yl)-1,2,3,4-tetrahydro-quinoline A mixture of the compound 2,4-dichloro-1,3,5-triazine (1.0 g, 5.97 mmol) and solid $K_2CO_3$ (4.0 g, 29 mmol) was suspended in AcCN (20 mL) under nitrogen at 0° C., followed by slow addition of 7-chloro-1,2,3,4-tetrahydro-quinoline (Step 1) (1.1 g, 6.56 mmol) as a solution in AcCN (20 mL) over 15 min. The mixture was stirred at 0° C. for 1 h. The solids were removed by suction filtration and washed with AcCN. The organics were concentrated under reduced pressure and the crude compound was purified via column chromatography to give 7-chloro-1-(4-chloro-[1,3,5]triazin-2-yl)-1,2,3,4-tetrahydro-quinoline).

Step 3: Preparation of N-(3-[4-(7-chloro-3,4-dihydro-2H-quinolin-1-yl)-[1,3,5]triazin-2-ylamino]-phenyl}-acrylamide To a slurry of 7-chloro-1-(4-chloro-[1,3,5]triazin-2-yl)-1,2,3,4-tetrahydro-quinoline (Step 2)(70 mg, 0.249 mmol) in IpOH (2.0 ml) was added DIEA (0.20 mL, 1.15 mmol) and N-(3-aminophenyl)acrylamide (100 mg, 0.192 mmol). The heated at 100° C. for 18 h, then cooled to RT. The organics were concentrated under reduced pressure then purified by column chromatography (elution with $CH_2Cl_2$ followed by 99:1 $CH_2Cl_2$/MeOH followed by 97:3 $CH_2Cl_2$/MeOH) to give N-{3-[4-(7-chloro-3,4-dihydro-2H-quinolin-1-yl)-[1,3,5]triazin-2-ylamino]-phenyl}-acrylamide: MS m/z=407 [M+H]$^+$. Calc'd for $C_{21}H_{19}ClN_6O$: 406.13.

EXAMPLE 11

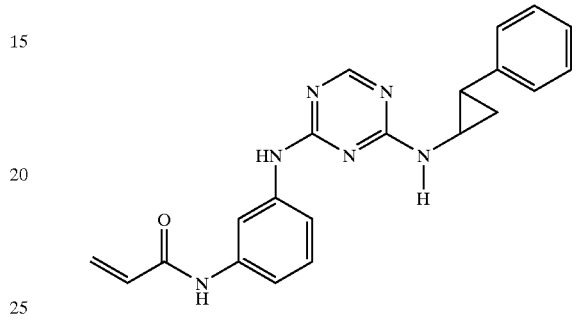

N-{3-[4-(2-Phenyl-cyclopropylamino)-[1,3,5]triazin-2-ylamino]-phenyl}-acrylamide Step 1: Preparation of (4-chloro-[1,3,5]triazin-2-yl)-(2-phenyl-cyclopropyl)amine A mixture of 2,4-dichloro-1,3,5-triazine (0.5 g, 3.34 mmol) and solid $K_2CO_3$ (2.3 g, 16.7 mmol) was suspended in ACCN (20 mL) under nitrogen at 0° C. followed by addition of trans-2-phenylcyclopropylamine hydrochloride (566 mg, 3.34 mmol). The mixture was stirred at 0° C. for 1.25 h. The reaction was quenched by pouring onto ice/water. The white solid formed was collected by suction filtration. The solid was dissolved into EtOAc (100 mL), washed with brine, dried over $Na_2SO_4$, concentrated under reduced pressure then purified by column chromatography (elution with 1:1 EtOAc/hexanes followed by EtOAc) to give (4-chloro-[1,3,5]triazin-2-yl)-(2-phenyl-cyclopropyl)amine.

Step 2: Preparation of N-{3-[4-(2-phenyl-cyclopropylamino)-[1,3,5]triazin-2-ylamino]-phenyl}-acrylamide To a slurry of (4-chloro-[1,3,5]triazin-2-yl)-(2-phenyl-cyclopropyl)amine (Step 1)(45.6 mg, 0.185 mmol) in IpOH (2.5 ml) was added DIEA (0.048 mL, 0.277 mmol) and N-(3-aminophenyl)acrylamide (53. mg, 0.203 mmol). The mix was heated at 100° C. for 18 h. The solution was then cooled to RT. A precipitate fell out of solution, was filtered off and dried under reduced pressure to give N-{3-[4-(2-phenyl-cyclopropylamino)-[1,3,5]triazin-2-ylamino]phenyl}-acrylamide: MS m/z=373 [M+H]. Calc'd for $C_{21}H_{20}N_6O$: 372.17.

EXAMPLE 12

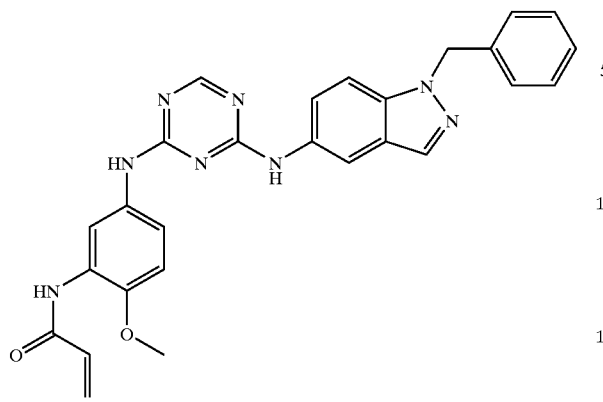

N-{5-[4-(1-Benzyl-1H-indazol-5-ylamino)-[1,3,5]triazin-2-ylamino]-2-methoxy-phenyl}-acrylamide Step 1: Preparation of N-(2-methoxy-5-nitro-phenyl)-acrylamide 2-Methoxy-5-nitroaniline (0.4 g, 2.38 mmol) was dissolved into $CH_2Cl_2$ (12 ml). To this solution was added EDC (1.37 g, 7.14 mmol), HOBT (964 mg, 7.14 mmol), DIEA (2.07 ml, 11.9 mmol) and acrylic acid (0.65 ml, 9.51 mmol). The reaction mixture was kept at RT for 4 h. The reaction mixture was diluted with EtOAc, washed with water, 1 N HCl, dilute $NaHCO_3$, then brine. The organic layer was dried over $Na_2SO_4$, filtered, and evaporated in vacuo. The residue was purified by column chromatography using 2:1 EtOAc/hexanes as the solvent to give N-(2-methoxy-5-nitrophenyl)-acrylamide.

Step 2: Preparation of N-(5-amino-2-methoxy-phenyl)-acrylamide

A mixture of N-(2-methoxy-5-nitro-phenyl)-acrylamide (Step 1) (335 mg, 1.51 mmol), iron powder (0.51 g, 9.0 mmol), $FeSO_4$ (839 mg, 3.02 mmol), Celite® (0.3 g) and water (9 mL) was heated to reflux with stirring for 3 h. The reaction mixture was cooled to RT. The solution was made basic to pH 13–14 by the addition of 2 N NaOH. The reaction mixture was diluted with EtOAc and water. The solution was filtered to remove the solids and solids were washed with EtOAc. The aqueous layer was extracted three times with EtOAc (100 mL) and the combined organics were dried over $Na_2SO_4$, filtered, and evaporated in vacuo. The residue was purified by column chromatography using EtOAc as the solvent to give N-(5-amino-2-methoxyphenyl)-acrylamide.

Step 3: Preparation of N-{5-[4-(1-benzyl-1H-indazol-5-ylamino)-[1,3,5]triazin-2-ylamino]-2-methoxyphenyl}-acrylamide To a slurry of (1-benzyl-1H-indazol-5-yl)-(4-chloro-[1,3,5]triazin-2-yl)-amine (Example 3, Step 3) (90 mg, 0.267 mmol) in IpOH (3 ml) was added DIEA (0.070 mL, 0.401 mmol) and N-(5-amino-2-methoxyphenyl)acrylamide (Step 2) (56.5 mg, 0.294 mmol). The mix was heated at 100° C. for 18 h. The solution was then cooled to RT. A precipitate fell out of solution, was filtered off and dried under reduced pressure to give N-{5-[4-(1-benzyl-1H-indazol-5-ylamino)-[1,3,5]triazin-2-ylamino]-2-methoxyphenyl}-acrylamide: MS m/z=493[M+H]$^+$. Calc'd for $C_{27}H_{24}N_8O_2$: 492.20.

EXAMPLE 13

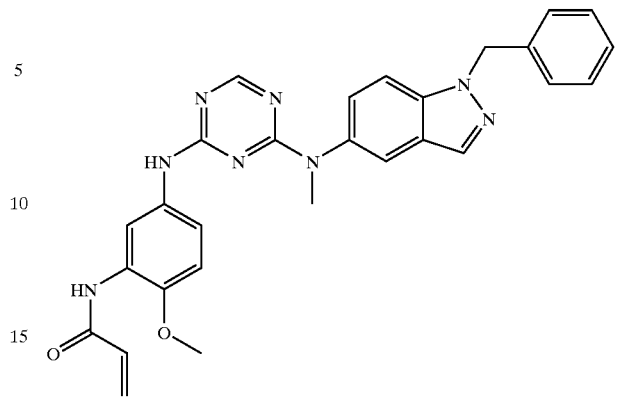

N-(5-{4-[(1-Benzyl-1H-indazol-5-yl)-methyl-amino]-[1,3,5]triazin-2-ylamino}-2-methoxy-phenyl)-acrylamide To a slurry of (1-benzyl-1H-indazol-5-yl)-(4-chloro-[1,3,5]triazin-2-yl)-amine (Example 3, Step 3) (90 mg, 0.256 mmol) in IpOH (3 ml) was added DIEA (0.067 mL, 0.385 mmol) and N-(5-amino-2-methoxy-phenyl)acrylamide (Example 12, Step 2) (54. mg, 0.282 mmol). The mixture was heated at 100° C. for 18 h. The solution was then cooled to RT. A precipitate fell out of solution, was filtered off and dried under reduced pressure to give N-(5-{4-[(1-benzyl-1H-indazol-5-yl)-methyl-amino]-[1,3,5]triazin-2-ylamino}-2-methoxyphenyl)acrylamide: MS m/z=507 [M+H]$^+$. Calc'd for $C_{28}H_{26}N_8O_2$: 506.22.

Other compounds included in this invention are set forth in Tables 1–4 below.

TABLE 1

| # | R$^5$ | R$^{5a}$ | R$^x$ |
|---|---|---|---|
| 14. | 1-benzylbenzopyrrol-5-yl | H | H |
| 15. | 2-(4-chlorophenyl)cyclopropyl | H | H |
| 16. | naphth-1-yl | H | H |
| 17. | 4-benzyloxy-phenyl | H | H |
| 18. | 4-benzyloxy-3-chlorophenyl | H | H |
| 19. | 3-chloro-4-fluorophenyl | H | H |
| 20. | 3-chloronaphth-1-yl | H | H |
| 21. | 4-methoxycarbonylphenyl | H | H |
| 22. | 3-(2-methoxyethoxy)-4-methoxy-phenyl | H | H |
| 23. | 3,4-dimethoxyphenyl | H | H |
| 24. | 2-oxo-3-tert-butylcarbonyl-2,3-dihydrobenzimidazol-1-yl | H | H |
| 25. | 2-oxo-2,3-dihydrobenzimidazol-1-yl | H | H |
| 26. | 3,4-diethoxyphenyl | H | H |
| 27. | 3,4-dipropoxy-phenyl | H | H |
| 28. | 3-methoxy-4-(2-methoxyethoxy)phenyl | H | H |
| 29. | 3-methylphenyl | H | H |
| 30. | 4,5-dimethoxy-3-(2-morpholin-4-yl-ethoxy)phenyl | H | H |

TABLE 1-continued

[Structure: R5(R5a)N-triazine-NH-phenyl(Rx)-NH-C(O)-CH=CH2]

| # | R5 | R5a | Rx |
|---|---|---|---|
| 31. | 3-aminocarbonylphenyl | H | H |
| 32. | 3-CH3OCOCH2-phenyl] | H | H |
| 33. | 3-(4-nitrophenylsulfonyl)-phenyl | H | H |
| 34. | 5-chloro-2-methyl-phenyl | H | H |
| 35. | 4-[HO(CH2)2O]phenyl | H | H |
| 36. | 1-benzylbenzopyrrol-5-yl | methyl | H |
| 37. | 2-pyridyl-CH2-indazol-5-yl | methyl | H |
| 38. | 2-phenylcyclopropyl | methyl | H |
| 39. | 2-(4-chlorophenyl)cyclapropyl | methyl | H |
| 40. | naphth-1-yl | methyl | H |
| 41. | 4-benzyloxy-phenyl | methyl | H |
| 42. | 4-benzyloxy-3-chlorophenyl | methyl | H |
| 43. | 3-chloro-4-fluorophenyl | methyl | H |
| 44. | 3-chloronaphth-1-yl | methyl | H |
| 45. | 4-methoxycarbonylphenyl | methyl | H |
| 46. | 3-(2-methoxyethoxy)-4-methoxy-phenyl | methyl | H |
| 47. | 3,4-dimethoxyphenyl | methyl | H |
| 48. | 2-oxo-3-tert-butylcarbonyl 2,3-dihydrobenzimidazol-1-yl | methyl | H |
| 49. | 2-oxo-2,3-dihydrobenzimidazol-1-yl | methyl | H |
| 50. | 3,4-diethoxyphenyl | methyl | H |
| 51. | 3,4-dipropoxy-phenyl | methyl | H |
| 52. | 3-methoxy-4-(2-methoxyethoxy)phenyl | methyl | H |
| 53. | 3-methylphenyl | methyl | H |
| 54. | 4,5-dimethoxy-3-(2-morpholin-4-yl-ethoxy)phenyl | methyl | H |
| 55. | 3-aminocarbonylphenyl | methyl | H |
| 56. | 3-CH3OCOCH2-phenyl] | methyl | H |
| 57. | 3-(4-nitrophenylsulfonyl)-phenyl | methyl | H |
| 58. | 5-chloro-2-methyl-Phenyl | methyl | H |
| 59. | 4-[HO(CH2)2O]phenyl | methyl | H |
| 60. | 1-benzylindazol-5-yl | allyl | H |
| 61. | 2-pyridyl-CH2-indazol-5-yl | allyl | H |
| 62. | 3-chlorophenyl | allyl | H |
| 63. | 2-phenylcyclaprapyl | allyl | H |
| 64. | 2-(4-chlorophenyl)cyclopropyl | allyl | H |
| 65. | naphth-1-yl | allyl | H |
| 66. | 4-benzyloxy-phenyl | allyl | H |
| 67. | 3-chloro-4-fluorophenyl | allyl | H |
| 68. | 3-chloronaphth-1-yl | allyl | H |
| 69. | 4-methoxycarbonylphenyl | allyl | H |
| 70. | 3-(2-methoxyethoxy)-4-methoxy-phenyl | allyl | H |
| 71. | 3,4-dimethoxyphenyl | allyl | H |
| 72. | 2-oxo-3-tert-butylcarbonyl 2,3-dihydrobenzimidazol-1-yl | allyl | H |
| 73. | 2-oxo-2,3-dihydrobenzimidazol-1-yl | allyl | H |
| 74. | 3,4-diethoxyphenyl | allyl | H |
| 75. | 3,4-dipropoxy-phenyl | allyl | H |
| 76. | 3-methoxy-4-(2-methoxyethoxy)phenyl | allyl | H |
| 77. | 3-methylphenyl | allyl | H |
| 78. | 4,5-dimethoxy-3-(2-morpholin-4-yl-ethoxy)phenyl | allyl | H |
| 79. | 3-aminocarbonylphenyl | allyl | H |
| 80. | 3-CH3OCOCH2-phenyl] | allyl | H |
| 81. | 3-(4-nitrophenylsulfonyl)-phenyl | allyl | H |
| 82. | 5-chloro-2-methyl-phenyl | allyl | H |
| 83. | 4-[HO(CH2)2O]phenyl | allyl | H |
| 84. | 1-benzylindazol-5-yl | ethyl | H |
| 85. | 2-pyridyl-CH2-indazol-5-yl | ethyl | H |
| 86. | 3-chlorophenyl | ethyl | H |
| 87. | 2-phenylcyclopropyl | ethyl | H |
| 88. | 2-(4-chlorophenyl)cyclopropyl | ethyl | H |
| 89. | naphth-1-yl | ethyl | H |
| 90. | 4-benzyloxy-phenyl | ethyl | H |
| 91. | 3-chloro-4-fluorophenyl | ethyl | H |
| 92. | 3-chloronaphth-1-yl | ethyl | H |
| 93. | 4-methoxycarbonylphenyl | ethyl | H |
| 94. | 3-(2-methoxyethoxy)-4-methoxy-phenyl | ethyl | H |
| 95. | 3,4-dimethoxyphenyl | ethyl | H |
| 96. | 2-oxo-3-tert-butylcarbonyl 2,3-dihydrobenzimidazol-1-yl | ethyl | H |
| 97. | 2-oxo-2,3-dihydrobenzimidazol-1-yl | ethyl | H |
| 98. | 3,4-diethoxyphenyl | ethyl | H |
| 99. | 3,4-dipropoxy-phenyl | ethyl | H |
| 100. | 3-methoxy-4-(2-methoxyethoxy)phenyl | ethyl | H |
| 101. | 3-methylphenyl | ethyl | H |
| 102. | 4,5-dimethoxy-3-(2-morpholin-4-yl-ethoxy)phenyl | ethyl | H |
| 103. | 3-aminocarbonylphenyl | ethyl | H |
| 104. | 3-CH3OCOCH2-phenyl] | ethyl | H |
| 105. | 3-(4-nitrophenylsulfonyl)-phenyl | ethyl | H |
| 106. | 5-chloro-2-methyl-Phenyl | ethyl | H |
| 107. | 4-[HO(CH2)2O]phenyl | ethyl | H |
| 108. | 1-benzylindazol-5-yl | H | 4-mpo |
| 109. | 1-benzylindazol-5-yl | methyl | 4-mpo |
| 110. | 1-benzylindazol-5-yl | H | 4-mpp |
| 111. | 1-benzylindazol-5-yl | methyl | 4-mpp |
| 112. | 3-chlorophenyl | H | 4-mpo |
| 113. | 3-chlorophenyl | methyl | 4-mpo |
| 114. | 3-chlorophenyl | H | 4-mpp |
| 115. | 3-chlorophenyl | methyl | 4-mpp |
| 116. | 4-benzyloxy-3-chlorophenyl | H | 4-mpo |
| 117. | 4-benzyloxy-3-chlorophenyl | methyl | 4-mpo |
| 118. | 4-benzyloxy-3-chlorophenyl | H | 4-mpp |
| 119. | 4-benzyloxy-3-chlorophenyl | methyl | 4-mpp |
| 120. | 1-benzylbenzopyrrol-5-yl | H | 4-mpo |
| 121. | 1-benzylbenzopyrrol-5-yl | methyl | 4-mpo |
| 122. | 1-benzylbenzopyrrol-5-yl | H | 4-mpp |
| 123. | 1-benzylbenzopyrrol-5-yl | methyl | 4-mpp |
| 124. | 3-Ethynyl-phenyl | H | H |
| 125. | 3-Bromophenyl | H | H |
| 126. | 4-Benzenesulfonylphenyl | H | H |
| 127. | 2-Benzyl-3H-benzoimidazol-5-yl | H | H |
| 128. | 1-(3-Fluoro-benzyl)-1H-indazol-5-yl | H | H |
| 129. | 4-(2-Bromobenzyloxy)-3-chlorophenyl | H | H |
| 130. | 4-(3-Fluoro-benzyloxy)phenyl | H | H |
| 131. | 3-Chloro-4-(3-fluorobenzyloxy)phenyl | H | H |
| 132. | 3-Trifluoromethyl-4-(3,4-dichloro-benzyloxy)phenyl | H | H |
| 133. | 3-fluoro-4-(3,4-difluoro-benzyloxy)phenyl | H | H |
| 134. | 3-Methoxy-4-(3-trifluoromethyl-benzyloxy)phenyl | H | H | mpo = 4-(morpholin-1-yl-propoxy)
mpp = 4-(1-methylpiperdin-4-yl-propoxy)

TABLE 2

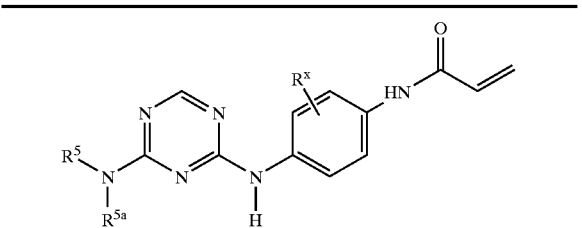

| # | R[5] | R[5a] | R[x] |
|---|------|-------|------|
| 135. | 1-benzylbenzopyrrol-5-yl | H | H |
| 136. | 2-pyridyl-CH$_2$-indazol-5-yl | H | H |
| 137. | 3-chlorophenyl | H | H |
| 138. | 2-phenylcyclopropyl | H | H |
| 139. | 2-(4-chlorophenyl)cyclopropyl | H | H |
| 140. | naphth-1-yl | H | H |
| 141. | 4-benzyloxy-phenyl | H | H |
| 142. | 4-benzyloxy-3-chlorophenyl | H | H |
| 143. | 3-chloro-4-fluorophenyl | H | H |
| 144. | 3-chloronaphth-1-yl | H | H |
| 145. | 4-methoxycarbonylphenyl | H | H |
| 146. | 3-(2-methoxyethoxy)-4-methoxy-phenyl | H | H |
| 147. | 4-methoxy-phenyl | H | H |
| 148. | 3,4-dimethoxyphenyl | H | H |
| 149. | 2-oxo-3-tert-butylcarbonyl 2,3-dihydrobenzimidazol-1-yl | H | H |
| 150. | 2-oxo-2,3-dihydrobenzimidazol-1-yl | H | H |
| 151. | 3,4-diethoxyphenyl | H | H |
| 152. | 3,4-dipropoxy-phenyl | H | H |
| 153. | 3-methoxy-4-(2-methoxyethoxy)phenyl | H | H |
| 154. | 3-methylphenyl | H | H |
| 155. | 4,5-dimethoxy-3-(2-morpholin-4-yl-ethoxy)phenyl | H | H |
| 156. | 3-aminocarbonylphenyl | H | H |
| 157. | 3-CH$_3$OCOCH$_2$-phenyl] | H | H |
| 158. | 3-(4-nitrophenylsulfonyl)-phenyl | H | H |
| 159. | 5-chloro-2-methyl-phenyl | H | H |
| 160. | 4-[HO(CH$_2$)$_2$O]phenyl | H | H |
| 161. | 1-benzylbenzopyrrol-5-yl | methyl | H |
| 162. | 2-pyridyl-CH$_2$-indazol-5-yl | methyl | H |
| 163. | 3-chlorophenyl | methyl | H |
| 164. | 2-phenylcyclopropyl | methyl | H |
| 165. | 2-(4-chlorophenyl)cyclopropyl | methyl | H |
| 166. | naphth-1-yl | methyl | H |
| 167. | 4-benzyloxy-phenyl | methyl | H |
| 168. | 4-benzyloxy-3-chlorophenyl | methyl | H |
| 169. | 3-chloro-4-fluorophenyl | methyl | H |
| 170. | 3-chloronaphth-1-yl | methyl | H |
| 171. | 4-methoxycarbonylphenyl | methyl | H |
| 172. | 3-(2-methoxyethoxy)-4-methoxy-phenyl | methyl | H |
| 173. | 3,4-dimethoxyphenyl | methyl | H |
| 174. | 2-oxo-3-tert-butylcarbonyl 2,3-dihydrobenzimidazol-1-yl | methyl | H |
| 175. | 2-oxo-2,3-dihydrobenzimidazol-1-yl | methyl | H |
| 176. | 3,4-diethoxyphenyl | methyl | H |
| 177. | 3,4-dipropoxy-phenyl | methyl | H |
| 178. | 3-methoxy-4-(2-methoxyethoxy)phenyl | methyl | H |
| 179. | 3-methylphenyl | methyl | H |
| 180. | 4,5-dimethoxy-3-(2-morpholin-4-yl-ethoxy)phenyl | methyl | H |
| 181. | 3-aminocarbonylphenyl | methyl | H |
| 182. | 3-CH$_3$OCOCH$_2$-phenyl] | methyl | H |
| 183. | 3-(4-nitrophenylsulfonyl)-phenyl | methyl | H |
| 184. | 5-chloro-2-methyl-phenyl | methyl | H |
| 185. | 4-[HO(CH$_2$)$_2$O]phenyl | methyl | H |
| 186. | 1-benzylindazol-5-yl | allyl | H |
| 187. | 2-pyridyl-CH$_2$-indazol-5-yl | allyl | H |
| 188. | 3-chlorophenyl | allyl | H |
| 189. | 2-phenylcyclopropyl | allyl | H |
| 190. | 2-(4-chlorophenyl)cyclopropyl | allyl | H |
| 191. | naphth-1-yl | allyl | H |
| 192. | 4-benzyloxy-phenyl | allyl | H |
| 193. | 3-chloro-4-fluorophenyl | allyl | H |
| 194. | 3-chloronaphth-1-yl | allyl | H |
| 195. | 4-methoxycarbonylphenyl | allyl | H |
| 196. | 3-(2-methoxyethoxy)-4-methoxy-phenyl | allyl | H |
| 197. | 3,4-dimethoxyphenyl | allyl | H |
| 198. | 2-oxo-3-tert-butylcarbonyl 2,3-dihydrobenzimidazol-1-yl | allyl | H |
| 199. | | | |
| 200. | 2-oxo-2,3-dihydrobenzimidazol-1-yl | allyl | H |
| 201. | 3,4-diethoxyphenyl | allyl | H |
| 202. | 3,4-dipropoxy-phenyl | allyl | H |
| 203. | 3-methoxy-4-(2-methoxyethoxy)phenyl | allyl | H |
| 204. | 3-methylphenyl | allyl | H |
| 205. | 4,5-dimethoxy-3-(2-morpholin-4-yl-ethoxy)phenyl | allyl | H |
| 206. | 3-aminocarbonylphenyl | allyl | H |
| 207. | 3-CH$_3$OCOCH$_2$-phenyl] | allyl | H |
| 208. | 3-(4-nitrophenylsulfonyl)phenyl | allyl | H |
| 209. | 5-chloro-2-methyl-phenyl | allyl | H |
| 210. | 4-[HO(CH$_2$)$_2$O]phenyl | allyl | H |
| 211. | 1-benzylindazol-5-yl | ethyl | H |
| 212. | 2-pyridyl-CH$_2$-indazol-5-yl | ethyl | H |
| 213. | 3-chlorophenyl | ethyl | H |
| 214. | 2-phenylcyclopropyl | ethyl | H |
| 215. | 2-(4-chlorophenyl)cyclopropyl | ethyl | H |
| 216. | naphth-1-yl | ethyl | H |
| 217. | 4-benzyloxy-phenyl | ethyl | H |
| 218. | 3-chloro-4-fluorophenyl | ethyl | H |
| 219. | 3-chloronaphth-1-yl | ethyl | H |
| 220. | 4-methoxycarbonylphenyl | ethyl | H |
| 221. | 3-(2-methoxyethoxy)-4-methoxy-phenyl | ethyl | H |
| 222. | 3,4-dimethoxyphenyl | ethyl | H |
| 223. | 2-oxo-3-tert-butylcarbonyl 2,3-dihydrobenzimidazol-1-yl | ethyl | H |
| 224. | 2-oxo-2,3-dihydrobenzimidazol-1-yl | ethyl | H |
| 225. | 3,4-diethoxyphenyl | ethyl | H |
| 226. | 3,4-dipropoxy-phenyl | ethyl | H |
| 227. | 3-methoxy-4-(2-methoxyethoxy)phenyl | ethyl | H |
| 228. | 3-methylphenyl | ethyl | H |
| 229. | 4,5-dimethoxy-3-(2-morpholin-4-yl-ethoxy)phenyl | ethyl | H |
| 230. | 3-aminocarbonylphenyl | ethyl | H |
| 231. | 3-CH$_3$OCOCH$_2$-phenyl] | ethyl | H |
| 232. | 3-(4-nitrophenylsulfonyl)-phenyl | ethyl | H |
| 233. | 5-chloro-2-methyl-phenyl | ethyl | H |
| 234. | 4-[HO(CH$_2$)$_2$O]phenyl | ethyl | H |
| 235. | 1-benzylindazol-5-yl | H | 3-methoxy |
| 236. | 1-benzylindazol-5-yl | methyl | 3-methoxy |

TABLE 3

| # | R5 | R5a | Rx |
|---|---|---|---|
| 237. | 1-benzylbenzopyrrol-5-yl | H | H |
| 238. | 1-benzylindazol-5-yl | H | H |
| 239. | 2-pyridyl-CH₂-indazol-5-yl | H | H |
| 240. | 3-chlorophenyl | H | H |
| 241. | 2-phenylcyclopropyl | H | H |
| 242. | 2-(4-chlorophenyl)cyclopropyl | H | H |
| 243. | naphth-1-yl | H | H |
| 244. | 4-benzyloxy-phenyl | H | H |
| 245. | 4-benzyloxy-3-chlorophenyl | H | H |
| 246. | 3-chloro-4-fluorophenyl | H | H |
| 247. | 3-chloronaphth-1-yl | H | H |
| 248. | 4-methoxycarbonylphenyl | H | H |
| 249. | 3-(2-methoxyethoxy)-4-methoxy-phenyl | H | H |
| 250. | 3,4-dimethoxyphenyl | H | H |
| 251. | 2-oxo-3-tert-butylcarbonyl 2,3-dihydrobenzimidazol-1-yl | H | H |
| 252. | 2-oxo-2,3-dihydrobenzimidazol-1-yl | H | H |
| 253. | 3,4-diethoxyphenyl | H | H |
| 254. | 3,4-dipropoxy-phenyl | H | H |
| 255. | 3-methoxy-4-(2-methoxyethoxy)phenyl | H | H |
| 256. | 3-methylphenyl | H | H |
| 257. | 4,5-dimethoxy-3-(2-morpholin-4-yl-ethoxy)phenyl | H | H |
| 258. | 3-aminocarbonylphenyl | H | H |
| 259. | 3-CH₃OCOCH₂-phenyl] | H | H |
| 260. | 3-(4-nitrophenylsulfonyl)-phenyl | H | H |
| 261. | 5-chloro-2-methyl-phenyl | H | H |
| 262. | 4-[HO(CH₂)₂O]phenyl | H | H |
| 263. | 1-benzylindazol-5-yl | methyl | H |
| 264. | 1-benzylbenzopyrrol-5-yl | methyl | H |
| 265. | 2-pyridyl-CH₂-indazol-5-yl | methyl | H |
| 266. | 3-chlorophenyl | methyl | H |
| 267. | 2-phenylcyclopropyl | methyl | H |
| 268. | 2-(4-chlorophenyl)cyclopropyl | methyl | H |
| 269. | naphth-1-yl | methyl | H |
| 270. | 4-benzyloxy-phenyl | methyl | H |
| 271. | 4-benzyloxy-3-chlorophenyl | methyl | H |
| 272. | 3-chloro-4-fluorophenyl | methyl | H |
| 273. | 3-chloronaphth-1-yl | methyl | H |
| 274. | 4-methoxycarbonylphenyl | methyl | H |
| 275. | 3-(2-methoxyethoxy)-4-methoxy-phenyl | methyl | H |
| 276. | 3,4-dimethoxyphenyl | methyl | H |
| 277. | 2-oxo-3-tert-butylcarbonyl 2,3-dihydrobenzimidazol-1-yl | methyl | H |
| 278. | 2-oxo-2,3-dihydrobenzimidazol-1-yl | methyl | H |
| 279. | 3,4-diethoxyphenyl | methyl | H |
| 280. | 3,4-dipropoxy-phenyl | methyl | H |
| 281. | 3-methoxy-4-(2-methoxyethoxy)phenyl | methyl | H |
| 282. | 3-methylphenyl | methyl | H |
| 283. | 4,5-dimethoxy-3-(2-morpholin-4-yl-ethoxy)phenyl | methyl | H |
| 284. | 3-aminocarbonylphenyl | methyl | H |
| 285. | 3-CH₃OCOCH₂-phenyl] | methyl | H |
| 286. | 3-(4-nitrophenylsulfonyl)-phenyl | methyl | H |
| 287. | 5-chloro-2-methyl-phenyl | methyl | H |
| 288. | 4-[HO(CH₂)₂O]phenyl | methyl | H |
| 289. | 1-benzylindazol-5-yl | allyl | H |
| 290. | 2-pyridyl-CH₂-indazol-5-yl | allyl | H |
| 291. | 3-chlorophenyl | allyl | H |
| 292. | 2-phenylcyclopropyl | allyl | H |
| 293. | 2-(4-chlorophenyl)cyclopropyl | allyl | H |
| 294. | naphth-1-yl | allyl | H |
| 295. | 4-benzyloxy-phenyl | allyl | H |
| 296. | 3-chloro-4-fluorophenyl | allyl | H |
| 297. | 3-chloronaphth-1-yl | allyl | H |
| 298. | 4-methoxycarbonylphenyl | allyl | H |
| 299. | 3-(2-methoxyethoxy)-4-methoxy-phenyl | allyl | H |
| 300. | 3,4-dimethoxyphenyl | allyl | H |
| 301. | 2-oxo-3-tert-butylcarbonyl 2,3-dihydrobenzimidazol-1-yl | allyl | H |
| 302. | 2-oxo-2,3-dihydrobenzimidazol-1-yl | allyl | H |
| 303. | 3,4-diethoxyphenyl | allyl | H |
| 304. | 3,4-dipropoxy-phenyl | allyl | H |
| 305. | 3-methoxy-4-(2-methoxyethoxy)phenyl | allyl | H |
| 306. | 3-methylphenyl | allyl | H |
| 307. | 4,5-dimethoxy-3-(2-morpholin-4-yl-ethoxy)phenyl | allyl | H |
| 308. | 3-aminocarbonylphenyl | allyl | H |
| 309. | 3-CH₃OCOCH₂-phenyl] | allyl | H |
| 310. | 3-(4-nitrophenylsulfonyl)-phenyl | allyl | H |
| 311. | 5-chloro-2-methyl-Phenyl | allyl | H |
| 312. | 4-[HO(CH₂)₂O]phenyl | allyl | H |
| 313. | 1-benzylindazol-5-yl | ethyl | H |
| 314. | 2-pyridyl-CH₂-indazol-5-yl | ethyl | H |
| 315. | 3-chlorophenyl | ethyl | H |
| 316. | 2-phenylcyclopropyl | ethyl | H |
| 317. | 2-(4-chlorophenyl)cyclopropyl | ethyl | H |
| 318. | naphth-1-yl | ethyl | H |
| 319. | 4-benzyloxy-phenyl | ethyl | H |
| 320. | 3-chloro-4-fluorophenyl | ethyl | H |
| 321. | 3-chloronaphth-1-yl | ethyl | H |
| 322. | 4-methoxycarbonylphenyl | ethyl | H |
| 323. | 3-(2-methoxyethoxy)-4-methoxy-phenyl | ethyl | H |
| 324. | 3,4-dimethoxyphenyl | ethyl | H |
| 325. | 2-oxo-3-tert-butylcarbonyl 2,3-dihydrobenzimidazol-1-yl | ethyl | H |
| 326. | 2-oxo-2,3-dihydrobenzimidazol-1-yl | ethyl | H |
| 327. | 3,4-diethoxyphenyl | ethyl | H |
| 328. | 3,4-dipropoxy-phenyl | ethyl | H |
| 329. | 3-methoxy-4-(2-methoxyethoxy)phenyl | ethyl | H |
| 330. | 3-methylphenyl | ethyl | H |
| 331. | 4,5-dimethoxy-3-(2-morpholin-4-yl-ethoxy)phenyl | ethyl | H |
| 332. | 3-aminocarbonylphenyl | ethyl | H |
| 333. | 3-CH₃OCOCH₂-phenyl] | ethyl | H |
| 334. | 3-(4-nitrophenylsulfonyl)-phenyl | ethyl | H |
| 337. | 5-chloro-2-methyl-phenyl | ethyl | H |
| 338. | 4-[HO(CH₂)₂O]phenyl | ethyl | H |
| 339. | 1-benzylindazol-5-yl | H | 4-methoxy |
| 340. | 1-benzylindazol-5-yl | methyl | 4-methoxy |
| 341. | 1-benzylindazol-5-yl | H | 4-mpo |
| 342. | 1-benzylindazol-5-yl | methyl | 4-mpo |
| 343. | 1-benzylindazol-5-yl | H | 4-mpp |
| 344. | 1-benzylindazol-5-yl | methyl | 4-mpp |
| 345. | 3-chlorophenyl | H | 4-mpo |
| 346. | 3-chlorophenyl | methyl | 4-mpo |
| 347. | 3-chlorophenyl | H | 4-mpp |
| 348. | 3-chlorophenyl | methyl | 4-mpp |
| 349. | 4-benzyloxy-3-chlorophenyl | H | 4-mpo |
| 350. | 4-benzyloxy-3-chlorophenyl | methyl | 4-mpo |

TABLE 3-continued

| # | R⁵ | R⁵ᵃ | Rˣ |
|---|---|---|---|
| 351. | 4-benzyloxy-3-chlorophenyl | H | 4-mpp |
| 352. | 4-benzyloxy-3-chlorophenyl | methyl | 4-mpp |
| 353. | 1-benzylbenzopyrrol-5-yl | H | 4-mpo |
| 354. | 1-benzylbenzopyrral-5-yl | methyl | 4-mpo |
| 355. | 1-benzylbenzopyrrol-5-yl | H | 4-mpp |
| 356. | 1-benzylbenzopyrrol-5-yl | methyl | 4-mpp | mpo = 4-(morpholin-1-yl-propoxy)
mpp = 4-(1-methylpiperdin-4-yl-propoxy)

TABLE 4

| # | R⁵ | Rᵃ |
|---|---|---|
| 357. | 1-benzylbenzopyrrol-5-yl | 1,3-butadienyl |
| 358. | 1-benzylindazol-5-yl | 1-propenyl |
| 359. | 2-pyridyl-CH₂-indazol-5-yl | 2-propenyl |
| 360. | 3-chlorophenyl | 2-propenyl |
| 361. | 2-phenylcyclopropyl | 1-propenyl |
| 362. | 2-(4-chlorophenyl)cyclopropyl | 1,3-butadienyl |

TABLE 5

| # | R⁵ | R⁵* |
|---|---|---|
| 363. | 1-benzylindazol-5-yl | H |
| 364. | 1-benzylindazol-5-yl | methyl |
| 365. | 3-chlorophenyl | H |
| 366. | 3-chlorophenyl | methyl |
| 367. | 2-pyridyl-CH₂-indazol-5-yl | H |
| 368. | 2-phenylcyclopropyl | methyl |
| 369. | 2-(4-chlorophenyl)cyclopropyl | H |
| 370. | naphth-1-yl | H |
| 371. | 4-benzyloxy-phenyl | H |
| 372. | 3-chloro-4-fluorophenyl | H |
| 373. | 3-chloronaphth-1-yl | H |
| 374. | 4-methoxycarbonylphenyl | H |
| 375. | 3,4-dimethoxyphenyl | H |
| 376. | 3-methylphenyl | H |
| 377. | 5-chloro-2-methyl-phenyl | H |
| 378. | 4-[HO(CH₂)₂O]phenyl | H |

TABLE 6

| # | R⁵ | R⁵ᵃ |
|---|---|---|
| 379. | 1-benzylindazol-5-yl | 1-(CH₂=CH—CO)-2,3-dihydrobenzopyrrol-6-yl |
| 380. | 1-benzylindazol-5-yl | 1-(CH₂=CH—CO)-2,3-dihydrobenzopyrrol-5-yl |
| 381. | 1-benzylindazol-5-yl | 1-(CH₂=CH—CO)-indazol-5-yl |
| 382. | 1-benzylindazol-5-yl | 1-(CH₂=CH—CO)-indazol-6-yl |
| 383. | 1-benzylindazoJ-5-yl | 3-(N-morphalinylpropyl-acrylamidyl)phenyl |

TABLE 7

| # | R¹ | R⁵ |
|---|---|---|
| 384. | 7-Cl-tetrahydroquinol-1-yl | 3-(CH₂=CH—CO—NH)-phenyl |
| 385. | 7-Cl-tetrahydroquinol-1-yl | 3-(CH₂=CH—CO—NH)-4-mpo-phenyl |
| 386. | 7-Cl-tetrahydroquinol-1-yl | 3-(CH₂=CH—CO—N(mpo))-phenyl |
| 387. | 7-Cl-tetrahydraquinol-1-yl | 3-butynamidylphenyl |
| 388. | 7-Cl-tetrahydraquinol-1-yl | 3-(CH₂=CH—CO—N(mpp))-phenyl |
| 389. | 7-Cl-tetrahydroquinol-1-yl | 3-(CH₂=CH—CO—NH)-4-mpp-phenyl |
| 390. | 7-CF₃-tetrahydraquinolin-1-yl | 3-(CH₂=CH—CO—NH)-phenyl |
| 391. | 6-methyl-tetrahydroquinolin-1-yl | 3-(CH₂=CH—CO—NH)-phenyl |
| 392. | 6-methoxy-tetrahydroquinlin-1-yl | 3-(CH₂=CH—CO—NH)-phenyl |
| 393. | 5-Cl-tetrahydraquinolin-1-yl | 3-(CH₂=CH—CO—NH)-phenyl |
| 394. | 6-Cl-tetrahydroquinolin-1-yl | 3-(CH₂=CH—CO—NH)-phenyl |
| 395. | 7-CF₃-tetrahydroquinolin-1-yl | 4-(CH₂=CH—CO—NH)-phenyl |
| 396. | 6-methyl-tetrahydroquinolin-1-yl | 4-(CH₂=CH—CO—NH)-phenyl |
| 397. | 6-methoxy-tetrahydroquinolin-1-yl | 4-(CH₂=CH—CO—NH)-phenyl |
| 398. | 5-Cl-tetrahydroquinolin-1-yl | 4-(CH₂=CH—CO—NH)-phenyl |
| 399. | 6-Cl-tetrahydroquinolin-1-yl | 4-(CH₂=CH—CO—NH)-phenyl |
| 400. | 7-CF₃-tetrahydroquinolin-1-yl | 3-butynamidylphenyl |
| 401. | 6-methyl-tetrahydroquinolin-1-yl | 3-butynamidylphenyl |
| 402. | 6-methoxy-tetrahydroquinolin-1-yl | 3-butynamidylphenyl |
| 403. | 5-1-tetrahydroquinolin-1-yl | 3-butynamidylphenyl |
| 404. | 6-Cl-tetrahydroquinolin-1-yl | 3-butynamidylphenyl |

Although the pharmacological properties of the compounds of Formula I vary with structural change, in general, activity possessed by compounds of Formula I may be demonstrated in vivo. The pharmacological properties of the compounds of this invention may be confirmed by a number of pharmacological in vitro assays. The exemplified pharmacological assays which follow have been carried out with the compounds according to the invention and their salts.

Biological Evaluation

Kinase Inhibition

The compounds described herein are screened in the following manner. Kinases suitable for use in the following protocol to determine kinase activity of the compounds described herein include, but are not limited to: Lck, Lyn, Src, Fyn, Syk, Zap-70, Itk, Tec, Btk, EGFR, ErbB2, Kdr, Flt-1, Flt-3, Tek, c-Met, InsR, and Atk.

Kinases are expressed as either kinase domains or full length constructs fused to glutathione S-transferase (GST) or polyHistidine tagged fusion proteins in either *E. coli* or Baculovirus-High Five expression systems. They are purified to near homogeneity by affinity chromatography essentially as previously described (Lehr et al., 1996; Gish et al., 1995). In some instances, kinases are co-expressed or mixed with purified or partially purified regulatory polypeptides prior to measurement of activity.

Kinase activity and inhibition are measured essentially by established protocols (Braunwalder et al., 1996). Briefly, The transfer of $^{33}PO_4$ from ATP to the synthetic substrates poly(Glu, Tyr) 4:1 or poly(Arg, Ser) 3:1 attached to the bioactive surface of microtiter plates serves as the basis to evaluate enzyme activity. After an incubation period, the amount of phosphate transferred is measured by first washing the plate with 0.5% phosphoric acid, adding liquid scintillant, and then counting in a liquid scintillation detector. The $IC_{50}$ is determined by the concentration of compound that causes a 50% reduction in the amount of $^{33}P$ incorporated onto the substrate bound to the plate.

Other similar methods whereby phosphate is transferred to peptide or polypeptide substrate containing tyrosine, serine, threonine, or histidine, either alone, in combination, or in combination with other amino acids, in solution or immobilized (i.e., solid phase) are also useful. For example, transfer of phosphate to a peptide or polypeptide can also be detected using scintillation proximity (Wu et al., 2000), ELISA (Cleaveland et al., 1990), Fluorescence Polarization (Seethala and Menzel, 1998), and homogeneous time-resolved fluorescence (HTRF, Kolb et al., 1998). Alternatively, kinase activity can be measured using antibody-based methods whereby an antibody or polypeptide is used as a reagent to detect phosphorylated target polypeptide. Compounds of the present invention showed inhibition of EGFR kinase at doses less than 50 µm.

References

Braunwalder et al. (1996). *Anal. Biochem.* 234(1):23–26.
Cleaveland et al. (1990). *Anal Biochem.* 190(2):249–53.
Gish et al. (1995). *Protein Eng.* 8(6):609–614.
Kolb et al. (1998). *Drug Discov. Today.* 3:333–342.
Lehr et al. (1996). *Gene* 169(2):27527–9.
Seethala et al. (1998). *Anal Biochem.* 255(2):257–62.
Wu et al. (2000). *Comb Chem High Throughput Screen.* 3(1):27–36.

ErbB Project Cell Assay Summary Protocols

1. EGF Rat-1 DNA Synthesis.

A rat fibroblast cell line (Rat-1) is plated out in flat-well plates in complete medium and allowed to adhere overnight. The cells are then starved in medium containing 0.1% bovine serum albumin (BSA) overnight, pre-incubated for 1 h with or without dilutions of compound, then activated overnight with 1 ng/ml epidermal growth factor (EGF), 50 ng/ml platelet derived growth factor (PDGF), 3 ng/ml fibroblast growth factor (FGF), or 10 ng/ml insulin-like growth factor-1 (IGF-1). Proliferation is determined by the level of $^3$H-thymidine incorporation into DNA. $IC_{50}$'s are determined by comparing the level of thymidine incorporation found in the presence of compound compared to controls.

2. EGF-R Auto-Phosphorylation in A431.

Human epidermoid carcinoma cells (A431; ATCC, Manassas, Va.) are plated out in flat-well plates in complete media and allowed to adhere overnight. The cells are then starved in medium containing 0.5% fetal calf serum (FCS), pre-incubated with or without dilutions of compound, then activated for 3 min with 50 ng/ml EGF. The cells are lysed and proteins are separated by SDS-PAGE. The level of phosphotyrosine on EGF-R is determined by western blotting with an anti-phospho-EGF-R-specific antibody. $IC_{50}$'s are determined by comparing the level of phosphotyrosine found in the presence of compound compared to controls.

3. HRGβ1 T47D DNA Synthesis.

The human breast tumor cell line (T47D; ATCC, Manassas, Va.) is plated out in flat-well plates in complete medium and allowed to adhere overnight. The cells are then starved in medium containing 0.1% bovine serum albumin (BSA) overnight, pre-incubated for 1 h with or without dilutions of compound, then activated overnight with 150 ng/ml Heregulin (HRGβ1). Proliferation is determined by the level of $^3$H-thymidine incorporation into DNA. $IC_{50}$'s are determined by comparing the level of thymidine incorporation found in the presence of compound compared to controls.

4. ErbB2 Auto-Phosphorylation in T47D.

Human breast tumor cells (T47D; ATCC, Manassas, Va.) are plated out in flat-well plates in complete media and allowed to adhere overnight. The cells are then starved in medium containing 0.1% bovine serum albumin (BSA), pre-incubated with or without dilutions of compound, then activated for 10 min with 900 ng/ml HRGβ1. The cells are lysed and proteins are separated by SDS-PAGE. The level of phosphotyrosine on ErbB2 is determined by western blotting with an anti-phospho-ErbB2-specific antibody. $IC_{50}$'s are determined by comparing the level of phosphotyrosine found in the presence of compound compared to controls.

5. HRGβ1 3T3-Her2/3 DNA Synthesis.

A mouse fibroblast cell line (3T3) has been stably transfected with full length human ErbB2 and ErbB3 (Ke Zhang, Amgen, TO). This cell line is plated out in flat-well plates in complete medium and allowed to adhere overnight. The cells are then starved in medium containing 0.1% bovine serum albumin (BSA) overnight, pre-incubated for 1 h with or without dilutions of compound, then activated overnight with 25 ng/ml Heregulin (HRGβ1). Proliferation is determined by the level of $^3$H-thymidine incorporation into DNA. $IC_{50}$'s are determined by comparing the level of thymidine incorporation found in the presence of compound compared to controls.

Tumor Model

A431 cells (ATCC) are expanded in culture, harvested and injected subcutaneously into 6–8 week old female nude mice (CD1 nu/nu, Charles River Labs) (n=10). Subsequent administration of compound (1% Tween 80 in water) by oral gavage (150, 75 and 37.5 mpk/dose) begins on the day of tumor cell challenge and continues twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (1% Tween 80 in water) is the negative control. Compounds of the present invention will be active at doses less than 150 mpk.

Formulations

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units were tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amount of compounds which were administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients were dissolved or suspended in suitable carrier, especially an aqueous solvent for the active ingredients. The active ingredients were preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but were not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$, and $\gamma$-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which were commonly used include lactose and corn starch. Lubricating agents, such as magnesium stearate, were also typically added. For oral administration in a capsule form, useful diluents include lactose and dried corn starch. When aqueous suspensions and/or emulsions were administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may comprise formulations utilizing liposome or microencapsulation techniques. Such techniques were known in the art.

The pharmaceutical compositions of this invention may be administered by nasal aerosol or inhalation. Such compositions were prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of Formula III

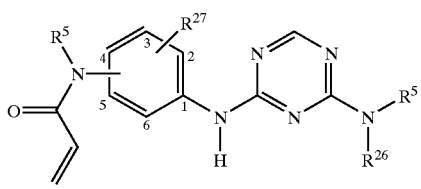

wherein $R^5$ is selected from H, $C_{1-4}$ alkyl and $C_{1-4}$ alkyl substituted with 5–10 membered heterocyclyl;

wherein $R^{26}$ is selected from 5–10 membered heterocyclyl, phenyl and $C_{3-6}$ cycloalkyl;

or wherein $R^5$ and $R^{26}$ together form a nitrogen containing 5–10-membered heterocyclic ring;

wherein $R^{27}$ is selected from H, $C_{1-4}$ alkyl, fluoro, chloro, $NO_2$, CN, $CF_3$, $C_2$–$C_3$ alkenyl, $C_2$–$C_3$ alkynyl, —$OR^{28}$, —$OC(O)R^{28}$, —$NR^{28}R^{28}$, —$COOR^2$, —$C(O)R^{28}$, —$C(O)NR^{28}R^{28}$, —$SO_2R^{28}$, —$SO_2NR^{28}R^{28}$, —$NR^{28}C(O)NR^{28}R^{28}$, —$NR^{28}C(O)R^2$, —$NR^{28}(COOR^{28})$, —$NR^{28}SO_2NR^{28}R^{28}$, —$NR^{28}SO_2R^{28}$, —$OCC(O)NR^{28}R^{28}$, $C_3$–$C_6$ cycloalkyl, $C_4$–$C_6$ cycloalkenyl, phenyl, 5–6 membered heterocyclyl, $C_{1-4}$ alkoxy, phenyloxy, 5–10 membered heterocyclyloxy $C_{1-4}$ haloalkyl, phenyl-$C_{1-4}$ alkyl, phenyl-$C_{1-4}$ alkoxy, 5–10 membered heterocyclyl-$C_{1-4}$ alkyl, and 5–10 membered heterocyclyl-$C_{1-4}$ alkoxy;

wherein $R^{28}$ is selected from H, $C_{1-4}$ alkyl, phenyl, and 5–6-membered heterocyclyl;

wherein heterocyclyl is optionally substituted with one or more substituents selected from $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{28}$, —$OC(O)R^{28}$, —$NR^{28}R^{28}$, —$COOR^2$, —$C(O)R^{28}$, —$C(O)NR^{28}R^{28}$, —$SO_2R^{28}$, —$NR^{28}SO_2R^{28}$, —$OC(O)NR^{28}R^{28}$, and $C_1$–$C_3$ alkyl substituted with 1–3 substituents independently selected from optionally substituted phenyl and optionally substituted 5–6 membered heterocyclyl;

wherein phenyl is optionally substituted with one or more substituents selected from $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{28}$, —$OC(O)R^{28}$, —$NR^{28}R^{28}$, —$COOR^2$, —$C(O)R^{28}$, —$C(O)NR^{28}R^{28}$, —$SO_2R^{28}$, —$SO_2NR^{28}R^{28}$, —$NR^{28}C(O)NR^{28}R^{28}$, —$NR^{28}C(O)R^2$, —$NR^{28}(COOR^{28})$, —$NR^{28}SO_2NR^{28}R^{28}$, —$NR^{28}SO_2R^{28}$, —$OC(O)NR^{28}R^{28}$, and $C_1$–$C_3$ alkyl substituted with 1–3 substituents independently selected from optionally substituted phenyl and optionally substituted 5–6 membered heterocyclyl;

wherein cycloalkyl is optionally substituted with one or more substituents selected from $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{28}$, —$OC(O)R^{28}$, —$NR^{28}R^{28}$, —$COOR^2$, —$C(O)R^{28}$, —$C(O)NR^{28}R^{28}$, —$SO_2R^{28}$, —$SO_2NR^{28}R^{28}$, —$NR^{28}C(O)NR^{28}R^{28}$, —$NR^{28}C(O)R^2$, —$NR^{28}(COOR^{28})$, —$NR^{28}SO_2NR^{28}R^{28}$, —$NR^{28}SO_2R^{28}$, —$OC(O)NR^{28}R^{28}$, and $C_1$–$C_3$ alkyl substituted with 1–3 substituents independently selected from optionally substituted phenyl and optionally substituted 5–6 membered heterocyclyl;

and a pharmaceutically acceptable salt thereof.

2. Compound of claim 1 wherein $R^5$ is selected from H, methyl and $C_{1-3}$ alkyl substituted with optionally substituted morpholinyl, optionally substituted piperdinyl or optionally substituted piperazinyl;

wherein $R^{26}$ is selected from optionally substituted indazolyl, optionally substituted benzopyrrolyl, optionally substituted phenyl and optionally substituted cyclopropyl;

or wherein $R^5$ and $R^{26}$ together form an optionally substituted heterocyclic ring selected from pyrrolidinyl, morpholinyl, piperdinyl, piperazinyl, tetrahydroisoquinolinyl and tetrahyciroquinolinyl;

wherein $R^{27}$ is selected from H, $C_{1-4}$ alkyl, fluoro, chloro, CN, $CF_3$, —$OR^{28}$, —$OC(O)R^{28}$, —$NR^{28}R^{28}$, —$COOR^2$, —$C(O)R^{28}$, —$C(O)NR^{28}R^{28}$, —$SO_2R^{28}$, —$SO_2NR^{28}R^{28}$, phenyl, 5–6 membered heterocyclyl, $C_{1-4}$ haloalkyl, phenyl-$C_{1-4}$ alkyl, phenyl-$C_{1-4}$ alkoxy, 5–10 membered heterocyclyl-$C_{1-4}$ alkyl, and 5–10 membered heterocyclyl-$C_{1-4}$ alkoxy;

wherein $R^{28}$ is selected from H, methyl, ethyl and optionally substituted phenyl;

wherein heterocyclyl is optionally substituted with one or more substituents selected from $C_1$–$C_3$ alkyl, $C_2$–$C_3$ alkenyl, $C_3$–$C_6$ cycloalkyl, phenyl, 5–6 membered heterocyclyl, fluoro, chloro, $CF_3$, —$OR^{28}$, —$OC(O)R^{28}$, $NR^{28}R^{28}$, —$COOR^{28}$, —$C(O)R^{28}$, —$C(O)NR^{28}R^{28}$, $C_1$–$C_3$ alkyl substituted with optionally substituted phenyl or optionally substituted 5–6 membered heterocyclyl;

wherein phenyl is optionally substituted with one or more substituents selected from $C_1$–$C_3$ alkyl, $C_2$–$C_3$ alkenyl, $C_3$–$C_6$ cycloalkyl, phenyl, 5–6 membered heterocyclyl, fluoro, chloro, $CF_3$, —$OR^{28}$, —$OC(O)R^{28}$, —$NR^{28}R^{28}$, —$COOR^{28}$, —$C(O)R^{28}$, —$C(O)NR^{28}R^{28}$, $C_1$–$C_3$ alkyl substituted with optionally substituted phenyl or optionally substituted 5–6 membered heterocyclyl;

wherein cycloalkyl is optionally substituted with one or more substituents selected from $C_1$–$C_3$ alkyl, $C_2$–$C_3$ alkenyl, $C_3$–$C_6$ cycloalkyl, phenyl, 5–6 membered heterocyclyl, fluoro, chloro, $CF_3$, —$OR^{28}$, —$OC(O)R^{28}$, —$NR^{28}R^{28}$, —$COOR^{28}$, —$C(O)R^{28}$, —$C(O)NR^{28}R$, $C_1$–$C_3$ alkyl substituted with optionally substituted phenyl or optionally substituted 5–6 membered heterocyclyl;

and a pharmaceutically acceptable salt thereof.

3. Compound of claim 2 wherein $R^5$ is selected from H, methyl and $C_{1-3}$ alkyl substituted with optionally substituted morpholinyl, optionally substituted piperdinyl or optionally substituted piperazinyl;

wherein $R^{26}$ is selected from optionally substituted indazolyl, optionally substituted benzopyrrolyl, arid optionally substituted phenyl;

or wherein $R^5$ and $R^{26}$ together form an optionally substituted heterocyclic ring selected from morpholinyl, piperdinyl, piperazinyl, tetrahydroisoquinolinyl and tetrahydroquinolinyl;

wherein $R^{27}$ is selected from H, methyl, fluoro, chloro, methoxy, phenylpropoxy, 1-methylpiperazinylpropoxy, morpholinylpropoxy and 1-methylpiperidinylpropoxy; and wherein $R^{28}$ is selected from H, methyl, ethyl and optionally substituted phenyl;

wherein heterocyclyl is optionally substituted with one or more substituents selected from $C_1$–$C_3$ alkyl, $C_3$–$C_6$ cycloalkyl, phenyl, fluoro, chloro, —$OR^{28}$, $CF_3$, —OC(O)$R^{28}$, —$NR^{28}R^{28}$, —$COOR^{28}$, —C(O)$R^{28}$, —C(O)$NR^{28}R^{28}$, and $C_1$–$C_3$ alkyl substituted with optionally substituted phenyl or optionally substituted 5–6 membered heterocyclyl;

wherein phenyl is optionally substituted with one or more substituents selected from $C_1$–$C_3$ alkyl, 5–6 membered heterocyclyl, fluoro, chloro, $CF_3$, —$OR^{28}$, —OC(O)$R^{28}$, —$NR^{28}R^{28}$, —$COOR^{28}$, —C(O)$R^{28}$, —C(O)$NR^{28}R^{28}$, and $C_1$–$C_3$ alkyl substituted with optionally substituted phenyl or optionally substituted 5–6 membered heterocyclyl;

wherein cycloalkyl is optionally substituted with optionally substituted phenyl;

and a pharmaceutically acceptable salt thereof.

4. A pharmaceutical composition comprising a pharmaceutically-acceptable carrier and a compound of claim 1.

5. A method of treating cancer in a subject, said cancer is selected from esophagus tumor, glioma, Non-small-cell lung cancer, stomach tumor, kidney cell, sarcoma, Liver tumor, pancreas tumor, prostate tumor, bladder tumor, cervix tumor, breast tumor, carcinoma, head & neck tumor, ovary tumor and colorectal tumor, said method comprising administering an effective amount of a compound of claim 1.

6. A method of treating polycystic kidney disease in a subject, said method comprising administering an effective amount of a compound of claim 1.

7. Compound of claim 1 and a pharmaceutically acceptable salt thereof selected from N-{3-[4-(3,4,5-trimethoxy-phenylamino)-[1,3,5]triazin-2-ylamino]-phenyl}-acrylamide;

N-{4-[4-(3,4,5-trimethoxy-phenyJ.amino)-[1,3,5]triazin-2-ylamino]-phenyl}-acrylamide;

N-(3-{4-[(1-benzyl-1H-indazol-5-yl)-methyl-amino]-[1,3,5]triazin-2-ylamino}-phenyl)-acrylamide;

N-{4-[4-(1-benzyl-1H-indazol-5-yl)-methyl-amino)-[1,3,5]triazin-2-ylamino}-phenyl)-acrylamide;

N-(4-{4-[(1-benzyl-1H-indazol-5-yl)-methyl-amino]-[1,3,5]triazin-2-ylamino}-phenyl)-acrylamide;

N-{3-[4-(1-benzyl-1H-indazol-5-ylamino)-[1,3,5]triazin-2-ylamino]-phenyl}-acrylamide;

N-{3-[4-(1-pyridin-2-ylmethyl-1H-indazol-5-ylamino)-[1,3,5]triazin-2-ylamino]-phenyl}-acrylamide;

N-{3-[4-(3-chloro-phenylamino)-[1,3,5]triazin-2-ylamino]-phenyl}-acrylamide;

N-(3-{4-[(3-chloro-phenyl)-methyl-amino]-[1,3,5]triazin-2-ylamino}-phenyl)-acrylamide;

N-{3-[4-(7-chloro-3,4-dihydro-2H-quinolin-1-yl)-[1,3,5]triazin-2-ylamino]-phenyl}-acrylamide;

N-{3-[4-(2-phenyl-cyclopropylamino)-[1,3,5]triazin-2-ylamino]-phenyl}-acrylamide;

N-{5-[4-(1-benzyl-1H-indazol-5-ylamino)-[1,3,5]triazin-2-ylamino]-2-methoxy-pheny}-acrylamide;

N-(5-{4-[(1-benzyl-1H-indazol-5-yl)-methyl-amino]-[1,3,5]triazin-2-ylamino}-2-methoxy-phenyl)-acrylamide;

N-[5-[4-(3-chloro-phenylamino)-[1,3,5]triazin-2-ylamino]-2-(3-morpholin-4-yl-propoxy)-phenyl]-acrylamide;

N-[5-[4–1-benzyl-1H-indazol-5-ylamino)-[1,3,5]triazin-2-ylamino]-2-(3-morpholin-4-yl-propoxy)-phenyl]-acrylamide;

N-[5-{4-[(1-benzyl-1H-indazol-5-yl)-methyl-amino]-[1,3,5]triazin-2-ylamino}-2-(3-morpholin-4-yl-propoxy)-phenyl]-acrylamide;

N-[5-[4-(7-chloro-3,4-dihydro-2H-quinolin-1-yl)-[1,3,5]triazin-2-ylamino]-2-(3-morpholin-4-yl-propoxy)-phenyl]-acrylamide;

N-[5-{4-[(3-chloro-phenyl)-methyl-amino]-[1,3,5]triazin-2-ylamino}-2-(3-morpholin-4-yl-propoxy)-phenyl]-acrylamide;

N-[5-{4-[(3-chloro-phenyl)-methyl-amino]-[1,3,5]triazin-2-ylamino)-2-[3-(4-methyl-piperazin-1-yl)-propoxy]-phenyl}-acrylamide;

N-{5-[4-(3-chloro-phenylamino)-[1,3,5]triazin-2-ylamino]-2-[3-(4-methyl-piperazin-1-yl)-propoxy]-phenyl}-acrylamide;

N-{5-[4-(1-benzyl-1H-indazol-5-ylamino)-[1,3,5]triazin-2-ylamino]-2-[3-(4-methyl-piperazin-1-yl)-propoxy]-phenyl}-acrylamide;

N-{5-{4-[(1-benzyl-1H-indazol-5-yl)-methyl-amino]-[1,3,5]triazin-2-ylamino}-2-[3-(4-methyl-piperazin-1-yl)-propoxy]-phenyl}-acrylamide;

N-{5-[4-(7-chloro-3,4-dihydro-2H-quinolin-1-yl)-[1,3,5]triazin-2-ylamino]-2-[3-(4-methyl-piperazin-1-yl)-propoxy]-phenyl}-acrylamide;

N-(3-{4-[(4-benzyloxy-phenyl)-methyl-amino]-[1,3,5]triazin-2-ylamino}-phenyl)-acrylamide;

N-{3-[4-(4-benzyloxy-phenylamino)-[1,3,5]triazin-2-ylamino]-phenyl}-acrylamide;

N-{3-[4-(1-benzyl-1H-indol-5-ylamino)-[1,3,5]triazin-2-ylamino]-phenyl}-acrylamide;

N-(3-{4-[(1-benzyl-1H-indol-5-yl)-methyl-amino]-[1,3,5]triazin-2-ylamino}-phenyl)-acrylamide;

N-(3-{4-[(4-benzyloxy-3-chloro-phenyl)-methyl-amino]-[1,3,5]triazin-2-ylamino}-phenyl)-acrylamide;

N-{3-[4-(4-benzyloxy-3-chloro-phenylamino)-[1,3,5]triazin-2-ylamino]-phenyl}-acrylamide;

N-[5-[4-(1-benzyl-1H-indol-5-ylamino)-[1,3,5]triazin-2-ylamino]-2-(3-morpholin-4-yl-propoxy)-phenyl]-acrylamide;

N-[5-{4-[(1-benzyl-1H-indol-5-yl)-methyl-amino]-[1,3,5]triazin-2-ylamino}-2-(3-morpholin-4-yl-propoxy)-phenyl]-acrylamide;

N-[5-{4-[(4-benzyloxy-3-chloro-phenyl)-methyl-amino]-[1,3,5]triazin-2-ylamino}-2-(3-morpholin-4-yl-propoxy)-phenyl]-acrylamide; and N-[5-[4-(4-benzyloxy-3-chloro-phenylamino)-[1,3,5]triazin-2-ylaminol]-2-(3-morpholin-4-yl-propoxy)-phenyl]-acrylamide.

* * * * *